(12) United States Patent
Kaneko et al.

(10) Patent No.: US 11,795,151 B2
(45) Date of Patent: Oct. 24, 2023

(54) BENZOTRIAZOLE COMPOUND

(71) Applicant: MIYOSHI OIL & FAT CO., LTD., Tokyo (JP)

(72) Inventors: Nobuhiro Kaneko, Tokyo (JP); Kotaro Kaneko, Tokyo (JP); Koji Kawai, Tokyo (JP)

(73) Assignee: MIYOSHI OIL & FAT CO., LTD., Tokyo (JP)

( * ) Notice: Subject to any disclaimer, the term of this patent is extended or adjusted under 35 U.S.C. 154(b) by 0 days.

(21) Appl. No.: 16/755,979

(22) PCT Filed: Oct. 26, 2018

(86) PCT No.: PCT/JP2018/039952
§ 371 (c)(1),
(2) Date: Apr. 14, 2020

(87) PCT Pub. No.: WO2019/087983
PCT Pub. Date: May 9, 2019

(65) Prior Publication Data
US 2020/0325107 A1 Oct. 15, 2020

(30) Foreign Application Priority Data

Oct. 31, 2017 (JP) ................ 2017-210517
Jul. 4, 2018 (JP) ................ 2018-127835

(51) Int. Cl.
C07D 249/20 (2006.01)
C08K 5/3475 (2006.01)

(52) U.S. Cl.
CPC .......... *C07D 249/20* (2013.01); *C08K 5/3475* (2013.01)

(58) Field of Classification Search
CPC .................................................. C07D 249/20
See application file for complete search history.

(56) References Cited

U.S. PATENT DOCUMENTS

| 3,629,191 | A | 12/1971 | Heller et al. | |
|---|---|---|---|---|
| 3,629,192 | A | 12/1971 | Heller et al. | |
| 8,262,947 | B2 * | 9/2012 | Laredo | C07D 249/20 623/6.11 |
| 10,316,024 | B2 * | 6/2019 | Kawai | C07C 321/26 |
| 2003/0098440 | A1 * | 5/2003 | Musa | C07D 403/10 252/182.13 |
| 2017/0217937 | A1 | 8/2017 | Kawai et al. | |
| 2018/0134872 | A1 | 5/2018 | Shishino et al. | |

FOREIGN PATENT DOCUMENTS

| JP | S63-055542 | A | | 3/1988 |
|---|---|---|---|---|
| JP | H06505743 | A | | 6/1994 |
| JP | 2000-119569 | A | | 4/2000 |
| JP | 2001-234072 | A | | 8/2001 |
| JP | 2002-172865 | A | | 6/2002 |
| JP | 2002-226521 | A | | 8/2002 |
| JP | 2002-226522 | A | | 8/2002 |
| JP | 2003-168243 | A | | 6/2003 |
| JP | 2012-25811 | A | | 2/2012 |
| JP | 2012-532196 | A | | 12/2012 |
| JP | 3178898 | A1 | | 6/2017 |
| JP | 2018-122450 | A | | 8/2018 |
| JP | 2018122450 | A | * | 8/2018 |
| WO | WO-2016021664 | A1 | * | 2/2016 |

OTHER PUBLICATIONS

Chemical Abstracts Registry No. 155687-66-4 {indexed in the Registry file on STN CAS Online Jun. 14, 1994. (Year: 1994).*
A machine generated English translation of JP 2018-122450 A, (Sano), 2018. (Year: 2018).*
Sapozhnikov et al., Russian Chemical Bulletin, International Edition, 2004, vol. 53, No. 3, 588-595.
International Search Report mailed in PCT/JP2018/039952 dated Jan. 22, 2019.
Extended European Search Report received in EP 18874505.3 dated May 12, 2021.
Examination Report dated Aug. 2, 2021 in corresponding Indian Application No. 202017019161.
Japanese Office Action for JapaneseApplication No. 2019-550335, dated Oct. 4, 2022 with English translation.

* cited by examiner

*Primary Examiner* — Laura L Stockton
(74) *Attorney, Agent, or Firm* — FOX ROTHSCHILD LLP

(57) ABSTRACT

Provided is a benzotriazole compound that efficiently absorbs ray having a long wavelength of 360-400 nm, i) having excellent solubility in a monomer of a resin raw material, being dissolvable at a high concentration, polymerizing at excellent reactivity, and yielding a high-molecular-weight resin member and a transparent resin member, or ii) having exceptional heat resistance. This benzotriazole compound is represented by formula (I), where at least one of $R^1$-$R^9$ is represented by formula (i-1), (where $R^{10}$ and R11 are hydrocarbon groups, etc., and $R^{12}$ is represented by formula (i-2) or formula (i-3) (in formula (i-2), $A^1$ represents a divalent group selected from nitrogen-Containing groups, oxygen-containing groups, sulfur-containing groups, phosphorus-containing groups, and phenylene groups, and $R^{12a}$-$R^{12c}$ and X represent hydrocarbon groups, etc.; and in formula (i-3), $A^2$ represents a divalent group selected from nitrogen-containing groups, oxygen-containing groups, sulfur-containing groups, and phosphorus-containing groups, and $X^a$ and $X^b$ represent hydrocarbon groups, etc.)).

28 Claims, 10 Drawing Sheets

BENZOTRIAZOLE COMPOUND

TECHNICAL FIELD

The present invention relates to a benzotriazole compound having an ultraviolet absorbing affect.

BACKGROUND ART

A resin member is deteriorated by the action of ultraviolet rays, and causes quality deterioration such as discoloration and a decrease in mechanical strength, thereby hindering long-term use.

In order to prevent such quality deterioration or to control the wavelength of transmitted light, it is common practice to blend an ultraviolet absorber into a resin member.

Conventionally, ultraviolet absorbers such as benzotriazole-based, benzophenone-based, triazine-based, cyanoacrylate-based, and salicylate-based ones have been known as organic ultraviolet absorbers. Conventional organic ultraviolet absorbers, such as benzotriazole compounds have had problems that they are subject to bleed-out of the added ultraviolet absorber from the resin, and difficult to add at high concentrations if the compatibility with a resin or a monomer is low. Patent Documents 1 to 5 disclose compounds in which an acryloyloxy group having reactivity with a monomer or a resin is introduced into a 2-phenylbezotriazole skeleton via an alkylene group or an alkylene group in which ether oxygen is introduced into a base end. Since these compounds have reactivity with monomers and resins, bleed-out can be suppressed. However there has been room for further improvement in order to satisfy solubility in monomers and resins, reactivity enabling high molecular weight, and transparency of resin member as a whole. In addition, as the ultraviolet absorption efficiency of the harmful long wavelength in the vicinity of 360 to 400 nm is low, there has been a problem that when an additive amount thereof is increased to compensate for this, light with 400 nm or more wavelength is absorbed, thus leading to the occurrence of yellowing.

The present inventors proposed 2-phenylbenzotriazole derivatives having a sulfur-containing group as an ultraviolet absorber which efficiently and sufficiently absorbs harmful light of 380 to 400 nm in particular and suppresses absorption of light with 400 nm or more wavelength that triggers initial yellowing (Patent Documents 6 and 7). These ultraviolet absorbers can sufficiently absorb light in a wavelength range of 250 to 400 nm from their optical property; have such a high ultraviolet absorption effect (molar absorption coefficient) that can efficiently absorb that wavelength of light by adding a small amount thereof; and have a slope of absorption peak of 350 to 390 nm that is larger than those of conventional ultraviolet absorbers, thereby capable of suppressing absorption of light with a wavelength in the vicinity of 400 nm or more and suppressing initial yellowing of a member to which the agent is added. In their working examples, compounds in which an allyl group is banded to a 2-phenylbenzotriazole skeleton via a sulfur atom are synthesized, but there is room for further improvement in reactivity which enables high molecular weight and solubility in a monomer as a resin raw material.

Organic ultraviolet absorbers may be thermally decomposed when a resin composition containing an ultraviolet absorber is heated and molded and processed, leading to a decrease in ultraviolet absorbing ability of a resin member, an impaired transparency in the case of the resin member being transparent, and further, leading to a possibility that the inside of the molding and processing apparatus may be contaminated therewith. Accordingly, an organic ultraviolet absorber having more excellent heat resistance has been required. In Patent Documents 6 and 7, as the sulfur-containing group of the 2-phenylbenzotriazole derivative, there e synthesized sulfur-containing groups in which a hydrocarbon group consisting of carbon and hydrogen such as an aliphatic or aromatic compound is bonded to the sulfur at a base end. However, when used for a resin requiring a high molding/processing temperature, there have been concerns about the possibilities of a decrease in ultraviolet absorbing ability due to decomposition of the ultraviolet absorber, loss of transparency of a transparent resin member, and contamination of a device at the time of processing. For this reason, there has been a need for an ultraviolet absorber having excellent heat resistance that enables the application to a resin requiring a higher molding/processing temperature.

PRIOR ART DOCUMENTS

Patent Documents

Patent Document 1: JPA 2012-25811
Patent Document 2: JPA 2000-119569
Patent Document 3: JPA 2001-234072
Patent Document 4: JPA 2002-226521
Patent Document 5: PA 2002-226522
Patent Document 6: WO 2016/021664
Patent Document 7: WO 2016/174788

SUMMARY OF THE INVENTION

Problems to be Solved by the Invention

The present invention has been made in view of the above circumstances, and it is an object of the present invention to provide a benzotriazole compound that efficiently absorbs ultraviolet light having a long wavelength of 360 to 400 m, has good solubility in monomers of resin raw materials, and can be dissolved at a high concentration, and is polymerizable with good reactivity to obtain a high molecular weight resin member, and further a transparent resin member; and a polymer containing the benzotriazole compound as a raw material monomer.

Another object of the present invention is to provide a benzotriazole compound that efficiently absorbs ultraviolet rays having a long wavelength of 360 to 400 m and has excellent heat resistance.

Means to Solve the Problems

In order to solve the above problems, the present invention provides a benzotriazole compound represented by the following formula (I).

[Chemical formula 1]

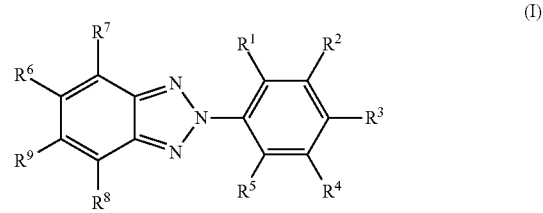

In the above formula, each of $R^1$ to $R^9$ independently represents a monovalent group selected from a monovalent sulfur-containing group represented by the following formula (i-1), a hydrogen atom, a hydrocarbon group having 1 to 10 carbon atoms, an aromatic group, an unsaturated group, a nitrogen-containing group, a sulfur-containing group, an oxygen-containing group, a phosphorus-containing group, an alicyclic group and a halogen atom, provided that at least one of $R^1$ to $R^9$ is the monovalent sulfur-containing group represented by the following formula (i-1).

[Chemical formula 2]

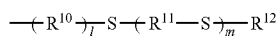

(i-1)

In the (i-1), 1 represents an integer of 0 or 1; m represents an integer of 0 to 3; $R^{10}$ represents a divalent hydrocarbon group having 1 to 20 carbon atoms in which hydrogen atoms may be substituted with, at least one of two ends may be interrupted by, or carbon-carbon bonds may be interrupted by a monovalent or divalent group selected from an aromatic group, an unsaturated group, a nitrogen-containing group, a sulfur-containing group, an oxygen-containing group, a phosphorus-containing group, an alicyclic group and a halogen atom; $R^{11}$ represents a divalent hydrocarbon group having 1 to 20 carbon atoms in which hydrogen atoms may be substituted with, at least one of two ends may be interrupted by, or carbon-carbon bonds may be interrupted by a monovalent or divalent group selected from an aromatic group, an unsaturated group, a nitrogen-containing group, a sulfur-containing group, an oxygen-containing group, a phosphorus-containing group, an alicyclic group and a halogen atom with the proviso that each of $R^{11}$ is independent when m is not smaller than 2.

<1> In the first embodiment of the invention, $R^{12}$ represents a monovalent group expressed by the following formula (i-2).

[Chemical formula 3]

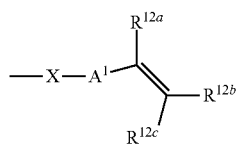

(i-2)

In the above formula, each of $R^{12a}$, $R^{12b}$ and $R^{12c}$ independently represents a hydrogen atom or a monovalent hydrocarbon group having 1 to 18 carbon atoms; $A^1$ represents a divalent group selected from a nitrogen-containing group, an oxygen-containing group, a sulfur-containing group, a phosphorus-containing group and a phenylene group; X represents a divalent group selected from $-X^1-$, $-X^2-$, $-X^1-(Y)_p-X^1-$ and $-X^2-(Y)_p-X^2-$, wherein $X^1$ represents a divalent hydrocarbon group having 1 to 20 carbon atoms in which hydrogen atoms may be substituted with, at least one of two ends may be interrupted by, or carbon-carbon bonds may be interrupted by a monovalent or divalent group selected from an aromatic group, an unsaturated group, a nitrogen-containing group, a sulfur-containing group, an oxygen-containing group, a phosphorus-containing group, an alicyclic group and a halogen atom; $X^2$ represents a divalent aromatic group; Y represents a hetero atom; p represents an integer of 0 or 1.

<2> In the second embodiment of the invention, $R^{12}$ represents a monovalent group expressed by the following formula (i-3).

[Chemical Formula 4]

(i-3)

In the above formula, $A^2$ represents a divalent group selected from a nitrogen-containing group, an oxygen-containing group, a sulfur-containing group, and a phosphorus-containing group; $X^a$ represents a divalent group selected from $-X^{a1}-$, $-X^{a2}-$, $-X^{a1}-(Y^a)_q-X^{a2}-$, $-X^{a2}-(Y^a)_q-X^{a1}-$ and $-X^{a2}-(Y^a)_q-X^{a2}-$ wherein $X^{a1}$ represents a divalent hydrocarbon group having 1 to 20 carbon atoms in which hydrogen atoms may be substituted with, at least one of two ends may be interrupted by, or carbon-carbon bonds may be interrupted by a monovalent or divalent group selected from an aromatic group, an unsaturated group, a nitrogen-containing group, a sulfur-containing group, an oxygen-containing group, a phosphorus-containing group, an alicyclic group, and a halogen atom, whereas $X^{a2}$ represents a divalent aromatic group, $Y^a$ represents a heteroatom, and q represents an integer of 0 or 1; $X^b$ represents a monovalent group selected from $-X^{b1}$, $-X^{b2}$, $-X^{a1}-(Y^b)_r-X^{b2}$, $-X^{a2}-(Y^b)_r-X^{b1}$, and $-X^{a2}-(Y^b)_r-X^{b2}$ wherein $X^{b1}$ represents a monovalent hydrocarbon group having 1 to 20 carbon atoms in which hydrogen atoms may be substituted with, at least one of two ends may be interrupted by, or carbon-carbon bonds may be interrupted by a monovalent or divalent group selected from an aromatic group, an unsaturated group, a nitrogen-containing group, a sulfur-containing group, an oxygen-containing group, a phosphorus-containing group, an alicyclic group, and a halogen atom, whereas $X^{b2}$ represents a monovalent aromatic group, $Y^b$ represents a heteroatom, and r represents an integer of 0 or 1, provided that $X^{a1}$ and $X^{a2}$ represent the same as above, but are each independent from those of $X^a$.

Effects of the Invention

The benzotriazole compound of the present invention according to the first aspect described above is highly soluble in a monomer of a resin raw material, can be dissolved at a high concentration, and polymerizes with good reactivity. Accordingly, a resin member of high molecular weight and further a transparent resin member can be obtained. Moreover, heat resistance is improved by introducing a nitrogen-containing group, an oxygen-containing group, a sulfur-containing group, a phosphorus-containing group, or a phenylene group as $A^1$ of $R^{12}$ into the sulfur-containing group.

The benzotriazole compound of the present invention according to the second aspect introduces a nitrogen-containing group, an oxygen-containing group, a sulfur-containing group, or a phosphorus-containing group as $A^2$ of $R^{12}$ into the sulfur-containing group. As a result, the heat resistance is improved, the thermal decomposition thereof is suppressed, and the deterioration of the ultraviolet absorption ability and appearance can be suppressed. In particular, since it is difficult to be thermally decomposed in the process of heat molding and processing it can be applied as an ultraviolet absorber even to a resin that requires a higher molding temperature.

Further, the benzotriazole compound of the present invention according to the first and second aspects described above, due to the structure in which sulfur is introduced into the 2-phenylbenzotriazole skeleton, can sufficiently absorb light in a wavelength region of 250 to 400 nm due to its optical characteristics. Moreover, the ultraviolet absorption effect (molar extinction coefficient) is high, thus light of that wavelength can be efficiently absorbed with a small amount of addition. Furthermore, the absorption peak of 350 to 390 n has a larger slope than that of the conventional ultraviolet absorber thus absorption of light having a wavelength of about 400 nm or more can be suppressed, and initial yellowing of the blended member can be suppressed.

MODE FOR CARRYING OUT THE INVENTION

Figure 1:
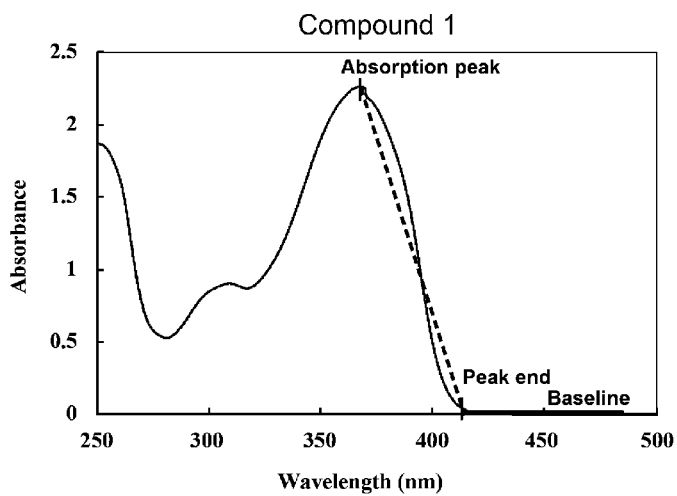
FIG. 1 is an ultraviolet-visible absorption spectrum (UV chart) of Compound 1 according to a working example of the present invention.
Figure 2:
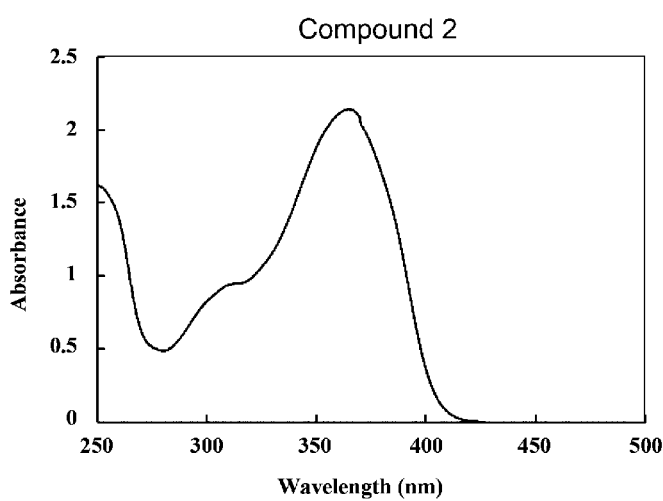
FIG. 2 is an ultraviolet-visible absorption spectrum (UV chart) of Compound 2 according to a working example of the present invention.
Figure 3:
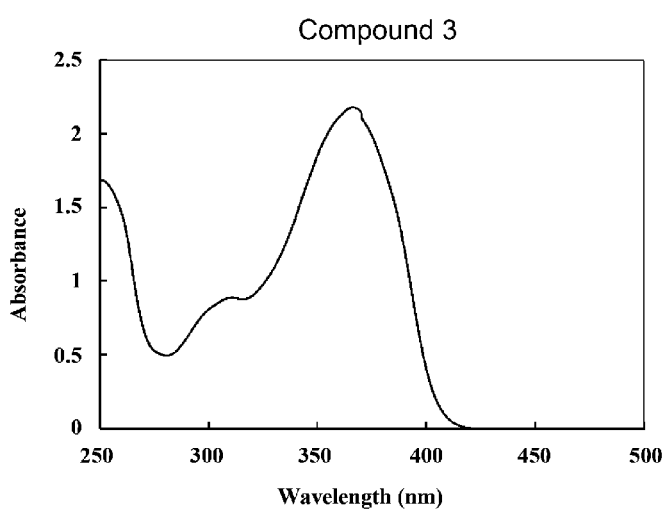
FIG. 3 is an ultraviolet-visible absorption spectrum (UV chart) of Compound 3 according to a working example of the present invention.
Figure 4:
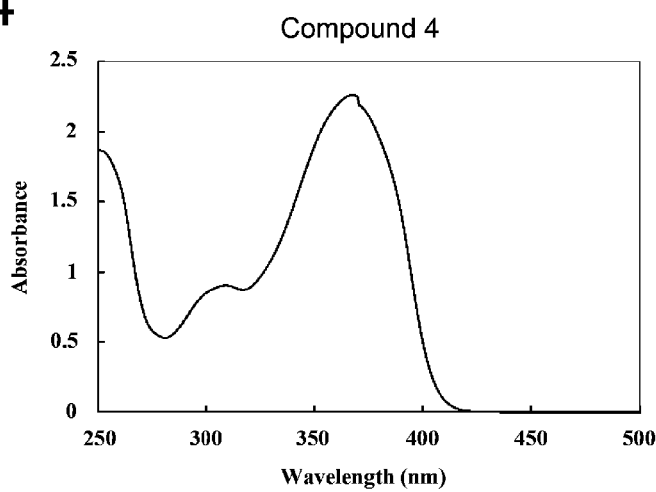
FIG. 4 is an ultraviolet-visible absorption spectrum (U chart) of Compound 4 according to a working example of the present invention.
Figure 5:
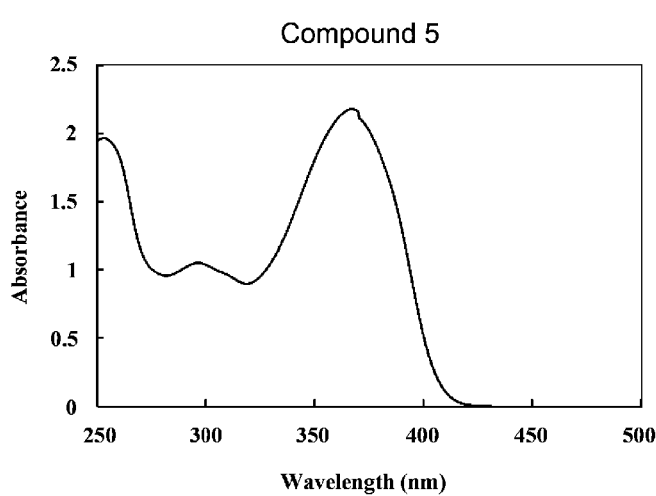
FIG. 5 is an ultraviolet-visible absorption spectrum (UV chart) of Compound 5 according to a working example of the present invention.
Figure 6:
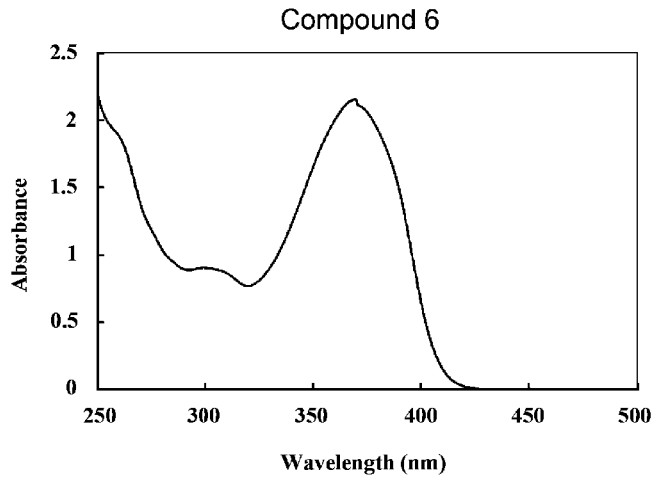
FIG. 6 is an ultraviolet-visible absorption spectrum (UV chart) of Compound 6 according to a working example of the present invention.
Figure 7:
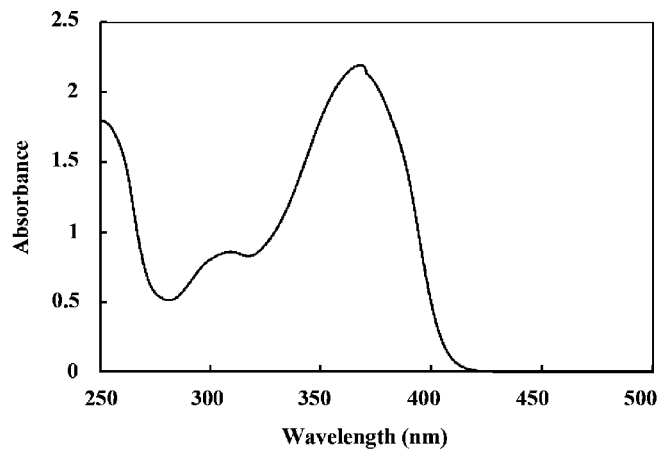
FIG. 7 is an ultraviolet-visible absorption spectrum (IN chart) of Compound 7 according to a working example of the present invention.
Figure 8:
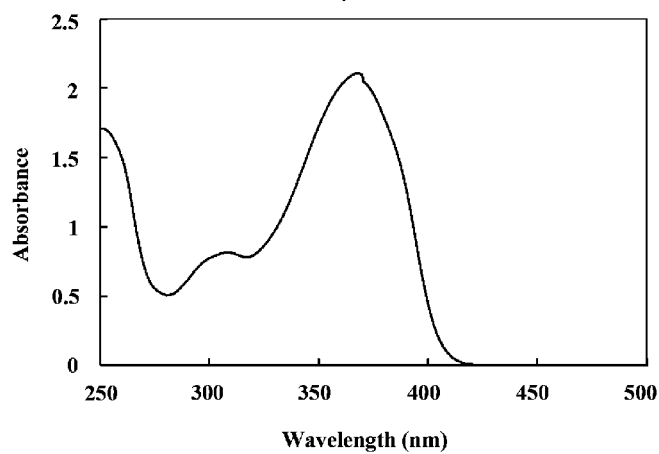
FIG. 8 is an ultraviolet-visible absorption spectrum (UV chart) of Compound 8 according to a working example of the present invention.
Figure 9:
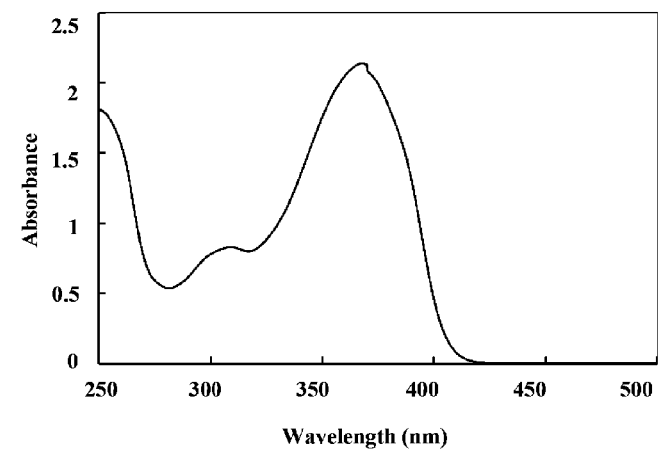
FIG. 9 is an ultraviolet-visible absorption spectrum (UV chart) of Compound 9 according to a working example of the present invention.
Figure 10:
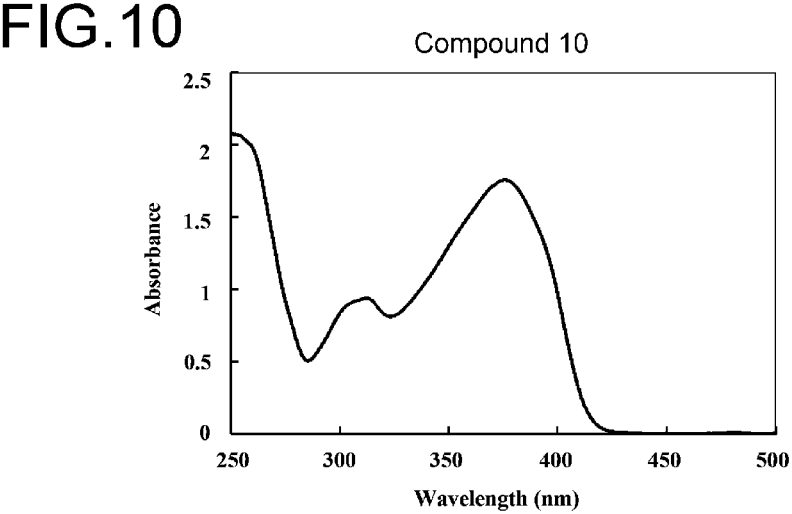
FIG. 10 is an ultraviolet-visible absorption spectrum (UV chart) of Compound 10 according to a comparative example of the present invention.
Figure 11:
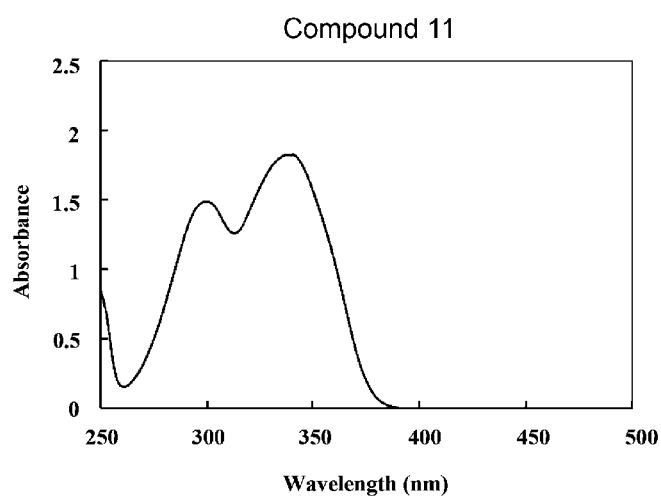
FIG. 11 is an ultraviolet-visible absorption spectrum (UV chart) of Compound 11 according to a comparative example of the present invention.
Figure 12:
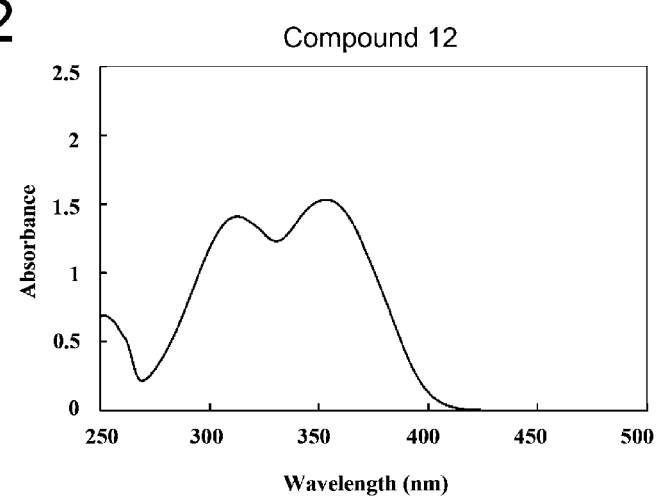
FIG. 12 is an ultraviolet-visible absorption spectrum (UV chart) of Compound 12 according to a comparative example of the present invention.

The present invention is described in detail hereunder.
(Benzotriazole Compound Represented by Formula (I))
[Substituent Group, Etc.]

In the present invention, "a monovalent or divalent group selected from an aromatic group, an unsaturated group, a nitrogen-containing group, a sulfur-containing group, an oxygen-containing group, a phosphorus-containing group, an alicyclic group and a halogen atom" includes a group(s) capable of adjusting, for example, heat resistance, refractive index, melting point, light resistance and compatibility with resins. Examples of such group(s) are as follows.

The aromatic group contains an aromatic ring(s) such as a benzene ring, a naphthalene ring and an anthracene ring, and preferably has 6 to 18, more preferably 6 to 14 carbon atoms. Examples of the monovalent aromatic group include a phenyl group, 2-methylphenyl group, 3-methylphenyl group, 4-methylphenyl group, 2,4-dimethylphenyl group, 2,5-dimethylphenyl group, 3,4-dimethylphenyl group, 3,5-dimethylphenyl group, 2,4,5-trimethylphenyl group, 2,4,6-trimethylphenyl group, 4-biphenyl group, 2-methoxyphenyl group, 3-methoxyphenyl group, 4-methoxyphenyl group, 2-ethoxyphenyl group, 3-ethoxyphenyl group, 4-ethoxyphenyl group, 2-chlorophenyl group, 2-fluorophenyl group, 4-fluorophenyl group, 2-trifluoromethylphenyl group, 4-trifluoromethylphenyl group, 1-naphthyl group, 2-naphthyl group, 1-anthracenyl group, 2-anthracenyl group and 9-anthracenyl group. Examples of the divalent aromatic group include 1,4-phenylene group, 1,3-phenylene group, 1,2-phenylene group, 1,8-naphthylene group, 2,7-naphthylene group, 2,6-naphthylene group, 1,4-naphthylene group, 1,3-naphthylene group, 9,10-anthracenylene group, 1,9-anthracenylene group, 2,7-anthracenylene group, 2,6-anthracenylene group, 1,4-anthracenylene group and 1,3-anthracenylene group.

The unsaturated group contains an unsaturated bond(s) of carbon-carbon or carbon-hetero atom, such as a carbon-carbon double bond, a carbon-carbon triple bond, a carbon-oxygen double bond (e.g. carbonyl group, aldehyde group, ester group, carboxy group, carbamate group, urea group, amide group, imide group, carbamoyl group and urethane group), a carbon-nitrogen double bond (e.g. isocyanate group) and a carbon-nitrogen triple bond (e.g. cyano group and cyanato group). It is preferred that the unsaturated group have 1 to 10, more preferably 1 to 8 carbon atoms. Examples of such unsaturated group include an acryloyl group, a methacryloyl group, a maleic acid monoester group, a styryl group, an allyl group, a vinyl group, an alkenyl group, an alkynyl group, a carbonyl group, an aldehyde group, an ester group, a carboxy group, a carbamate group, a urea group, an amide group, an imide group, a carbamoyl group, a cyano group, a cyanato group, an isocyanate group and a urethane group.

The nitrogen-containing group includes a cyano group, a nitro group or a primary to tertiary amino group, and preferably has 0 to 10 carbon atoms. Examples of such nitrogen-containing group include a cyano group, a cyanato group, an isocyanate group, a nitro group, a nitroalkyl group, an amide group, a urea group, a urethane group, an imide group, a carbodiimide group, an azo group, a pyridine group, an imidazole group, an amino group, a primary amino group, a secondary amino group, a tertiary amino group, an aminoalkyl group, 3,4,5,6-tetrahydrophthalimidylmethyl group, and 2-[6-(2H-benzotriazol-2-yl-)-4-(1,1,3,3-tetramethylbutyl)phenol-yl]-methyl group.

The sulfur-containing group includes a thiol group, a thioether group, a sulfide group, a disulfide group, a thioester group, a thioamide group, a sulfonyl group, a sulfo group, a thiocarbonyl group or a thiourea group, and preferably has 0 to 10 carbon atoms. Examples of the sulfur-containing group include a thiomethoxy group, a thioethoxy group, a thio-n-propoxy group, a thioisopropoxy group, a thio-n-butoxy group, a thio-t-butoxy group, a thiophenoxy group, a p-methylthiophenxy group, a p-methoxythiophenxy group, a thiophene group, a thiazole group, a thiol group, a sulfo group, a sulfide group, a disulfide group, a thioester group, a thioamide group, a sulfonyl group, a thiocarbonyl group, a thiourea group, a thiocarbamate group and a dithiocarbamate group.

When the oxygen-containing group includes an aromatic ring group or an alicyclic group, it is preferred that the oxygen-containing group have 6 to 12 carbon atoms. When the oxygen-containing group does not contain an aromatic ring group or an alicyclic group, it is preferred that the oxygen-containing group have 0 to 18 carbon atoms. Examples of such oxygen-containing group include a hydroxy group, a methoxy group, an ethoxy group, a propoxy group, a butoxy group, a phenoxy group, a methylphenoxy group, a dimethylphenoxy group, a naphthoxy group, a phenylmethoxy group, a phenylethoxy group, an acetoxy group, an acetyl group, an aldehyde group, a carboxy group, an other group, a carbonyl group, an ester group, an oxazole group, a morpholine group, a carbamate group, a carbamoyl group and a polyoxyethylene group.

The phosphorus-containing group includes a phosphine group, a phosphite group, a phosphonic acid group, a phosphinic acid group, a phosphoric acid group or a phosphate ester group. When the phosphorus-containing group contains an aromatic ring group or an alicyclic group, it is preferred that the phosphorus-containing group have 6 to 22 carbon atoms. When the phosphorus-containing group does not contain an aromatic ring group or an alicyclic group, it is preferred that the phosphorus-containing group have 0 to 6 carbon atoms. Examples of such phosphorus-containing group include a trimethylphosphine group, a tributylphosphine group, a tricycloheylphosphine group, a triphenylphosphine group, a tritolylphosphine group, a methylphosphite group, an ethylphosphite group, a phenylphosphite group, a phosphonic acid group, a phosphinic acid group, a phosphoric acid group and a phosphoric acid ester group.

The alicyclic group preferably has 3 to 10 carbon atoms, more preferably 3 to 9 carbon atoms. Examples of the alicyclic group includes a cyclopropyl group, a cyclobutyl group, a cyclopentyl group, a cyclohexyl group, a cycloheptyl group, a cyclooctyl group, and groups containing these groups as skeletons.

Examples of the halogen atom include a fluorine atom, a chlorine atom, a bromine atom, and an iodine atom.

The benzotriazole compound represented by the above formula (I) contains a monovalent sulfur-containing group represented by the above formula (i-1) in at least one of R to $R^9$ that are to be bonded to a benzotriazole-based skeleton.

In the formula (i-1), $R^{10}$ represents a divalent hydrocarbon group having 1 to 20, preferably 1 to 10, more preferably 1 to 5, even more preferably 1 to 3 carbon atoms, in which hydrogen atoms may be substituted with, at least one of two ends may be interrupted by, or carbon-carbon bonds may be interrupted by the monovalent or divalent group selected from the aromatic group, unsaturated group, nitrogen-containing group, sulfur-containing group, oxygen-containing group, phosphorus-containing group, alicyclic group and halogen atom.

Examples of the divalent hydrocarbon group represented by $R^{10}$ include an aliphatic hydrocarbon group, an alicyclic hydrocarbon group and an aromatic hydrocarbon group. Among these groups, an aliphatic hydrocarbon group is preferred, examples of which being a linear or branched alkylene group, a linear or branched alkenylene group, and a linear or branched alkynylene group. Specific examples include a methylene group, ethane-1,2-diyl group, propane-1,3-diyl group, 1-methylethane-1,2-diyl group, butane-1,4-diyl group, butane-1,3-diyl group, 2-methylpropane-1,3-diyl group, pane-1,5-diyl group, pentane-1,4-diyl group, hexane-1,6-diyl group, heptane-1,7-diyl group, octane-1,8-diyl group, nonane-1,9-diyl group, decane-1,10-diyl group, undecane-1,11-diyl group, dodecane-1,12-diyl group, tridecane-1,13-yl group, tetradecane-1,14-yl group, pentadecane-1,15-yl group, hexadecane-1,16-yl group, heptadecane-1,17-yl group, octadecane 1,1-yl group, nonadecane-1,19-yl group and eicosane-1,20-yl group. Among the above examples, an alkylene group is preferred, and a linear alkylene group is more preferred.

When the divalent hydrocarbon group is such that the hydrogen atoms therein are substituted with, at least one of the two ends thereof is interrupted by, or the carbon-carbon bonds therein are interrupted by the abovementioned monovalent or divalent group, there are no particular restrictions on the number of such monovalent or divalent groups. The number of such monovalent or divalent groups may, for example, be not larger than 2, or not larger than 1.

Specific examples of the aromatic group, unsaturated group, nitrogen-containing group, sulfur-containing group, oxygen-containing group, phosphorus-containing group, alicyclic group and halogen atom as the above monovalent or divalent groups, include those exemplified in the above section titled [Substituent group, etc.].

In the formula (i-1), 1 represents an integer of 0 or 1; preferably, represents 0.

In the formula (i-1), $R^{11}$ represents a divalent hydrocarbon group having 1 to 20, preferably 1 to 10, more preferably 1 to 5, even more preferably 1 to 3 carbon atoms, in which hydrogen atoms may be substituted with, at least one of two ends may be interrupted by, or carbon-carbon bonds may be interrupted by the monovalent or divalent group selected from the aromatic group, unsaturated group, nitrogen-containing group, sulfur-containing group, oxygen-containing group, phosphorus-containing group, alicyclic group and halogen atom with the proviso that each of $R^{11}$ is independent when m is not smaller than 2.

Examples of the divalent hydrocarbon group represented by $R^{11}$ include an aliphatic hydrocarbon group, an alicyclic hydrocarbon group and an aromatic hydrocarbon group. Among these groups, an aliphatic hydrocarbon group is preferred, examples of which being those listed above in the description of the divalent hydrocarbon group represented by $R^{10}$. Even among those groups, an alkylene group is preferred, and a linear alkylene group is more preferred.

When the divalent hydrocarbon group represented by $R^{11}$ is such that the hydrogen atoms therein are substituted with, at least one of the two ends thereof is interrupted by, or the carbon-carbon bonds therein are interrupted by the above-mentioned monovalent or divalent group, there are no particular restrictions on the number of such monovalent or divalent groups. The number of such monovalent or divalent groups may, for example, be not larger than 2, or not larger than 1.

Specific examples of the aromatic group, unsaturated group, nitrogen-containing group, sulfur-containing group, oxygen-containing group, phosphorus-containing group, alicyclic group and halogen atom as the above monovalent or divalent groups, include those exemplified in the above section titled [Substituent group, etc.].

In the formula (i-1), m represents an integer of 0 to 3; preferably, m represents 0 or 1; more preferably, m represents 0.

First Embodiment

Described hereunder is a first embodiment in which $R^{12}$ in the formula (i-1) is that described in the above <1>. A benzotriazole compound of the first embodiment has a favorable solubility in a monomer as a resin raw material, can be dissolved at a high concentration, and polymerizes with a favorable reactivity so as to obtain a resin member having a high molecular weight, or even a transparent resin member. Further, heat resistance is improved by introducing a nitrogen-containing group, an oxygen-containing group, a sulfur-containing group, a phosphorus-containing group or a phenylene group as $A^1$ of $R^{12}$ in the sulfur-containing group.

In the formula (i-1), $R^{12}$ represents a monovalent group expressed by the above formula (i-2). The benztriazole compound of the first embodiment is characterized by having a monovalent group represented by the formula (i-2) in a benzotriazole-based skeleton via a sulfur-containing bonding group.

In the formula (i-2), each of $R^{12a}$, $R^{12b}$ and $R^{12c}$ independently represents a hydrogen atom or a monovalent hydrocarbon group having 1 to 18 carbon atoms.

Examples of the monovalent hydrocarbon group having 1 to 18 carbon atoms include an aliphatic hydrocarbon group, an alicyclic hydrocarbon group and an aromatic hydrocarbon group. Among these groups, an aliphatic hydrocarbon group is preferred. Examples of such aliphatic hydrocarbon group include a linear or branched alkyl group, a linear or branched alkenyl group, and a linear or branched alkynyl group. Among such groups, a linear or branched alkyl group is preferred. Examples of a linear or branched alkyl group include a methyl group, ethane-1-yl group, propane-1-yl group, 1-methylethane-1-yl group, butane-1-yl group, butane-2-yl group, 2-methylpropane-1-yl group, 2-methylpropane-2-yl group, pentane-1-yl group, pentane-2-yl group, hexane-1-yl group, heptane-1-yl group, octane-1-yl group, nonane-1-yl group, decane-1-yl group, undecane-1-yl group, dodecane-1-yl group, tridecane-1-yl group, tetradecane-1-yl group, pentadecane-1-yl group, hexadecane-1-yl group, heptadecane-1-yl group and octadecane-1-yl group.

In terms of reactivity with and solubility in a monomer as a resin raw material, it is preferred that the monovalent hydrocarbon group have 1 to 13 carbon atoms, more preferably 1 to 5 carbon atoms, even more preferably 1 to 3 carbon atoms, and particularly preferably 1 carbon atom. Preferable embodiments are such that (1) $R^{12a}$, $R^{12b}$, $R^{12c}$ each represent a hydrogen atom; (2) $R^{12a}$ represents a monovalent hydrocarbon group having 1 to 3 carbon atoms, $R^{12b}$ and $R^{12c}$ each represent a hydrogen atom; (3) $R^{12a}$ represents a hydrogen atom, $R^{12b}$ represents a monovalent hydrocarbon group having 1 to 13 carbon atoms, $R^{12c}$ represents a hydrogen atom. Particularly preferable embodiments are such that in the case of (1), $R^{12a}$, $R^{12b}$, $R^{12c}$ each represent a hydrogen atom; in the case of (2), $R^{12a}$ represents a monovalent hydrocarbon group having 1 carbon atom, $R^{12b}$ and $R^{12c}$ each represent a hydrogen atom; or in the case of (3), $R^{12a}$ represents a hydrogen atom, $R^{12b}$ represents a monovalent hydrocarbon group having 1 carbon atom, $R^{12c}$ represents a hydrogen atom. In the formula (i-2), $A^1$ represents any divalent group selected from a nitrogen-containing group, an oxygen-containing group, a sulfur-containing group, a phosphorus-containing group and a phenylene group.

In the formula (i-2), as such nitrogen-containing group, oxygen-containing group, sulfur-containing group and phosphorus-containing group, there may, for example, be listed the divalent groups among the groups exemplified in the section titled [Substituent group, etc.].

Examples of a divalent nitrogen-containing group include an amide group, a urea group, a urethane group, an imide group, a carbodiimide group, an am group, a pyridine group, an imidazole group, a toluidine group, a nitroalkyl group, a secondary amino group and an aminoalkyl group. Among these groups, divalent nitrogen-containing groups having double bonds am preferred, examples of which being an amide group, a urea group, a urethane group, an imide group, a carbodiimide group, an am group, a pyridine group, an imidazole group, a toluidine group and a nitroalkyl group.

Examples of a divalent oxygen-containing group include an ether group, a carbonyl group, an ester group, an oxazole group, a carbamate group, and a carbamoyl group. Among these groups, divalent oxygen-containing groups having double bonds am preferred, examples of which being a carbonyl group, an ester group, an oxazole group, a carbamate group and a carbamoyl group.

Examples of a divalent sulfur-containing group include a thioether group, a sulfide group, a disulfide group, a thioester group, a thioamide group, a sulfonyl group, a sulfoxide group, a thiocarbonyl group, a thiourea group, a thiocarbamate group, a dithiocarbamate group, a thiophene group and a thiazole group. Among these groups, divalent sulfur-containing groups having double bonds are preferred, examples of which being a thioester group, a thioamide group, a sulfonyl group, a sulfoxide group, a thiocarbonyl group, a thiourea group, a thiocarbamate group, a dithiocarbamate group, a thiophene group and a thiazole group.

Examples of a divalent phosphorus-containing group include a phosphate ester group and a phosphonic acid ester. Among these groups, divalent phosphorus-containing groups having double bonds are preferred, examples of which being a phosphate ester group and a phosphonic acid ester.

$A^1$ is preferably a divalent group selected from an ester group, a phenylene group and an amide group. The ester group is —C(=O)O— or —OC(=O)—. The phenylene group is an o-phenylene group, m-phenylene group or p-phenylene group. The amide group is —NHC(=O)— or —C(=O)NH—. In terms of reactivity and solubility in a monomer as a resin raw material, $A^1$ is preferably an ester group, more preferably an ester group expressed by —X—O—C(=O)— where an oxygen atom is bonded to X.

Further, when $A^1$ is an ester group, a urethane group, an amide group or a urea group, a tendency similar to that of a later-described second embodiment will be exhibited, whereby introducing the nitrogen-containing group, oxygen-containing group, sulfur-containing group or phosphorus-containing group each having double bonds into the sulfur-containing group, heat resistance can be improved such that the thermal decomposition of the compound will be suppressed, and that deteriorations in ultraviolet absorption ability and outer appearance will be suppressed as well. That is, a favorable solubility in a monomer as a resin raw material is exhibited, dissolution at a high concentration is thus possible, and polymerization can take place with a favorable reactivity, thereby obtaining a resin member having a high molecular weight or even a transparent resin member, and achieving a superior beat resistance.

In the formula (i-2), X may be a divalent group selected from —$X^1$—, —$X^2$—, —$X^1$—$(Y)_p$—$X^2$— and —$X^2$—$(Y)_p$—$X^1$—. Specifically, $X^1$ represent a divalent group selected from —$X^1$—, —$X^2$—, —$X^1$—$(Y)_p$—$X^2$—, —$X^2$—$(Y)_p$—$X^1$— and —$X^2$—$(Y)_p$—$X^2$—. Here, $X^1$ represents a divalent hydrocarbon group having 1 to 20 carbon atoms, in which hydrogen atoms may be substituted with, at least one of two ends may be interrupted by, or carbon-carbon bonds may be interrupted by the monovalent or divalent group selected from the aromatic group, unsaturated group, nitrogen-containing group, sulfur-containing group, oxygen-containing group, phosphorus-containing group, alicyclic group and halogen atom; $X^2$ represents a divalent aromatic group; Y represents a hetero atom; p represents an integer of 0 or 1.

Examples of the divalent hydrocarbon group represented by $X^1$ include an aliphatic hydrocarbon group, an alicyclic hydrocarbon group and an aromatic hydrocarbon group. Among these groups, an aliphatic hydrocarbon group is preferred, examples of which being those listed above as the examples of the divalent hydrocarbon group represented by $R^{10}$. Among such groups, an alkylene group is preferred, and a linear alkylene group is more preferred.

When the divalent hydrocarbon group represented by $X^1$ is such that the hydrogen atoms therein are substituted with, at least one of the two ends thereof is interrupted by, or the carbon-carbon bonds therein are interrupted by the above-mentioned monovalent or divalent group, there are no particular restrictions on the number of such monovalent or divalent groups. The number of such monovalent or divalent groups may, for example, be not larger than 2, or not larger than 1.

Specific examples of the aromatic group, unsaturated group, nitrogen-containing group, sulfur-containing group, oxygen-containing group, phosphorus-containing group, alicyclic group and halogen atom as the above monovalent or divalent groups, include those exemplified in the above section titled [Substituent group, etc.].

The divalent aromatic group represented by $X^2$ contains an aromatic ring such as a benzene ring, a naphthalene ring or an anthracene ring, and preferably has 6 to 1, more preferably 6 to 14 carbon atoms. Examples of such divalent aromatic group include those exemplified in the above section tided [Substituent group, etc.].

There are no particular restrictions on the hetero atom represented by Y, examples of which being an oxygen atom and a sulfur atom.

In X of the formula (i-2), it is preferred that $X^1$ represent an unsubstituted and uninterrupted divalent hydrocarbon group having 1 to 20 carbon atoms, $X^2$ represent a divalent aromatic group, and Y represent an oxygen atom or a sulfur atom.

In X of the formula (i-2), it is more preferred that $X^1$ represent an unsubstituted and uninterrupted divalent alkylene group —$(CH_2)_n$— (n represents an integer of 1 to 20) having 1 to 20 carbon atoms. When X is —$X^1$—, it is preferred that X represent an alkylene group —$(CH_2)_n$— (n represents an integer of 1 to 20).

When $X^1$ and X are alkylene groups —$(CH_2)_n$—, it is preferred that n be not smaller than 2, more preferably not smaller than 3, in terms of achieving a solubility in a monomer as a resin raw material and the transparency of the resin member, and especially in terms of the capability of performing polymerization at a higher molecular weight due to a favorable reactivity with a monomer as a resin raw material. Although there are no particular restrictions on the upper limit of n, it is preferred that n be not larger than 10, more preferably not larger than 6, in terms of solubility in a monomer as a resin raw material, transparency of the resin member, and especially reactivity with a monomer as a resin raw material. That is, it is preferred that n be 2 to 10, more preferably 3 to 10, even more preferably 2 to 6, and particularly preferably 3 to 6.

In X of the above formula (i-2), it is more preferred that $X^2$ be a divalent phenylene group. In a case where $X^2$ represents a divalent phenylene group, when $X^2$ in the above formula (i-2) is —$X^2$—, X is a phenylene group. In the case where $X^2$ represents a divalent phenylene group, when X in the above formula (i-2) is —$X^1$—$(Y)_p$—$X^2$— or —$X^2$—$(Y)_p$—$X^1$—, $X^2(Y)$—$X^1$— is preferred, $X^1$ is an alkylene group —$(CH_2)_n$— (n represents an integer of 1 to 20), and Y is more preferably an oxygen atom. In such case, n in the alkylene group —$(CH_2)_n$— is preferably 2 to 10, more preferably 3 to 10, even more preferably 2 to 6, and particularly preferably 3 to 6.

Particularly preferable examples of the monovalent group represented by the formula (i-1) include groups represented by the following formulae (i-1-1), (i-1-2) and (i-1-3) in which l and m are 0, and $R^{12c}$ is a hydrogen atom.

[Chemical formula 5]

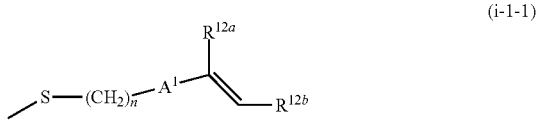

(i-1-1)

(In the above formula, $R^{12a}$, $R^{12b}$, $A^1$ and n are defined as above.)

[Chemical formula 6]

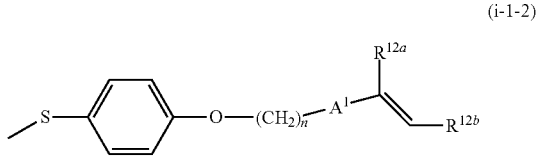

(i-1-2)

(In the above formula, $R^{12a}$, $R^{12b}$, $A^1$ and n are defined as above.)

[Chemical formula 7]

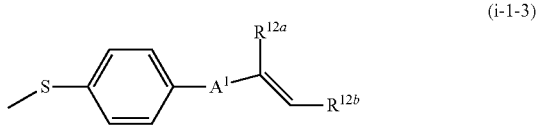

(i-1-3)

(In the above formula, $R^{12a}$, $R^{12b}$, $A^1$ are defined as above.)

According to the benzotriazole compound of the first embodiment, a favorable solubility in a monomer as a resin raw material is exhibited, dissolution at a high concentration is thus possible, and polymerization can take place with a favorable reactivity, thereby obtaining a resin member having a high molecular weight, or even a transparent resin member. Further, heat resistance is improved by introducing a nitrogen-containing group, an oxygen-containing group, a sulfur-containing group, a phosphorus-containing group or a phenylene group as $A^1$ of $R^{12}$ in the sulfur-containing group. The benzotriazole compound of the first embodiment has, as a reactive functional group, the monovalent group represented by the formula (i-2) in the benzotriazole-based skeleton via the sulfur-containing bonding group. In a case where a resin member is then obtained by reaction, copolymerization and a molding process, using an organic or inorganic compound, particularly a monomer as a resin raw material or a resin each containing a functional group(s) capable of reacting with the vinyl group in the above reactive functional group, the benzotriazole compound of the first embodiment copolymerizes or reacts with the target compound, particularly a monomer as a ream raw material or a functional group(s) in a ream such that the benzotriazole compound of the first embodiment can be immobilized on a matrix, and retain an ultraviolet absorption ability for a long period without bleeding out or eluting. In addition, by selecting a monomer and a resin, there can be obtained a matrix and resin member retaining transparency.

The compound of the first embodiment is such that the sulfur-containing group and the functional group represented by the formula (i-2) have been introduced into the benzotriazole-based ultraviolet absorption skeleton. Thus, the compound has a favorable reactivity with a monomer and resin as well as a favorable compatibility with a monomer, has a high molecular weight, and is also capable of imparting a high ultraviolet absorption ability to a resin compact or the like while allowing such compact or the like to maintain a high transparency if necessary.

Second Embodiment

Described hereunder is a second embodiment in which $R^{12}$ in the formula (i-1) is that described in the above <2>. A benzotriazole compound of the second embodiment is such that by introducing a sulfur-containing group, particularly by introducing a nitrogen-containing group, an oxygen-containing group, a sulfur-containing group or a phosphorus-containing group as $A^2$ of $R^{12}$ in the sulfur-containing group, beat resistance can be improved such that the thermal decomposition of the compound will be suppressed, and that deteriorations in ultraviolet absorption ability and outer appearance will be suppressed as well. In particular, since the compound cannot easily undergo thermal decomposition during heat molding and processing, it can be employed as an ultraviolet absorber even for a resin requiring a higher molding and processing temperature.

In the formula (i-1), $R^{12}$ represents a monovalent group expressed by the above formula (i-3). The benzotriazole compound of the second embodiment is characterized by having the monovalent group represented by this formula (i-3) in a benzotriazole-based skeleton via a sulfur-containing bonding group.

In the formula (i-3), $A^2$ represents a divalent group selected from a nitrogen-containing group, an oxygen-containing group, a sulfur-containing group and a phosphorus-containing group, examples of which being the divalent groups among the groups exemplified in the section tided [Substituent group, etc.].

Examples of a divalent nitrogen-containing group include an amide group, a urea group, a urethane group, an imide group, a carbodiimide group, an azo group, a pyridine group, an imidazole group, a toluidine group, a nitroalkyl group, a secondary amino group and an aminoalkyl group. Among these groups, divalent nitrogen-containing groups having double bonds are preferred, examples of which being an amide group, a urea group, a urethane group, an imide group, a carbodiimide group, an azo group, a pyridine group, an imidazole group, a toluidine group and a nitroalkyl group.

Examples of a divalent oxygen-containing group include an ether group, a carbonyl group, an ester group, an oxazole group, a carbamate group, and a carbamoyl group. Among these groups, divalent oxygen-containing groups having double bonds are preferred, examples of which being a carbonyl group, an ester group, an oxazole group, a carbamate group and a carbamoyl group.

Examples of a divalent sulfur-containing group include a thioether group, a sulfide group, a disulfide group, a thioester group, a thioamide group, a sulfonyl group, a sulfoxide group, a thiocarbonyl group, a thiourea group, a thiocarbamate group, a dithiocarbamate group, a thiophene group and a thiazole group. Among these groups, divalent sulfur-containing groups having double bonds are preferred, examples of which being a thioester group, a thioamide group, a sulfonyl group, a sulfoxide group, a thiocarbonyl group, a thiourea group, a thiocarbanilate group, a dithiocarbamate group, a thiophene group and a thiazole group.

Examples of a divalent phosphorus-containing group include a phosphate ester group and a phosphonic acid ester. Among these groups, divalent phosphorus-containing groups having double bonds are preferred, examples of which being a phosphate ester group and a phosphonic acid ester.

In this way, by introducing $A^2$ into $R^{12}$, heat resistance can be improved such that the thermal decomposition of the compound will be suppressed, and that deteriorations in ultraviolet absorption ability and outer appearance will be suppressed as well. Further, in particular, since the compound cannot be easily subjected to thermal decomposition during heat molding and heat processing, it can be employed as an ultraviolet absorber even for a resin requiring a higher molding and processing temperature.

In the formula (i-3), $X^a$ represents a divalent group selected from $—X^{a1}—$, $—X^{a2}—$, $—X^{a1}—(Y^a)_q—X^{a2}—$, $—X^{a2}—(Y^a)_q—X^{a1}—$ and $—X^{a2}—(Y^a)_q—X^{a2}—$. Here, $X^{a1}$ represents a divalent hydrocarbon group having 1 to 20 carbon atoms, in which hydrogen atoms may be substituted, at least one of two ends may be interrupted, or carbon-carbon bonds may be interrupted by the monovalent or divalent group selected from the aromatic group, unsaturated group, nitrogen-containing group, sulfur-containing group, oxygen-containing group, phosphorus-containing group, alicylic group and halogen atom; $X^{a2}$ represents a divalent aromatic group; $Y^a$ represents a hetero atom; q represents an integer of 0 or 1. $X^b$ represents a monovalent group selected from $—X^{b1}$, $—X^{b2}$, $—X^{a1}—(Y^b)_r—X^{b2}$, $—X^{a2}—(Y^b)_r—X^{b1}$ and $—X^{a2}—(Y^b)_r—X^{b2}$. Here, $X^{b1}$ represents a divalent hydrocarbon group having 1 to 20 carbon atoms, in which hydrogen atoms may be substituted, a base end may be interrupted, or carbon-carbon bonds may be interrupted by the monovalent or divalent group selected from the aromatic group, unsaturated group, nitrogen-containing group, sulfur-containing group, oxygen-containing group, phosphorus-containing group, alicyclic group and halogen atom; $X^{b2}$ represents a monovalent aromatic group; $Y^b$ represents a hetero atom; r represents an integer of 0 or 1. $X^{a1}$ and $X^{a2}$ are defined as above, but are each independent from those listed in the description of $X^a$.

Examples of the divalent hydrocarbon group represented by $X^{a1}$ include an aliphatic hydrocarbon group, an alicyclic hydrocarbon group and an aromatic hydrocarbon group. Among these groups, an aliphatic hydrocarbon group is preferred, examples of which being those listed above as the examples of the divalent hydrocarbon group represented by $R^{10}$. Among such groups, an alkylene group is preferred, and a linear alkylene group is more preferred.

When the divalent hydrocarbon group represented by $X^{a1}$ is such that the hydrogen atoms therein are substituted with, at least one of the two ends thereof is interrupted by, or the carbon-carbon bonds therein are interrupted by the abovementioned monovalent or divalent group, there are no particular restrictions on the number of such monovalent or divalent groups. The number of such monovalent or divalent groups may, for example, be not larger than 2, or not larger than 1. Specific examples of the aromatic group, unsaturated group, nitrogen-containing group, sulfur-containing group, oxygen-containing group, phosphorus-containing group, alicyclic group and halogen atom as the above monovalent or divalent groups, include those exemplified in the above section titled [Substituent group, etc.].

The divalent aromatic group represented by $X^{a2}$ contains an aromatic ring such as a benzene ring, a naphthalene ring or an anthracene ring, and preferably has 6 to 18, more preferably 6 to 14 carbon atoms. Examples of such divalent aromatic group include those exemplified in the above section tided [Substituent group, etc.].

Examples of the monovalent hydrocarbon group represented by $X^{b1}$ include an aliphatic hydrocarbon group, an alicyclic hydrocarbon group and an aromatic hydrocarbon group. Among these groups, an aliphatic hydrocarbon group is preferred, examples of which being a linear or branched alkyl group, a linear or branched alkenyl group and a linear or branched alkynyl group, among which a liner alkyl group is preferred. Examples of the alkyl group include a methyl group, ethane-1-yl group, propan-1-yl group, 1-methylethane-1-yl group, butane-1-yl group, butane-2-yl group, 2-methylpropane-1-yl group, 2-methylpropane-2-yl group, pentane-1-yl group, pentane-2-yl group, 2-methylbutane-1-yl group, hexane-1-yl group, 3-methylpentane-1-yl group, 2-methylpentane-1-yl group, heptane-1-yl group, 2-methylhexane-yl group, 3-methylhexane-yl group, 3-ethylpentane-1-yl group, octane-1-yl group, 2-ethylhexane-1-yl group, 3-ethylhexane-1-yl group, 2-methylheptane-1-yl group, 3-methylheptane-1-yl group, 4-methylheptane-1-yl group, 1,1,3,3-tetramethylbutyl-1-yl group, nonane-1-yl group, 3-ethylheptane-1-yl group, 4-ethylheptane-1-yl group, 2-methyloctane-1-yl group, 3-methyloctane-1-yl group, 4-methyloctane-1-yl group, decane-1-yl group, 4-propylheptane-1-yl group, 3-ethyloctane-1-yl group, 4-ethyloctane-1-yl group, undecane-1-yl group, dodecane-1-yl group, 2-methylundecane-1-yl group, 2-ethyldecane-1-yl group, tridecan-1-yl group, tetradeca-1-yl group, pentadecan-1-yl group, hexadecane-1-yl group, heptadecan-1-yl group, octadecan-1-yl group, nonadecane-1-yl group and eicosane-1-yl group. Examples of the alkenyl group include an ethene-1-yl group, propene-1-yl group, butene-1-yl group, penten-1-yl group, 2-methyl-1-butene-1-yl group, 3-methyl-1-butene-1-yl group, 2-methyl-2-butene-1-yl group, heptene-1-yl group, octene-1-yl group, nonene-1-yl group, decene-1-yl group, undecene-1-yl group, dodecene-1-yl group, trideca-1-yl group, tetradecene-1-yl group, pentadecene-1-yl group, hexadecene-1-yl group, octadecene-1-yl group, nonadecene-1-yl group and eicosene-1-yl group. Examples of the alkynyl group include an ethyne-1-yl group, propyne-1-yl group, butyne-1-yl group, pentyne-1-yl group, 2-methyl-1-butyne-1-yl group, 3-methyl-1-butyne-1-yl group, 2-methyl-2-butyne-1-yl group, hexyne-1-yl group, heptyne-1-yl group, octyne-1-yl group, nonyne-1-yl group, decyne-1-yl group, undecyne-1-yl group, dodecyne-1-yl group, tridecyne-1-yl group, tetradecyne-1-yl group, pentadecyne-1-yl group, hexadecyne-1-yl group, octadecyne-1-yl group, nonadecyne-1-yl group and eicosyne-1-yl group. Further, examples of the monovalent hydrocarbon group represented by $X^{b1}$ include $—(R^{12a})=(R^{12c})$ which is a monovalent group bonded to $A^1$ in the above formula (i-2).

When the monovalent hydrocarbon group represented by $X^{b1}$ is such that the hydrogen atoms therein are substituted with, the base end thereof is interrupted by, or the carbon-carbon bonds therein are interrupted by the abovementioned monovalent or divalent group, there are no particular restrictions on the number of such monovalent or divalent groups. The number of such monovalent or divalent groups may, for example, be not larger than 2, or not larger than 1. Specific examples of the aromatic group, unsaturated group, nitrogen-containing group, sulfur-containing group, oxygen-containing group, phosphorus-containing group, alicyclic group and halogen atom as the above monovalent or divalent groups, include those exemplified in the above section titled [Substituent group, etc.]. The monovalent aromatic group represented by $X^{b2}$ contains an aromatic ring such as a benzene ring, a naphthalene ring or an anthracene ring, and preferably has 6 to 18, more preferably 6 to 14 carbon atoms. Examples of such monovalent aromatic group include those exemplified in the above section titled [Substituent group, etc.].

There are no particular restrictions on the hetero atoms represented by $Y^a$ and $Y^b$, examples of which being an oxygen atom and a sulfur atom.

In $X^a$ of the formula (i-3), it is preferred that $X^{a1}$ represents an unsubstituted and uninterrupted divalent hydrocarbon group having 1 to 20 carbon atoms, $X^{a2}$ represents a divalent aromatic group, and $Y^a$ represents an oxygen atom or a sulfur atom. In $X^b$ of the formula (i-3), it is preferred that $X^{b1}$ represents an unsubstituted and uninterrupted monovalent hydrocarbon group having 1 to 20 carbon atoms, $X^{b2}$ represents a monovalent aromatic group, $Y^b$ represents an oxygen atom or a sulfur atom, $X^{a1}$ represents an unsubstituted and uninterrupted divalent hydrocarbon group having 1 to 20 carbon atoms, and $X^{a2}$ represents a divalent aromatic group ($X^{a1}$ and $X^{a2}$ are each independent from those listed in the description of $X^a$.).

In $X^a$ of the formula (i-3), it is more preferred that $X^{a1}$ represents an unsubstituted and uninterrupted divalent alkylene group —$(CH_2)_n$— (n represents an integer of 1 to 20) having 1 to 20 carbon atoms. When $X^a$ is —$X^{a1}$—, it is preferred that $X^a$ represents an alkylene group —$(CH_2)_n$— (n represents an integer of 1 to 20).

When $X^a$ is an alkylene group —$(CH_2)_n$—, it is preferred that n be not smaller than 2, more preferably not smaller than 3, in terms of further improving heat resistance. Although there are no particular restrictions on the upper limit of n, it is preferred that n be not larger than 10, more preferably not larger than 6. That is, it is preferred that n be 2 to 10, more preferably 2 to 6, and particularly preferably 3 to 6.

In $X^a$ of the formula (i-3), it is preferred that the divalent aromatic group $X^{a2}$ be contained in terms of further improving heat resistance. In such case, $X^a$ is any divalent group selected from —$X^{a2}$—, —$X^{a1}$—$(Y^a)_q$—$X^{a2}$— and —$X^{a2}$—$(Y^a)_q$—$X^{a1}$— and —$X^{a2}$$(Y^a)_q$—$X^{a2}$—.

In $X^a$ of the formula (i-3), q is preferably 0.

In $X^b$ of the formula (i-3), it is preferred that $X^{a2}$ or $X^{b2}$ as an aromatic group be contained in terms of further improving heat resistance, and any one of —$X^{b2}$, —$X^{a1}$—$(Y^b)_r$—$X^{b2}$, —$X^{a2}$—$(Y^b)_r$—$X^{b1}$, —$X^{a2}$—$(Y^b)_r$—$X^{b2}$ is preferred. When $X^a$ and $X^b$ in the formula (i-3) represent alkyl groups, and $A^2$ in the formula (i-3) represents an ester group, the number of the carbon atoms thereof is preferably not smaller than 1, more preferably not smaller than 6, and even more preferably not smaller than 14.

In $X^b$ of the formula (i-3), for example, $X^{b1}$ may be an unsubstituted and uninterrupted monovalent alkyl group having 1 to 20 carbon atoms, $X^{b2}$ may be a monovalent aromatic group, $Y^b$ may be an oxygen atom or a sulfur atom, $X^{a1}$ may be an unsubstituted and uninterrupted divalent alkyl group having 1 to 20 carbon atoms, and $X^{a2}$ may be a divalent aromatic group. As another example, $X^b$ may be —$(R^{12a})$=$(R^{12b})(R^{12c})$ which is a monovalent group bonded to $A^1$ in the formula (i-2), so that a superior beat resistance can be achieved, and as is the case with the first embodiment, the compound can exhibit a favorable solubility in a monomer as a resin raw material, be dissolved at a high concentration, and polymerize with a favorable reactivity so as to obtain a resin member having a high molecular weight, or even a transparent resin member.

In $X^b$ of the formula (i-3), r is preferably 0.

Further, in terms of improving heat resistance, it is preferred that $A^2$ in the formula (i-3) be an amide group, an ester group, a urethane group or a urea group. The amide group is —NHC(=O)— or —C(=O)NH—; the ester group is —C(=O)— or —OC(=O)—; the urethane group is —NHC(=O)O— or —OC(=O)NH—; the urea group is —NHC(=O)NH—. Among these groups, an ester group and an amide group are more preferred, and an amide group is particularly preferred. Meanwhile, as for $X^a$ and $X^b$ in the formula (i-3), when $X^a$ and $X^b$ are an aliphatic hydrocarbon group (alkyl group, alkylene group) and an aromatic group, or when both of them are aliphatic hydrocarbon groups (alkyl group, alkylene group), the total number of the carbon atoms in $X^a$ and $X^b$ is preferably not smaller than 2, more preferably not smaller than 5, even more preferably not smaller than 10, and particularly preferably not smaller than 18. With regard to a combination of $X^a$ and $X^b$, more preferred is a compound in which both $X^a$ and $X^b$ are aromatic groups. When reacting, mixing or kneading an ultraviolet absorber with an organic substance such as a resin or an inorganic substance while performing heating, or when processing or molding an ultraviolet absorber-containing resin member by heating, decomposition will take place if the thermal decomposition temperature of the ultraviolet absorber is low, which makes it impossible for the ultraviolet absorption effect to be fully exhibited, and thus leads to the contamination of the device(s) used. That is, in the case of a transparent resin member, a higher thermal decomposition temperature is desired for avoiding a loss in transparency. As for the benzotriazole compound of the first embodiment, heat resistance is improved by introducing the thioether group represented by the above formula (i-1). A 5% weight reduction temperature of the benzotriazole compound of the first embodiment is preferably not lower than 255° C., more preferably not lower than 270° C., even more preferably not lower than 280° C., particularly preferably not lower than 290° C., further particularly preferably not lower than 300° C., and especially preferably not lower than 310° C. Since the 5% weight reduction temperature is higher than 100 to 250° C. which is the softening temperature(s) of a general resin ("Easily understandable plastics", supervised by the Japan Plastics Industry Federation, and published by NIPPON JITSUGYO PUBLISHING), the compound can be applied to, for example, a thermosetting resin or thermoplastic resin having a molding and processing temperature of 100 to 200° C., or even to a thermoplastic resin requiring a molding and processing temperature higher than 200 to 250° C.

As for the benzotriazole compounds according to the first and second embodiments of the present invention, in formula (I), at least one of $R^1$ to $R^9$ is the monovalent sulfur-containing group represented by the formula (i-1). Here, in terms of for example, an ease in practical synthesis, absorption characteristics, cost and heat resistance; or in terms of the capability of expressing a high ultraviolet absorption ability at a high concentration of the compound added, as a result of suppressing the white turbidity of a resin member to which the compound of the present invention has been added, which is due to the compound's favorable compatibility with a monomer as a resin raw material, it is preferred that one to two of $R^1$ to $R^9$ represent the monovalent sulfur-containing group(s) represented by the formula (i-1), more preferably, one of $R^1$ to $R^9$ represents the monovalent sulfur-containing group represented by the formula (i-1). There are no particular restrictions on the position of the monovalent sulfur-containing group represented by the formula (i-1) in the formula (I). The monovalent sulfur-containing group represented by the formula (i-1) is preferably positioned at any one of $R^6$ to $R^9$ in the formula (I), and the positions of $R^6$ and $R^9$ are more preferred.

In the formula (I), when $R^1$ to $R^9$ are groups other than the monovalent sulfur-containing group represented by the formula (i-1), they each represent a monovalent group selected from a hydrogen atom, a hydrocarbon group having 1 to 10 carbon atoms, an aromatic group, an unsaturated group, a nitrogen-containing group, sulfur-containing group, an oxygen-containing group, a phosphorus-containing group, an alicyclic group and a halogen atom.

When $R^1$ to $R^9$ are monovalent hydrocarbon groups, examples of such monovalent hydrocarbon groups include an aliphatic hydrocarbon group, an alicyclic hydrocarbon group and an aromatic hydrocarbon group. Among these groups, an aliphatic hydrocarbon group is preferred, examples of which being a linear or branched alkyl group, a linear or branched alkenyl group, and a linear or branched alkynyl group. Specific examples thereof include a methyl group, ethane-1-yl group, propane-1-yl group, 1-methylethane-1-yl group, butane-1-yl group, butane-2-yl group, 2-methylpropane-1-yl group, 2-methylpropane-2-yl group, pentane-1-yl group, pentane-2-yl group, 2-methylbutane-1-yl group, hexane-1-yl group, 2-methylpentane-1-yl group, 3-methylpentane-1-yl group, heptane-1-yl group, 3-ethylpentane-1-yl group, 2-methylhexane-yl group, 3-methylhexane-yl group, octane-1-yl group, 2-methylheptane-1-yl group, 3-methylheptane-1-yl group, 4-methylheptane-1-yl group, 2-ethylhexane-1-yl group, 3-ethylhexane-1-yl group, 1,1,3,3-tetramethylbutyl nonane-1-yl group, 3-ethylheptane-1-yl group, 4-ethylheptane-1-yl group, 2-methyloctane-1-yl group, 3-methyloctane-1-yl group, 4-methyloctane-1-yl group, decane-1-yl group, 4-propylheptane-1-yl group, 3-ethyloctane-1-yl group, 4-ethyloctane-1-yl group, undecane-1-yl group, dodecane-1-yl group, 2-methylundecane-1-yl group, 2-ethyldecane-1-yl group, tridecane-1-yl group, tetradecan-1-yl group, pentadecan-yl group, hexadecane-1-yl group, heptadecane-1-yl group and octadecane-1-yl group. Among these groups, linear or branched alkyl groups having 1 to 8 carbon atoms are preferred, and linear or branched alkyl groups having 1 to 4 carbon atoms are more preferred.

When $R^1$ to $R^9$ am monovalent groups selected from an aromatic group, an unsaturated group, a sulfur-containing group, an oxygen-containing group, a phosphorus-containing group, an alicyclic group and a halogen atom, specific examples thereof include those exemplified in the above section titled [Substituent group, etc.].

In the formula (I), when the monovalent sulfur-containing group represented by the formula (i-1) is contained in $R^9$ at the 5-position, as a group other than the monovalent sulfur-containing group represented by the formula (i-1), it is preferred that $R^6$, $R^7$ and $R^8$ am all hydrogen atoms. Further, preferable examples of combinations of $R^1$, $R^2$, $R^3$, $R^4$ and $R^8$ are as follows.

[1] These include one or more substituent groups selected from: a hydrocarbon group having 1 to 18 carbon atoms (including hydrocarbon groups having 2 to 18 carbon atoms, such as an alkenyl group and an alkynyl group); a hydroxy group; an aromatic group having 6 to 18 carbon atoms; an ether group having 1 to 18 carbon atoms; an alkoxy group having 1 to 18 carbon atoms; an ester group having 1 to 18 carbon atoms; a (meth) acryloyloxy group and/or polyoxyethylene group having 1 to 20 carbon atoms; or a hydrocarbon group having 1 to 18 carbon atoms, in which hydrogen atoms may be substituted, a base end may be interrupted, or carbon-carbon bonds may be interrupted by the above-mentioned substituent groups.

[2] In [1], the substituent groups are at least one selected from a hydrocarbon group having 1 to 10 carbon atoms, and a hydroxy group.

[3] In [2], the substituent groups are at least one selected from a hydrocarbon group having 1 to 8 carbon atoms, and a hydroxy group.

[4] In any of [1] to [3], the hydrocarbon groups as the substituent groups are linear or branched alkyl groups.

[5] In [4], the substituent groups are at least one selected from a methyl group, a t-butyl group, and a hydroxy group.

[6] In [5], the substituent groups are at least one selected from a methyl group, a t-butyl group, and a hydroxy group, provided that the number of hydroxy groups is not larger than 1.

[7] In any of [1] to [6], the number of the substituent groups is 2 to 4.

[8] In any of [1] to [7], the substituent groups are positioned at any of $R^1$ to $R^4$, and the rest of $R^1$ to $R^5$ are hydrogen atoms.

[9] In any of [1] to [8], the substituent groups are positioned at any of $R^1$, $R^2$ and $R^4$, and the rest of $R^1$ to $R^5$ m hydrogen toms.

[10] In [9], $R^1$ is a hydroxy group, $R^2$ is a t-butyl group, $R^4$ is a methyl group, and $R^3$ and $R^5$ am hydrogen toms.

In addition to a resin transparency due to the compound's compatibility, a transparent resin member containing the benzotriazole compound of the present invention that is represented by the formula (I) is capable of absorbing wavelengths in a long-wavelength region while suppressing yellowing, due to the characteristics of peaks of ultraviolet absorption. Specifically, ultraviolet rays in the vicinity of 360 to 400 nm as longer wavelengths can be sharply cut even in the UV-A region without cutting 400 to 500 m (visible range) due to the characteristics of the ultraviolet absorption ability. Therefore, there can be obtained a resin member having an excellent appearance with yellow coloration being suppressed. That is, due to the optical characteristics thereof lights in a wavelength range of 250 to 400 nm can be sufficiently absorbed. Moreover, yellowing of the resin member can be suppressed due to the fact that the compound has a high ultraviolet absorption effect (molar absorption coefficient), lights of such wavelengths can be sufficiently absorbed even when a small amount of the compound has been added, and the slope of its absorption peak at 350 to 390 nm in a chloroform solution is larger than that of the conventional ultraviolet absorber. In the formula (i-3), a compound in which an aromatic group has been introduced into $X^a$ has a higher absorption peak in a region of 250 to 320 nm, and by further introducing an aromatic group into $X^b$ and/or a nitrogen-containing group such as an am group and a urea group (in particular, urea group) into $A^2$, the absorption peak thereof will become even higher so that ultraviolet rays can be absorbed in a wide range of low to long wavelengths. In order to obtain a resin member capable of absorbing harmful lights in a wide wavelength range up to 400 nm, suppressing the absorption of wavelength lights in the vicinity of 400 nm or higher which is a cause of yellowing, and having an excellent appearance with yellowing being suppressed, it is preferred that the absorption peak of lights in a 100 µM chloroform solution be 350 to 390 n, more preferably 360 to 380 nm, and particularly preferably 360 to 375 nm. Further, it is preferred that the absorption peak(s) in these wavelength regions be the maximum absorption wavelength ($\lambda_{max}$). Furthermore, as for such wavelength peak, in order to suppress the absorption of lights of wavelengths longer than around 400 nm, the absorption spectrum on the long wavelength side is preferably sharp (i.e. the absolute value of the slope is larger) and the slope of the absorption peak on the long wavelength side (the absolute value of the slope of the straight line connecting the absorption peak and the peak end of the absorption spectrum on the long wavelength side) is preferably not smaller than 0.025, more preferably not smaller than 0.030, even more preferably not smaller than 0.040, particularly preferably not smaller than 0.042, and especially preferably not smaller than 0.043. Furthermore, in order for absorption to efficiently take place at a small amount, the molar extinction coefficient (maximum molar extinction coefficient: $\epsilon\lambda_{max}$) of the absorption peak at the above range of 350 to 390 nm is preferably not smaller than 17,000 L/(mol·cm), more preferably not smaller than 18,000 L/(mol·cm), even more preferably not smaller than 20,000 L/(mol·cm), and particularly preferably not smaller than 21,000 L/(mol·cm).

There are no particular limitations when producing the benzotriazole compound represented by the formula (I); the following disclosures of the working examples and known techniques can be incorporated by reference.

(Composition Containing the Benzotriazole Compound of the Invention)

The use of the benzotriazole compound of the present invention is not particularly limited; the application thereof includes a composition to which the benzotriazole compound of the invention has been added as an ultraviolet absorber.

In the present invention, the term "composition" includes a composition to which the benzotriazole compound of the present invention has been added regardless of the composition's properties such as a solid state, a fluid state, a gel state or a sol state; and includes not only a member but also a raw material for producing such member. In the present invention, though not particularly limited, the term "member" includes, for example, a member used in the application exemplified later, and includes an object having an arbitrary shape. Further, a composition to which the benzotriazole compound of the present invention has been added includes a composition in which the benzotriazole compound of the invention has reacted after being added thereto; and includes, for example, a polymer of the present invention that is described later.

Examples of the material of the composition to which the benzotriazole compound of the present invention has been added, include an organic material and an inorganic material. The benzotriazole compound of the present invention has a high affinity, a high compatibility and a high reactivity with various organic materials and inorganic materials. By mixing, dissolving, dispersing and reacting the benzotriazole compound of the present invention, a homogeneous member can be obtained, and particularly, there can be obtained a member having an excellent transparency if a transparent member is used.

(Polymer)

Described hereunder is a polymer of the present invention using the benzotriazole compound according to the first embodiment.

The polymer of the present invention contains the benzotriazole compound of the present invention as a raw material monomer. The polymer of the present invention is suitable for obtaining a resin member having a high transparency, and is itself transparent in a preferred embodiment. However, the polymer of the present invention is not necessarily limited to a transparent polymer.

Though not particularly limited, the polymer of the present invention includes a homopolymer of the benzotriazole compound of the invention; and a copolymer of the benzotriazole compound of the invention and a monomer of another resin raw material capable of reacting with the vinyl groups in the benzotriazole compound of the invention. The polymer of the present invention may be a copolymer of two or more kinds of benzotriazole compounds and monomers. The polymer of the present invention may also be a block copolymer or graft copolymer prepared by reacting the benzotriazole compound of the invention with a high-molecular compound having a reactive functional group(s) at a terminal or a side chain.

Further, the polymer of the present invention may be that prepared by mixing the benzotriazole compound of the invention in a resin; or that prepared by mixing or coating the benzotriazole compound of the invention with a reactive functional group-containing organic compound, inorganic compound or especially resin, and then by allowing them to react with each other.

Specific examples of the monomer used as the raw material of the above copolymer include, but am not particularly limited to a (meth)acrylate-based monomer, a styrene-based monomer, an acrylamide-based monomer, an olefin-based monomer and a vinyl-based monomer.

Examples of the (meth)acrylate-based monomer include, but are not particularly limited to methyl (meth)acrylate, ethyl (meth)acrylate, n-propyl (meth)acrylate, isopropyl (meth)acrylate, n-butyl (meth)acrylate, isobutyl (meth)acrylate, sec-butyl (meth)acrylate, tert-butyl (meth)acrylate, pentyl (meth)acrylate, amyl (meth)acrylate, isoamyl (meth)acrylate, n-hexyl(meth)acrylate, 2-ethylhexyl(meth)acrylate, heptyl(meth)acrylate, octyl(meth)acrylate, decyl (meth)acrylate, dodecyl (meth)acrylate, pentadecyl (meth)acrylate, hexadecyl (meth)acrylate, heptadecyl (meth)acrylate, octadecyl (meth)acrylate, cyclopropyl (meth)acrylate, cyclobutyl (meth)acrylate, cyclopentyl (meth)acrylate, cyclohexyl (meth)acrylate, isobornyl(meth)acrylate, phenyl (meth)acrylate, o-tolyl(meth)acrylate, m-tolyl (meth)acrylate, p-tolyl (meth)acrylate, 2,3-xylyl (meth)acrylate, 2,4-xylyl (meth)acrylate, 2,5-xylyl (meth)acrylate, 2,6-xylyl (meth)acrylate, 3,4-xylyl (meth)acrylate, 3,5-xylyl (meth)acrylate, 1-naphthyl (meth)acrylate, 2-naphthyl (meth)acrylate, binapthyl (meth)acrylate, anthryl methacrylate, benzyl (meth)acrylate, phenoxyethyl (meth)acrylate, 2-hydroxyethyl (meth)acrylate, 3-hydroxypropyl (meth)acrylate, 2,3-dihydroxypropyl (meth)acrylate, 4-hydroxybutyl (meth)acrylate, 6-hydroxyhexyl (meth)acrylate, 2-methoxyethyl (meth)acrylate, glycidyl (meth)acrylate, methylglycidyl (meth)acrylate, 2-hydroxyethyl acryloyl phosphate, 2-methacryloyloxyethyl isocyanate, aminoethyl (meth)acrylate, dimethylaminoethyl (meth)acrylate, t-butylaminoethyl (meth)acrylate, cyclohexyl maleimide and isopropyl maleimide.

Examples of the styrene-based monomer include, but am not particularly limited to alkyl styrenes such as styrene, α-methylstyrene, methylstyrene, dimethylstyrene, trimethylstyrene, ethylstyrene, diethylstyrene, triethylstyrene, propylstyrene, isopropylstyrene, butylstyrene, isobutylstyrene, t-butylstyrene, s-butylstyrene, pentylstyrene, hexylstyrene, heptylstyrene and octylstyrene; halogenated styrenes much as chlorostyrene, fluorostyrene, bromostyrene, dibromostyrene and iodine styrene; alkoxystyrenes such as p-methoxystyrene; arylstyrenes such as p-phenylstyrene; styrene-sulfonic acid or an alkali metal salt thereof; nitrostyrene; aminostyrene; hydroxystyrene; and 4(trimethoxysilyl)styrene.

Examples of the acrylamide-based monomer include, but am not particularly limited to (meth)acrylamide, N,N-dimethylacrylamide, (meth)N,N-diethylacrylamide, (meth)N,N-dipropylacrylamide, (meth)N,N-diisopropylacrylamide, (meth)acryloylmorpholine, diacetone (meth)acrylamide, N-hydroxymethyl (meth)acrylamide, N,N-bishydroxymethyl (meth)acrylamide, N-hydroxyethyl(meth)acrylamide, N,N-bishydroxymethyl(meth)acrylamide, N-hydroxypropyl (meth)acrylamide, N,N-bishydroxypropyl (meth)acrylamide, N-hydroxybutyl (meth)acrylamide and N,N-bishydroxybutyl (meth)acrylamide.

Examples of the olefin-based monomer include, but am not particularly limited to ethylene, propylene, 1-butene, 1-pentene, 1-hexene, 1-heptene, 1-octene, 1-nonene, 1-decene, 4-phenyl-1-butene, 6-phenyl-1-hexene, 3-methyl-1-butene, 4-methyl-1-butene, 3-methyl-1-pentene, 4-methyl-1-pentene, 3-methyl-1-hexene, 4-methyl-1-hexene, 5-methyl-1-hexene, 3,3-dimethyl-1-pentene, 3,4-dimethyl-1-pentene, 4,4-dimethyl-1-pentene, vinylcyclohexane, hexafluoropropene, tetrafluoroethylene, 2-fluoropropene, fluoroethylene, 1,1-difluoroethylene, 3-fluoropropene, trifluoroethylene, 3,4-dichloro-1-butene, butadiene, hexadiene, isoprene, dicyclopentadiene, norbornene and acetylene.

Examples of the vinyl-based monomer include, but am not particularly limited to vinyl acetate, vinyl propionate, vinyl alcohol, allyl alcohol, (meth)acrylonitrile, methacrylonitrile, N-vinylpyrrolidone, vinyl chloride, vinyl bromide, vinyl iodide, vinylidene chloride, vinylidene bromide, vinylidene iodide, vinyl sulfonic acid and salts thereof, methallyl sulfonic acid and salts thereof, 2-acrylamide-2-methyl sulfonic acid and salts thereof, N-vinyl-2-pyrrolidone, (meth)acryloylmorpholine, N-vinylpiperidone, N-vinylpiperazine, N-vinylpyrrole, and N-vinylimidazole.

The benzotriazole compound of the present invention has an excellent solubility in the above-mentioned monomer(s) and can be mixed at a high concentration. Further, even when the benzotriazole compound of the invention is added at a high concentration, it can uniformly dissolve in the monomer(s) and thus be effective in maintaining a high transparency.

Though not particularly limited, the polymer of the present invention can be produced by, for example, the following methods (1) to (3). When producing a homopolymer of the benzotriazole compound, the homopolymer is produced by similar methods without using other monomers.

(1) A method in which the benzotriazole compound of the invention and other monomer(s) are to be mixed together, followed by adding a polymerization initiator thereto with or without the presence of a solvent, stirring the mixture, performing heating ultraviolet irradiation and/or drying, and then removing the solvent after the reaction is over.

(2) A method in which a coating solution containing the benzotriazole compound of the invention and the monomer(s) is to be applied to a base material, followed by performing heating, ultraviolet irradiation and/or drying so as to form a film.

(3) A method in which the benzotriazole compound of the invention and the monomer(s) are to be mixed, followed by casting the mixture into a mold or glass mold, and then performing heating ultraviolet irradiation and/or drying so as to are the same. Among these methods, the method (2) in which a coating solution containing the benzotriazole compound of the invention and the monomer(s) is applied to form a film, is preferable in the present invention in terms of obtaining a transparent multilayer structure, film or sheet.

In this method, the coating solution is prepared by diluting or not diluting the benzotriazole compound of the invention and the monomer(s) with an organic solvent or an aqueous solvent, and then applied to a base material to form a film. If necessary, drying, cooling, heating and/or ultraviolet irradiation are performed to improve film strength.

If forming a film by heating and drying (also in the case of (3)), a polymerization initiator is to be added to the coating solution as necessary. Such polymerization initiator may be any polymerization initiator capable of generating radicals upon heating.

Though not particularly limited, there may be used, for example, a peroxide-based polymerization initiator, an azo compound-based polymerization initiator and a persulfate-based radical polymerization initiator Examples of the peroxide-based polymerization initiator include, but are not particularly limited to benzoyl peroxide, lauroyl peroxide, octanoyl peroxide, orthochoobenzoyl peroxide, orthomethoxybenzoyl peroxide, methylethylketone peroxide diisopropyl peroxydicarbonate, cumene hydroperoxide, cyclohexanone peroxide, t-butyl hydroperoxide and diisopropylbenzene hydroperoxide.

Further, examples of the azo compound-based polymerization initiator include, but are not particularly limited to 2,2'-azobisisobutyronitrile, 2,2'-azobis(2,4-dimethylvaleronitrile), 2,2'-azobis(2,3-dimethylbutyronitrile), 2,2'-azobis(2-methylbutyronitrile), 2,2'-azobis(2,3,3-trimethylbutyronitrile), 2,2'-azobis(2-isopropylbutyronitrile), 1,1'-azobis(cyclohexane-1-carbonitrile), 2,2'-4-methoxy-2,4-dimethylvaleronitrile, 2-(carbamoylazo) isobutyronitrile, 4,4'-azobis(4-cyanovaleric acid) and dimethyl-2,2'-azobisisobutyrate.

Furthermore, examples of the persulfate-based radical polymerization initiator include, but are not particularly limited to potassium persulfate, ammonium persulfate and sodium persulfate.

When the film is formed by ultraviolet irradiation, a photopolymerization initiator may be added to the coating solution as necessary. The photopolymerization initiator may be any photopolymerization initiator capable of generating radicals when irradiated with ultraviolet rays. Though not particularly limited, there may be used, for example, acetophenones, benzoins, benzophenones, phosphine oxides, ketals, anthraquinones and thioxanthones.

A solvent used for dilution may be added to the coating solution as necessary. Examples of such solvent include, but are not particularly limited to aromatic hydrocarbons such as toluene, xylene, cyclohexane and cyclohexylbenzene; hydrocarbons such as n-hexane, heptane and cyclohexan; ethers such as dibutyl ether dimethoxymethane, dimetoxyethane, diethoxyethane, propylene oxide, dioxane, dioxolan, trioxane, tetrahydrofuran, anisole and phenetole; ketones such as methylisobutylketone, methylisobutylketone, acetone, methylethylketone, diethylketone, dipropylketone, diisobutylketone, cyclopentanone, cyclohexanon and methylcyclohexanone; esters such as ethyl formate, propyl formate, n-pentyl formate, methyl acetate, ethyl acetate, methyl propionate, ethyl propionate, n-pentyl acetate and γ-butyrolactone; cellosolves such as methyl cellosolve, cellosolve, butyl cellosolve and cellosolve acetate; alcohols such as methanol, ethanol and isopropyl alcohol; and water.

If necessary, there may be added to the coating solution additives such as an antifoaming agent, a leveling agent, an antioxidant, a light stabilizer, a polymerization inhibitor, a catalyst, a dye and a pigment.

Though not particularly limited, the coating solution prepared can be applied to the base material via appropriate methods such as those using a bar coater, a gravure coater, a comma coater, a lip coater, a curtain coater, a roll coater, a blade coater, a spin coater, a reverse coater or a die coater; as well as methods such as spraying and dipping.

There are no particular restrictions on the base material to be coated; such base material may, for example, be a resin plate, a resin film, a resin sheet, a glass, a building material, a meal plate or a wood material.

(Member)

Described hereunder is a member, especially a resin member of the invention (including the polymer of the present invention) to which the benzotriazole compounds of the first and second embodiments have been added.

The benzotriazole compound of the present invention can also be mixed and kneaded with organic or inorganic materials, especially resins before use. Alternatively, the benzotriazole compound of the first embodiment of the invention may be mixed and reacted with an organic or inorganic material having a substituent group(s) capable of reacting with the vinyl groups in the benzotriazole compound of the first embodiment of the invention, such that an ultraviolet absorbing ability can be imparted to the organic or inorganic material. These are regarded as the members of the present invention employing organic or inorganic materials as base materials, particularly as the resin members of the present invention if using a resin as a base material.

There are no particular restrictions on a resin(s) to be mixed and kneaded with the benzotriazole compound of the present invention; there may be used, for example, a thermoplastic resin and a thermosetting resin. Examples of the thermoplastic resin include, but are not particularly limited to polyvinyl chloride, polyvinylidene chloride, polytetrafluoroethylene, polyolefin, polycarbonate, polystyrene, acrylic resin, methacrylic resin, polymaleimide, polyamide, polyvinylpyrrolidone, polyester, acrylonitrile-butadiene-styrene (ABS) resin, polyurethane resin, vinyl chloride-vinylidene chloride-acrylonitrile copolymer, acrylonitrile-styrene (AS) resin, styrene-isoprene copolymer, vinyl acetate resin, polyvinyl alcohol, polyvinyl sulfonic acid and salts thereof, polyphenylene ether, polysulfone, polyether sulfone, polyether ketone (PEK), polyetherether ketone (PEEK) and liquid crystal plastics. Examples of the thermosetting resin include, but are not particularly limited to a phenolic resin, a urea resin, a melamine resin, an acrylic melamine resin, an unsaturated polyester, a silicon resin, an alkyd resin, an epoxy resin, a polyethylene terephthalate resin, an episulfide resin and a nylon resin. Among them, transparent resins can be preferably used, examples of which include polycarbonate, polystyrene, an acrylic resin, a methacrylic resin, a polyethylene terephthalate resin, a urea resin, a melamine resin and an acrylic melamine resin. More preferred are polycarbonate, polystyrene, an acrylic resin, a methacrylic resin, a polyethylene terephthalate resin, a melamine resin and an acrylic melamine resin.

When reacting, mixing and kneading while performing heating, an ultraviolet absorber with organic and inorganic substances such as a resin(s), and when processing and molding an ultraviolet absorber-containing resin member by heating, it is desired that the ultraviolet absorber have a higher thermal decomposition temperature as an ultraviolet absorbing effect cannot be fully exhibited if the ultraviolet absorber decomposes at a low thermal decomposition temperature. In this regard, as is the case of the first embodiment, the 5% weight reduction temperature of the benztriazole compound of the present invention is preferably not lower than 255° C., more preferably not lower than 270° C., even more preferably not lower than 280° C., particularly preferably not lower than 290° C., further particularly preferably not lower than 300° C., and especially preferably not lower than 310° C.

There are no particular restrictions on a method for molding the resin member of the present invention; there may be employed, for example, an injection molding method, an extrusion molding method, a Calendar molding method, a blow molding method or a compression molding method. If an extruder is used, the resin member can be produced by forming a film with an extruder, or by producing a raw material with an extruder at first, and then stretching such raw material to one or two axes so as to form a film.

When performing kneading, additives used for ordinary resin molding may be added, examples of which include an infrared absorber, an ultraviolet absorber, a high refractive index agent, an antioxidant, a light stabilizer, a flame retardant and a plasticizer.

When the resin member of the present invention is used as apart of a film or member having a functional optical layer(s), there are no particular restrictions on a film thickness, provided that the film thickness is in a range capable of satisfying properties that are required for a resin material such as the type of the resin material, an adhesiveness, a hardness and optical properties; the film thickness may, for example, be in a range of 50 nm to 250 μm.

The resin member of the invention can be used for all applications where a synthetic resin is used; and is particularly suitable for, though not particularly limited to, applications where there exists a possibility of being exposed to sunlight or a light including ultraviolet rays. For example, the applications may include glass substitutes and surface coating materials thereof; window glasses for houses, facilities, transportation equipments or the like, and coating materials thereof; coating materials for daylighting glasses and light source protective glasses; coating materials for lighting protective members used in houses, facilities, transportation equipments or the like; windows films for houses, facilities, transportation equipments or the like; interior/exterior materials and interior/exterior coating materials for houses, facilities, transportation equipments or the like, and coating film formed by such coating materials; light source members such as fluorescent lamps, mercury lamps, halogen bulbs, LED lights or the like; materials for precision instruments and electronic and electrical equipments; materials for shielding, for example, electromagnetic waves generated from various displays; containers or packaging materials for foods, chemicals, drugs and cosmetics or the like; sheets or film materials for agricultural and industrial uses; discoloration inhibitors for printed materials, dyed materials, dyes/pigments or the like; safety glasses; glass interlayers; cosmetics; clothing textile products; fibers; interior articles for household use such as curtains, carpets and wallpapers; medical instruments such as plastic lenses, contact lenses and artificial eyes; and optical filters, sign boards, indicators or the like as well as surface coating materials thereof.

Among them, the resin member of the present invention is especially suitable for an optical material, in particular, a film or member having a functional optical layer(s), an adhesive, an adhesive agent and an optical molded product, in view of the fact that the resin member of the invention is capable of imparting an ultraviolet absorbing ability and a high refractive index while maintaining the transparency of the matrix.

As a film or member having a functional optical layer(s), it may be a single layer film; or a multilayer film or optical layer-containing substrate in which one or multiple optical layers according to various applications are provided on a base material film or substrate; when multiple optical layers are to be provided, the resin member of the present invention is used in at least one of these layers.

Among films and members having a functional optical layer(s), an optical film may be a base material film provided with a functional layer(s) according to various applications. Examples of such optical film include, but are not particularly limited to various optical disk substrate protective films, reflective films, anti-reflective films, alignment films, polarizing films, polarizing layers, protective films, retardation films, light diffusion film, viewing angle improving films, electromagnetic wave shield films, anti-glare films, light shielding films and brightness improving films.

There are no particular restrictions on a member having a functional optical layer(s). Examples of such member having a functional optical layer(s) include members produced by laminating on the surface of a panel substrate or the like one or multiple layers of at least one of; for example, an antireflection layer, a hard cost layer, an antistatic layer an adhesion stabilizing layer, a protective layer, an electromagnetic wave shield layer and an infrared-cut layer.

The resin member of the present invention is suitable for a surface protective film for solar cells. A solar cell element usually has a structure in which an active layer serving as a solar cell is provided between a pair of substrates. Here, a flexible solar cell requires a protective film having an ultraviolet absorption property, because a polyester material such as a gas barrier film used as a member of the cell or an active layer itself in the case of an organic solar cell will deteriorate after absorbing ultraviolet rays. Further, since solar cells are installed outdoors for many years, such protective film is required to have a high weather resistance. Furthermore, since solar cells absorb light energy and convert it into electric power, a high transparency is required for such protective film. That is, as a protective film for protecting a flexible solar cell is required to have a high transparency, a high ultraviolet absorption capability, a high weather resistance and a flexibility, the resin member of the present invention is suitable for such application.

In addition, the resin member of the present invention can be suitably used in optical lenses, prisms and filters, such as spectacle plastic lens elements, contact lenses, optical pickup lenses, camera lenses and lenticular lenses; optical substrates such as touch panel substrates and light guide plates; and optical molded products such as optical fibers and information recording substrates. In the case of optical lenses, the resin member of the present invention is also suitable for plastic lenses such as lens films including, for example, a Fresnel lens film and a lenticular lens film; and suitable for a microlens array using a microlens having a micro-diameter of several µm, such microlens array being used for the purposes of for example, enhancing a light condensing property and light diffusing property in a miniaturized optical functional element, and condensing lights to a light receiving element of an image pickup element.

Moreover, the resin member of the present invention is also suitable for substrates and films for displays, example of which include: substrates and films for flat panel displays such as a liquid crystal display, an organic EL display, a plasma display, a field emission display and an electronic paper; or substrates and films for backlights of a liquid crystal display, a traffic light, a neon sign or the like.

The benzotriazole compound of the present invention can also be applied to inorganic materials. Examples of such inorganic materials include, but are not particularly limited to a siliceous material prepared by a sol-gel method, a glass, a water glass, a low-melting-point glass, a quart, a silicon resin, an alkoxysilane and silane coupling agent. Examples of the glass include, but are not particularly limited to silicon oxide, an alkali-free glass and a soda glass. Examples of the water glass include, but are not particularly limited to an aqueous solution of a water-soluble alkali metal salt e.g. silicate soda, potassium silicate or the like. Examples of the low-melting-point glass include, but are not particularly limited to glasses containing lead oxide (PbO) and boric anhydride ($B_2O_3$) as main components. Examples of the silicon resin include, but are not particularly limited to a methyl silicon resin, a methylphenyl silicon resin, and an organic resin-modified silicon resin that has been modified with an epoxy resin, an alkyd resin, a polyester resin or the like. Examples of the alkoxysilane include dimysanethyphnykmthxysilane, methylvinyldimethoxysihme, 3-mercaptopropylmethyldimethoxysilane, 3,3,3-trifluoropropyl methyldimethoxysilane, methyltrimethoxysilane, vinyltrimethoxysilane and 3-mercaptopropyltrimethoxysilane Examples of the silane coupling agent include, but are not particularly limited to 2-(3,4-epoxycyclohexyl)ethyltrimethoxysilane, 3-glycidoxypropylmethyldimethoxysilane, 3-glycidoxypropyltrimethoxysilane, 3-glycidoxypropylmethyldiethoxysilane, 3-glycidoxypropyltriethoxysilane, 3-methacryloxypropylmethyldimethoxysilane, 3-methacryloxypropyltrimethoxysilane, 3-isocyanatepropyltriethoxysilane, N-2-(aminoethyl)-3-aminopropylmethyldimethoxysilane, N-2-(aminoethyl)-3-aminopropyltriethoxysilane, 3-triethoxysilyl-N-(1,3-dimethyl-butylidene)propylamine, N-phenyl-3-aminopropyltrimethoxysilane, 3-mercaptopropylmethyldimethoxysilane, 3-mercaptopropyltrimethoxysilane, bis(triethoxysilylpropyl)tetrasulfide and 3-isocyanatepropyl ethoxysilane.

Further, the benzotriazole compound of the present invention, while possessing the above functions, is used for applications requiring stabilization and functionalization by an ultraviolet absorber. Though not particularly limited, the benzotriazol compound of the invention may also be used in, for example, glass substitutes; window glasses and daylighting glasses for houses, facilities, transportation equipments or the like; lighting members and protective members used in houses facilities, transportation equipments or the like; interior/exterior materials and interior/exterior coating materials for houses, facilities, transportation equipments or the like, and coating films formed by such coating materials; light source members such as fluorescent lamps, mercury lamps, halogen bulbs, LED lights or the like; materials for precision instruments and electronic and electrical equipments; materials for shielding, for example, electromagnetic waves generated from various displays; containers or packaging materials for foods, chemicals and drugs or the like; discoloration inhibitors for printed materials, dyed materials, dyes/pigments or the like; protective films of resin members; safety glasses; glass interlayers; cosmetics; clothing textile products; fibers; interior articles for household use such as curtains, carpets and wallpapers; medical instruments such as plastic lenses, artificial eyes or the like; optical products such as optical filters, backlight display films, prisms, mirrors and photographic materials; stationary products; and sign boards, indicators or the like as well as surface coating materials thereof.

Working Examples

Hereinbelow, the invention will be explained in more detail by means of working examples, but the invention is not limited to these working examples.

1. Synthesis of Ultraviolet Absorbers
<Synthesis of Intermediate Compounds>
Intermediates 1 to 7 represented by the following formula were synthesized.
<Intermediate 1>

[Chemical Formula 8]

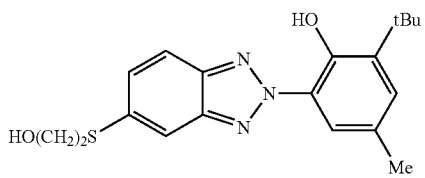

2-(2-hydroxy-3-tert-butyl-5-methylphenyl)-5-chlorobenzotriazole (5.00 g 15.8 mmol), 2-mercaptoethanol (2.48 g 31.7 mmol), potassium carbonate (4.82 g 69.7 mmol) and potassium iodide (3.95 g 47.5 mmol) were heated and stirred in 13 mL of DMF for 8 hours at 135-140° C. After the reaction was completed, pH-adjustment, filtering and washing with MeOH were performed, followed by column purification and then recrystallization to obtain an intermediate 1 as a light yellow solid.

<Intermediate 2>

[Chemical Formula 9]

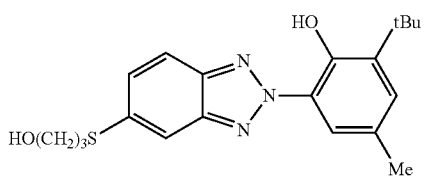

2-(2-hydroxy-3-tert-butyl-5-methylphenyl)-5-chlorobenzotriazole (6.85 g 21.7 mmol), 3-mercapto-1-propanol (3.00 g 32.5 mmol), potassium carbonate (6.60 g 47.7 mmol) and potassium iodide (0.25 g 1.52 mmol) were heated and stirred in 30 mL of DMF for 8 hours at 135-140° C. After the reaction was completed, pH-adjustment, filtering and washing with MeOH were performed, followed by recrystallization to obtain an intermediate 2 as a light yellow solid.

<Intermediate 3>

[Chemical Formula 10]

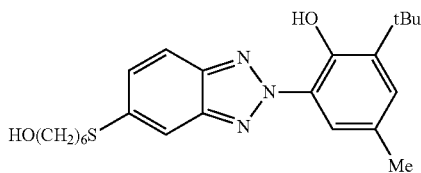

2-(2-hydroxy-3-tert-butyl-5-methylphenyl)-5-chlorobenzotriazole (18.82 g 59.6 mmol), 6-mercapto-1-hexanol (12.00 g 89.4 mmol), potassium carbonate (18.21 g 131.1 mmol) and potassium iodide (0.69 g 4.17 mmol) were heated and stirred in 60 mL of DMF for 10 hours at 135-140° C. After the reaction was completed, there were performed pH-adjustment, filtering and washing with MeOH, followed by recrystallization to obtain an intermediate 3 as a light yellow solid.

<Intermediate 4>

[Chemical Formula 11]

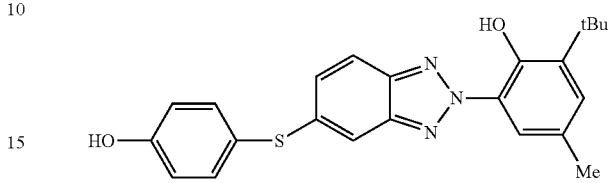

2-(2-hydroxy-3-tert-butyl-5-methylphenyl)-5-chlorobenzotriazole (25.0 g 79.2 mmol), 4-hydroxybenzenethiol (20.0 g 158.3 mmol), potassium carbonate (24.1 g, 174.2 mmol) and potassium iodide (0.92 g 5.54 mmol) were reacted in 66 mL of DMF at 125° C. for 12 hours. After the reaction was completed, the pH was adjusted, followed by filtration, methanol washing, water washing, recrystallization, and column purification to obtain an intermediate 4 as a light yellow solid.

<Intermediate 5>

[Chemical Formula 12]

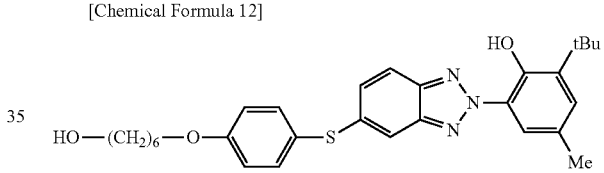

Intermediate 4 (0.50 g 1.23 mmol), 6-bromo-1-hexanol (0.23 g 1.29 mmol), and potassium carbonate (0.33 g 2.46 mmol) were reacted in 15 mL of acetonitrile at W C for 15 hours. After the reaction was completed, acid treatment and water washing were performed, and the organic layer was evaporated to obtain a yellow crude product, which was then subjected to column purification to synthesize a light yellow liquid intermediate 5.

<Intermediate 6>

[Chemical Formula 13]

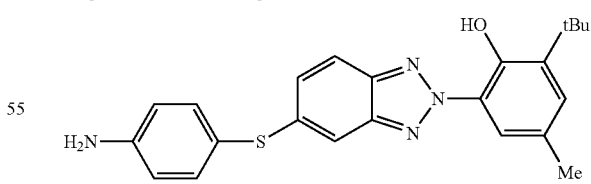

2-(2-hydroxy-3-tert-butyl-5-methylphenyl)-5-chlorobenzotriazole (5.00 g 15.8 mmol), 4-aminobenzenethiol (2.97 g 23.8 mmol), potassium carbonate (4.81 g, 34.8 mmol) and potassium iodide (0.18 g 1.11 mmol) were reacted in DMF30 g at 135° C. for 3 hours. After the reaction was completed, the pH was adjusted, followed by filtering, washing with water, washing with MeOH, and recrystallization to obtain an intermediate 6 as a light yellow solid.

<Intermediate 7>

[Chemical Formula 14]

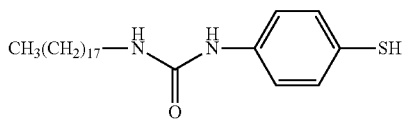

4-Aminobenxenethiol (1.50 g 12.0 mmol) and octadecyl isocyanate (3.54 g 12.0 mmol) were heated and stirred in 10 mL of DMF at 90° C. for 8 hours. After the reaction was completed, MeOH was added and the precipitated crystals were filtered to obtain a milky white crude product. The crude product thus obtained was recrystallized with MeOH to obtain a white intermediate 7.

Compounds 1 to 9 and 13 to 27 represented by the following chemical formulae were synthesized.

<Compound 1>

[Chemical Formula 15]

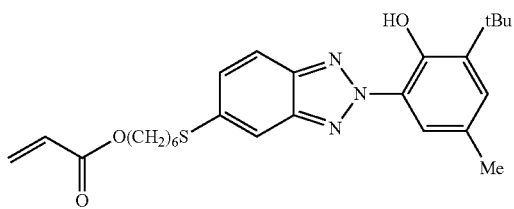

Intermediate 3 (0.50 g 1.21 mmol), acrylic acid (0.13 g 1.82 mmol) and p-toluenesulfonic acid (0.023 g 0.12 mmol) were heated and stirred in 15 mL of toluene for 18 hours at 80-90° C. After the reaction was completed, the reaction mixture was stirred for 1 hour with addition of KYO-WAAD® 500, filtered, and the filtrate was evaporated to obtain a yellow crude product, which was then recrystallized to synthesize Compound 1 as a light yellow solid. Physical property values thereof are shown below:

FT-IR (KBr): 3099 $cm^{-1}$: O—H stretching vibration 1719 $cm^{-1}$: C═O stretching vibration 1411, 1362 $cm^{-1}$: triazole ring stretching vibration $^1$H-NMR (CDCl$_3$ 400 MHz): δ 1.31-1.54 (m, 13H, —O—CH$_2$CH$_2$C$\underline{H}_2$C$\underline{H}_2$CH$_2$CH$_2$—S—, -Ph-OH—CH$_3$—C(C$\underline{H}_3$)$_3$), 1.68 (quin, 2H, —O—CH$_2$C$\underline{H}_2$CH$_2$CH$_2$CH$_2$CH$_2$—S—), 1.74 (quin, 2H, —O—CH$_2$CH$_2$CH$_2$CH$_2$CH$_2$C$\underline{H}_2$—S—), 2.38 (s, 3H, -Ph-OH—C$\underline{H}_3$—C(CH$_3$)$_3$), 3.03 (t, 2H, —O—CH$_2$CH$_2$CH$_2$CH$_2$CH$_2$C$\underline{H}_2$—S—), 4.17 (t, 2H, —O—C$\underline{H}_2$CH$_2$CH$_2$CH$_2$CH$_2$CH$_2$—S—), 6.12 (q, 1H, CH$_2$═C$\underline{H}$—C(═O)—O—), 6.37, 5.79 (d, 1H, C$\underline{H}_2$═CH—C(═O)—O—), 7.16 (s, 1H), 7.3 (d, 1H), 7.71 (s, 1H), 7.81 (d, 1H), 8.05 (S, 1H), (insg.5arom. C$\underline{H}$), 11.59 (s, 1H, -Ph-O$\underline{H}$—CH$_3$—C(CH$_3$)$_3$) $^{13}$C-NMR (CDCl$_3$ 400 MHz): δ 20.9 (-Ph-OH—$\underline{C}$H$_3$—C(CH$_3$)$_3$), 25.6 (-Ph-OH—CH$_3$—$\underline{C}$(CH$_3$)$_3$), 28.5~29.5 (C═C—C(═O)—O—CH$_2$CH$_2$($\underline{C}$H$_2$)$_3$CH$_2$—S), 29.5 (-Ph-OH—CH$_3$—C($\underline{C}$H$_3$)$_3$), 33.1 (C═C—C(═O)—O—(CH$_2$)$_4$$\underline{C}$H$_2$—S), 35.4(C═C—C(═O)—O—(CH$_2$)$_5$$\underline{C}$H$_2$—S), 64.4 (C═C—C(═O)—O—$\underline{C}$H$_2$(CH$_2$)$_5$—S), 113.8, 117.6, 119.3, 128.6, 129.3 ($\underline{C}$H$_{arom}$), 125.4, 141.2, 143.4 ($\underline{C}_{arom}$), 128.3 (C$_{arom}$—$\underline{C}$H$_3$), 137.4($\underline{C}_{arom}$—S), 139.1($\underline{C}_{arom}$—C(CH$_3$)$_3$), 146.7($\underline{C}_{arom}$—OH) 128.7 ($\underline{C}$═C—C(═O)—O—), 130.6 (C═$\underline{C}$—C(═O)—O—), 166.3 (C═C—$\underline{C}$(═O)—O—)

<Compound 2>

[Chemical formula 16]

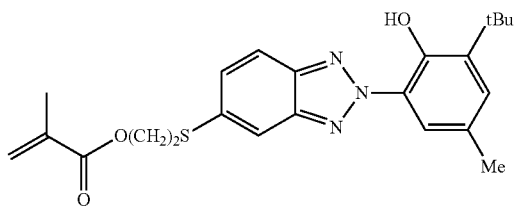

Intermediate 1 (0.60 g 1.68 mmol), methacrylic acid (0.22 g 2.51 mmol) and p-toluenesulfonic acid (0.0319 g 0.168 mmol) were heated and stirred in 15 mL of toluene for 18 hours at 80-90° C. After the reaction was completed, the reaction mixture was stirred for 1 hour with the addition of KYOWAAD® 500, filtered, and the filtrate was evaporated to obtain a crude product in a liquid state, followed by column purification to obtain Compound 2 as a light yellow viscous liquid. Physical property values thereof are shown below.

FT-IR (KBr): 2956 $cm^{-1}$: O—H stretching vibration 1720 $cm^{-1}$: C═O stretching vibration 1451, 1359 $cm^{-1}$: triazole ring stretching vibration $^1$H-NMR (CDCl$_3$ 400 MHz): δ 1.49 (S, 9H, -Ph-OH—C(C$\underline{H}_3$)$_3$), 1.92 (S, 3H, CH$_2$═C(C$\underline{H}_3$)—C(═O)—O—), 2.39 (s, 3H, -Ph-OH—C$\underline{H}_3$—C(CH$_3$)$_3$), 3.33 (t, 2H, —O—CH$_2$C$\underline{H}_2$—S—), 4.41(t, 2H, —O—C$\underline{H}_2$CH$_2$—S—), 5.56 (S, 1H, C$\underline{H}_2$═C(CH$_3$)—C(═O)—O—), 6.09 (S, 1H, C$\underline{H}_2$═C(CH$_3$)—C(═O)—O—), 7.18 (s, 1H), 7.44 (d, 1H), 7.83 (s, 1H), 7.89 (d, 1H), 8.06 (S, 1H), (insg.5arom. C$\underline{H}$), 11.57 (s, 1H, -Ph-O$\underline{H}$—CH$_3$—C(CH$_3$)$_3$)

$^{13}$C-NMR (CDCl$_3$ 400 MHz): δ 18.3 (C═C($\underline{C}$H$_3$)—C(═O)—O—), 20.9 (-Ph-OH—$\underline{C}$H$_3$—C(CH$_3$)$_3$), 29.5 (-Ph-OH—CH$_3$—C($\underline{C}$H$_3$)$_3$), 32.1 (-Ph-OH—CH$_3$—$\underline{C}$(CH$_3$)$_3$), 35.4(C═C—C(═O)—O—CH$_2$$\underline{C}$H$_2$—S), 62.8 (C═C—C(═O)—O—$\underline{C}$H$_2$CH$_2$—S), 115.7, 118.0, 119.4, 128.9, 129.6 ($\underline{C}$H$_{arom}$), 125.4, 141.5, 143.2($\underline{C}_{arom}$), 128.3 (C$_{arom}$—$\underline{C}$H$_3$), 135.9($\underline{C}_{arom}$—S), 139.2($\underline{C}_{arom}$—C(CH$_3$)$_3$), 146.7($\underline{C}_{arom}$—OH) 126.1 ($\underline{C}$═C(CH$_3$)—C(═O)—O—), 135.8 (C═$\underline{C}$(CH$_3$)—C(═O)—O—), 167.1(C═C(CH$_3$)—$\underline{C}$(═O)—O—)

<Compound 3>

[Chemical Formula 17]

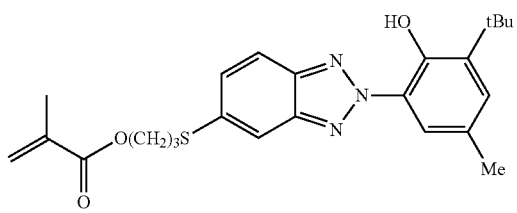

Intermediate 2 (3.00 g 8.08 mmol), methacrylic acid (1.04 g 12.11 mmol) and p-toluenesulfonic acid (0.15 g 0.81 mmol) were heated and stirred in 50 mL of toluene for 18 hours at 80-90° C. After the reaction was completed, the reaction mixture was stirred for 1 hour with the addition of KYOWAAD® 500, filtered, and the filtrate was evaporated to obtain a yellow crude product, which was then recrystallized to synthesize Compound 3 as a light yellow solid. Physical property values thereof are shown below:

FT-IR (KBr): 2958 cm$^{-1}$: O—H stretching vibration 1706 cm$^{-1}$: C=O stretching vibration 1453, 1392 cm$^{-1}$: triazole ring stretching vibration $^1$H-NMR (CDCl$_3$ 400 MHz): δ 1.49 (S, 9H, -Ph-OH—CH$_3$—C(C$\underline{H}_3$)$_3$), 1.96 (S, 3H, CH$_2$=C(C$\underline{H}_3$)—C(=O)—O—), 2.01(quin, 2H, —O—CH$_2$C$\underline{H}_2$CH$_2$—S—), 2.38 (s, 3H, -Ph-OH—C$\underline{H}_3$—C(CH$_3$)$_3$), 3.13 (t, 2H, —O—CH$_2$CH$_2$C$\underline{H}_2$—S—), 4.31 (t, 2H, —O—C$\underline{H}_2$CH$_2$CH$_2$—S—), 5.60 (S, 1H, C$\underline{H}_2$=C(CH$_3$)—C(=O)—O—), 6.14(S, 1H, C$\underline{H}_2$=C(CH$_3$)—C(=O)—O—), 7.17 (s, 1H), 7.40 (d, 1H), 7.76 (s, 1H), 7.81 (d, 1H), 8.05 (S, 1H), (insg.5arom. C$\underline{H}$), 11.58 (s, 1H, -Ph-O$\underline{H}$—CH$_3$—C(CH$_3$)$_3$)

$^{13}$C-NMR (CDCl$_3$ 400 MHz): δ 18.4 (C=C($\underline{C}$H$_3$)—C(=O)—O—), 20.9 (-Ph-OH—$\underline{C}$H$_3$—C(CH$_3$)$_3$), 28.1 (-Ph-OH—CH$_3$—$\underline{C}$(CH$_3$)$_3$), 29.5 (-Ph-OH—CH$_3$—C($\underline{C}$H$_3$)$_3$), 29.9 (C=C—C(=O)—O—CH$_2$$\underline{C}$H$_2$CH$_2$—S), 35.4 (C=C—C(=O)—O—CH$_2$CH$_2$$\underline{C}$H$_2$—S), 63.0 (C=C—C(=O)—O—$\underline{C}$H$_2$CH$_2$CH$_2$—S), 114.5, 117.8, 119.3, 128.8, 129.4 ($\underline{C}$H$_{arom}$), 125.4, 141.4, 143.3 ($\underline{C}_{arom}$), 128.3 (C$_{arom}$—$\underline{C}$H$_3$), 136.8 ($\underline{C}_{arom}$—S), 139.2 ($\underline{C}_{arom}$—C(CH$_3$)$_3$), 146.7($\underline{C}_{arom}$—OH), 125.7 ($\underline{C}$=C(CH$_3$)—C(=O)—O—), 136.2 (C=$\underline{C}$(CH$_3$)—C(=O)—O—), 167.3 (C=C(CH$_3$)—$\underline{C}$(=O)—O—)

<Compound 4>

[Chemical Formula 18]

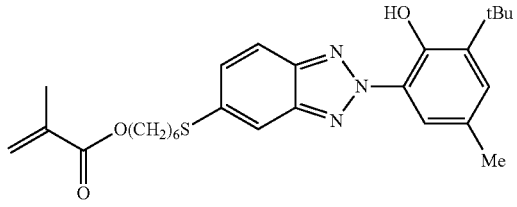

Intermediate 3 (0.60 g 1.0 mmol), methacrylic acid (0.22 g 2.55 mmol) and p-toluenesulfonic acid (0.0323 g 0.17 mmol) were heated and stirred in 15 mL of toluene for 18 hours at 80-90° C. After the reaction was completed, the reaction mixture was stirred for 1 hour with the addition of KYOWAAD® 500, filtered, and the filtrate was evaporated to obtain a yellow crude product, which was then recrystallized to synthesize Compound 4 as alight yellow solid. Physical property values thereof are shown below:

FT-IR (KBr): 2943 cm$^{-1}$: O—H stretching vibration 1712 cm$^{-1}$: C=O stretching vibration 1433, 1362 cm$^{-1}$: triazole ring stretching vibration $^1$H-NMR (CDCl$_3$ 400 MHz): δ 1.44-1.54 (m, 13H, —CH$_2$CH$_2$C$\underline{H}_2$C$\underline{H}_2$CH$_2$CH$_2$—S—, -Ph-OH—CH$_3$—C(C$\underline{H}_3$)$_3$), 1.70 (quin, 2H, —O—CH$_2$C$\underline{H}_2$CH$_2$CH$_2$CH$_2$—S—), 1.74 (quin, 2H, —O—CH$_2$CH$_2$CH$_2$CH$_2$C$\underline{H}_2$—S—), 1.94 (S, 3H, CH$_2$=C(C$\underline{H}_3$)—C(=O)—O—), 2.38 (s, 3H, -Ph-OH—C$\underline{H}_3$—C(CH$_3$)$_3$), 3.05 (t, 2H, —O—CH$_2$CH$_2$CH$_2$CH$_2$C$\underline{H}_2$—S—), 4.14 (t, 2H, —O—C$\underline{H}_2$CH$_2$CH$_2$CH$_2$CH$_2$—S—), 5.54 (S, 1H, C$\underline{H}_2$=C(CH$_3$)—C(=O)—O—), 6.09 (S, 1H, C$\underline{H}_2$=C(CH$_3$)—C(=O)—O—), 7.16 (s, 1H), 7.37 (d, 1H), 7.71 (s, 1H), 7.82 (d, 1H), 8.05 (S, 1H), (insg.5arom. C$\underline{H}$), 11.59 (s, 1H, -Ph-O$\underline{H}$—CH$_3$—C(CH$_3$)$_3$)

$^{13}$C-NMR (CDCl$_3$ 400 MHz): δ 18.3 (C=C($\underline{C}$H$_3$)—C(=O)—O—), 20.9 (-Ph-OH—$\underline{C}$H$_3$—C(CH$_3$)$_3$), 25.6 (-Ph-OH—CH$_3$—$\underline{C}$(CH$_3$)$_3$), 28.5~29.5 (C=C($\underline{C}$H$_3$)—C(=O)—O—CH$_2$CH$_2$($\underline{C}$H$_2$)$_3$CH$_2$—S), 29.5 (-Ph-OH—CH$_3$—C($\underline{C}$H$_3$)$_3$), 33.1 (C=C($\underline{C}$H$_3$)—C(=O)—O—(CH$_2$)$_4$$\underline{C}$H$_2$CH$_2$—S), 35.4 (C=C(CH$_3$)—C(=O)—O— CH$_2$(CH$_2$)$_4$$\underline{C}$H$_2$—S), 64.6 (C=C(CH$_3$)—C(=O)—O—$\underline{C}$H$_2$(CH$_2$)$_4$CH$_2$—S), 113.8, 117.6, 119.3, 128.7, 129.3 ($\underline{C}$H$_{arom}$), 125.4, 141.2, 143.3 ($\underline{C}_{arom}$), 128.3 (C$_{arom}$—$\underline{C}$H$_3$), 137.8 ($\underline{C}_{arom}$—S), 139.1 ($\underline{C}_{arom}$—C(CH$_3$)$_3$), 146.7($\underline{C}_{arom}$—OH), 125.3 ($\underline{C}$=C(CH$_3$)—C(=O)—O—), 137.8 (C=$\underline{C}$(CH$_3$)—C(=O)—O—), 167.3 (C=C(CH$_3$)—$\underline{C}$(=O)—O—)

<Compound 5>

[Chemical Formula 19]

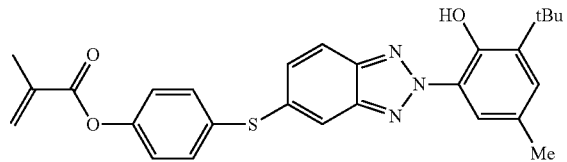 [SMILES: C=C(C)C(=O)Oc1ccc(Sc2ccc3nn(-c4cc(C)cc(C(C)(C)C)c4O)nc3c2)cc1]

Intermediate 4 (0.50 g 1.23 mmol), methacryloyl chloride (0.26 g 2.47 mmol) and triethylamine (0.21 g 2.71 mmol) were stirred in 15 mL of methylene chloride for 15 hours at room temperature. After the reaction was completed, chloroform and water were added to form two layers, and then acid treatment and water washing thereof were performed, and the organic layer was evaporated to obtain a yellow crude product, which was then recrystallized to synthesize Compound 5 as a light yellow solid. Physical property values thereof are shown below:

FT-IR (KBr): FT-IR (KBr): 2956 cm$^{-1}$: O—H stretching vibration 1724 cm$^{-1}$: C=O stretching vibration 1446, 1391 cm$^{-1}$: triazole ring stretching vibration $^1$H-NMR (CDCl$_3$ 400 MHz): δ 1.48 (s, 9H, -Ph-OH—CH$_3$—C(C$\underline{H}_3$)$_3$), 2.08 (S, 3H, CH$_2$=C(C$\underline{H}_3$))—C(=O)—O—), 2.38 (s, 3H, -Ph-OH—C$\underline{H}_3$—C(CH$_3$)$_3$), 5.79(S, 1H, C$\underline{H}_2$=C(CH$_3$)—C(=O)—O—), 6.37 (S, 1H, C$\underline{H}_2$=C(CH$_3$)—C(=O)—O—), 7.12(s, 1H), 7.18 (d, 2H), 7.35 (d, 1H), 7.51 (d, 2H), 7.70 (s, 1H), 7.82 (d, 1H), 8.04 (s, 1H), (msg.9arom. C$\underline{H}$), 11.55 (s, 1H, -Ph-O$\underline{H}$—CH$_3$—C(CH$_3$)$_3$)

$^{13}$C-NMR (CDCl$_3$ 400 MHz): δ 18.4 (C=C($\underline{C}$H$_3$)—C(=O)—O—), 20.9 (-Ph-OH—$\underline{C}$H$_3$—C(CH$_3$)$_3$), 25.6 (-Ph-OH—CH$_3$—$\underline{C}$(CH$_3$)$_3$), 29.5 (-Ph-OH—CH$_3$—C($\underline{C}$H$_3$)$_3$), 116.7, 118.1, 119.3, 128.7, 129.3, 125.4, 134.0 ($\underline{C}$H$_{arom}$), 125.4, 141.7, 143.2 ($\underline{C}_{arom}$), 128.3 (C$_{arom}$—$\underline{C}$H$_3$), 128.9 ($\underline{C}_{arom}$—S), 137.3 ($\underline{C}_{arom}$—S), 139.2 ($\underline{C}_{arom}$—C(CH$_3$)$_3$), 146.7($\underline{C}_{arom}$—OH), 151.1(C$_{arom}$—O—), 125.4 ($\underline{C}$=C(CH$_3$)—C(=O)—O—), 135.7 (C=$\underline{C}$(CH$_3$)—C(=O)—O—), 167.3 (C=C(CH$_3$)—$\underline{C}$(=O)—O—)

35

<Compound 6>

[Chemical Formula 20]

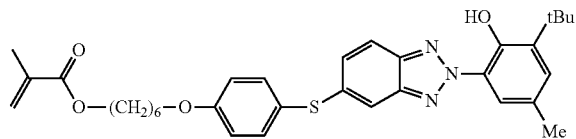

Adopting intermediate 5 (0.50 g 0.98 mmol), methacrylic acid (0.13 g 1.48 mmol) and p-toluenesulfonic acid (0.0188 g 0.0989 mmol) were heated and stirred in 15 mL of toluene for 18 hours at 80-90° C. After the reaction was completed, the reaction mixture was stirred for 1 hour with the addition of KYOWAAD® 500, filtered, and the filtrate was evaporated to obtain a crude product. The crude product thus obtained was subjected to column purification to obtain a light yellow viscous liquid Compound 6. Physical property values thereof are shown below: FT-IR (KBr): 2953 cm$^{-1}$: O—H stretching vibration 1716 cm$^{-1}$: C=O stretching vibration 1453, 1392 cm$^{-1}$: triazole ring stretching vibration $^1$H-NMR (CDCl$_3$ 400 MHz): δ1.31-1.46 (m, 4H, —O—CH$_2$CH$_2$CH$_2$CH$_2$CH$_2$CH$_2$—O—Ph-), 1.47 (s, 9H, -Ph-OH—CH$_3$—C(CH$_3$)$_3$), 1.72(quin, 2H, —O—CH$_2$CH$_2$CH$_2$CH$_2$CH$_2$—O—Ph-), 1.84 (quin, 2H, —O—CH$_2$CH$_2$CH$_2$CH$_2$CH$_2$CH$_2$—O—Ph-), 1.95 (S, 3H, CH$_2$=C(CH$_3$)—C(=O)—O—), 2.36 (s, 3H, -Ph-OH—CH$_3$—C(CH$_3$)$_3$), 4.01 (t, 2H, —O—CH$_2$CH$_2$CH$_2$CH$_2$CH$_2$CH$_2$—O—Ph-), 4.17 (t, 2H, —O—CH$_2$CH$_2$CH$_2$CH$_2$CH$_2$CH$_2$—O—Ph-), 5.56 (S, 1H, CH$_2$=C(CH$_3$)—C(=O)—O—), 6.11 (S, 1H, CH$_2$=C(CH$_3$)—C(=O)—O—), 6.94 (d, 2H), 7.12 (s, 1H), 7.31 (d, 1H), 7.42 (s, 1H), 7.51 (d, 2H), 7.76 (d, 1H), 8.04 (s, 1H), (insg.9arom. CH), 11.57 (s, 1H, -Ph-OH—CH$_3$—C(CH$_3$)$_3$)

$^{13}$C-NMR (CDCl$_3$ 400 MHz): 18.3 (C=C(CH$_3$)—C(=O)—O—), 20.9 (-Ph-OH—CH$_3$—C(CH$_3$)$_3$), 25.8 (-Ph-OH—CH$_3$—C(CH$_3$)$_3$), 28.6~29.1 (O—CH$_2$CH$_2$(CH$_2$)$_3$CH$_2$—O-Ph), 29.5 (-Ph-OH—CH$_3$—C(CH$_3$)$_3$), 30.4 (O—CH$_2$CH$_2$(CH$_2$)$_4$—O-Ph), 35.4 (O—CH$_2$(CH$_2$)$_4$CH$_2$—O-Ph), 38.8 (O—CH$_2$(CH$_2$)$_4$CH$_2$—O-Ph), 113.7, 115.9, 117.7, 119.3, 128.7, 130.9, 136.5 (CH$_{arom}$), 125.2, 141.3, 143.3 (C$_{arom}$), 128.3 (C$_{arom}$—CH$_3$), 128.8 (C$_{arom}$—S), 136.4 (C$_{arom}$—S), 139.1 (C$_{arom}$—C(CH$_3$)$_3$), 146.7(C$_{arom}$—OH), 160.1(C$_{arom}$—O—), 125.4 (C=C(CH$_3$)—C(=O)—O—), 135.7 (C=C(CH$_3$)—C(=O)—O—), 167.8 (C=C(CH$_3$)—C(=O)—O—)

<Compound 7>

[Chemical Formula 21]

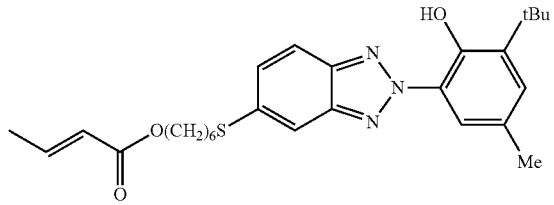

Intermediate 3 (2.00 g 4.84 mmol), crotonic acid (0.63 g 7.26 mmol) and p-toluenesulfonic acid (0.0912 g 0.48 mmol) were heated and stirred in 50 mL of toluene for 18 hours at 80-90° C. After the reaction was completed, the reaction mixture was stirred for 1 hour with addition of KYOWAAD® 500, filtered, and the filtrate was evaporated to obtain a yellow crude product, which was then recrystallized to synthesize Compound 7 as a light yellow solid. Physical property values thereof are shown below:

FT-IR (KBr): 2953 cm$^{-1}$: O—H stretching vibration 1719 cm$^{-1}$: C=O stretching vibration 1446, 1392 cm$^{-1}$: triazole ring stretching vibration $^1$H-NMR (CDCl$_3$ 400 MHz): δ 1.42-1.64 (m, 13H, —O—CH$_2$CH$_2$CH$_2$CH$_2$CH$_2$CH$_2$—S—, -Ph-OH—CH$_3$—C(CH$_3$)$_3$), 1.66 (quin, 2H, —O—CH$_2$CH$_2$CH$_2$CH$_2$CH$_2$—S—), 1.74 (quin, 2H, —O—CH$_2$CH$_2$CH$_2$CH$_2$CH$_2$CH$_2$—S—), 1.87 (S, 3H, CH$_3$CH=CH—C(=O)—O—), 2.38 (s, 3, -Ph-OH—CH$_3$—C(CH$_3$)$_3$), 3.03 (t, 2H, —O—CH$_2$CH$_2$CH$_2$CH$_2$CH$_2$—S—), 4.14 (t, 2H, —O—CH$_2$CH$_2$CH$_2$CH$_2$CH$_2$CH$_2$—S—) 5.82 (d, 1H, CH$_3$CH=CH—C(=O)—O—), 6.97 (quin, 1H, CH$_3$CH=CH—C(=O)—O—), 7.16 (s, 1H), 7.35 (d, 1H), 7.70 (s, 1H), 7.81 (d, 1H), 8.04 (S, 1H), (insg.5arom. CH), 11.59 (s, 1H, -Ph-OH—CH$_3$—C(CH$_3$)$_3$)

$^{13}$C-NMR (CDCl$_3$ 400 MHz): δ 18.0 (CH$_3$C=C—C(=O)—O—), 20.9 (-Ph-OH—CH$_3$—C(CH$_3$)$_3$), 25.6 (-Ph-OH—CH$_3$—C(CH$_3$)$_3$), 28.5~28.5 (CH$_3$C=C—C(=O)—O—CH$_2$CH$_2$(CH$_2$)CH$_2$—S), 29.5 (-Ph-OH—CH$_3$—C(CH$_3$)$_3$), 33.1 (CH$_3$C=C—C(=O)—O—(CH$_2$)$_4$CH$_2$CH$_2$—S), 35.4 (CH$_3$C=C—C(=O)—O—(CH$_2$)$_5$CH$_2$—S), 64.1 (CH$_3$C=C—C(=O)—O—CH(CH$_2$)$_5$—S), 113.8, 117.6, 119.3, 128.7, 129.3 (CH$_{arom}$), 125.4, 141.2, 143.2 (C$_{arom}$), 128.3 (C$_{arom}$—CH$_3$), 137.8(C$_{arom}$—S), 139.1(C$_{arom}$—C(CH$_3$)$_3$), 146.8 (C$_{arom}$—OH) 122.8 (CH$_3$C=C—C(=O)—O—), 144.5 (CH$_3$C=C—C(=O)—O—), 166.6 (CH$_3$C=C—C(=O)—O—)

<Compound 8>

[Chemical Formula 22]

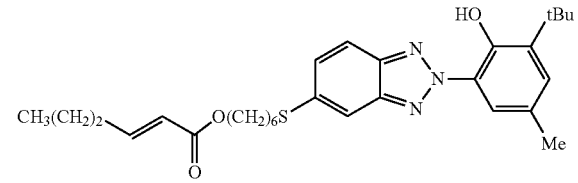

Intermediate 3 (1.00 g 4.4 mmol), 2-hexenic acid (0.42 g 7.26 mmol), and p-toluenesulfonic acid (0.0461 g 0.48 mmol) were heated and stirred in 50 mL of toluene for 18 hours at 80-90° C. After the reaction was completed, the reaction mixture was stirred for 1 hour with addition of KYOWAAD® 500, filtered, and the filtrate was evaporated to obtain a yellow crude product, which was then recrystallized to synthesize Compound 8 as a light yellow solid. Physical property values thereof are shown below:

FT-IR (KBr): 2956 cm$^{-1}$: O—H stretching vibration 1715 cm$^{-1}$: C=O stretching vibration 1446, 1391 cm$^{-1}$: triazole ring stretching vibration $^1$H-NMR (CDCl$_3$ 400 MHz): δ0.92 (m, 3H, CH$_3$CH$_2$CH$_2$CH=CH$_3$—C(=O)—O—), 1.49-1.55 (m, 15H, —O—CH$_2$CH$_2$CH$_2$CH$_2$CH$_2$CH$_2$—S—, CH$_3$CH$_2$CH$_2$CH=CH—C(=O)—O—, -Ph-OH—CH$_3$—C(CH$_3$)$_3$), 1.68 (quin, 2H, —O—CH$_2$CH$_2$CH$_2$CH$_2$CH$_2$—S—), 1.75 (quin, 2H, —O—CH$_2$CH$_2$CH$_2$CH$_2$CH$_2$CH$_2$—S—), 2.17(q, 2H, CH$_3$CH$_2$C̲H$_2$CH=CH—C(=O)—O—), 2.38 (s, 3H, -Ph-OH—CH̲$_3$—C(CH$_3$)$_3$), 3.04 (t, 2H, —O—CH$_2$CH$_2$CH$_2$CH$_2$CH$_2$C̲H$_2$—S—), 4.13 (t, 2H, —O—C̲H$_2$CH$_2$CH$_2$CH$_2$CH$_2$CH$_3$—S—) 5.83 (d, 1H, CH$_3$(CH$_2$)$_2$CH=C̲H—C(=O)—O—), 6.96 (S, 1H, CH$_3$(CH$_2$)$_2$C̲H=CH—C(=O)—O—), 7.17 (s, 1H), 7.36 (d, 1H), 7.71 (s, 1H), 7.82 (d, 1H), 8.05 (s, 1H), (insg.5arom. C H̲), 11.60 (s, 1H, -Ph-OH̲—CH$_3$—C(CH$_3$)$_3$)

$^{13}$C-NMR (CDCl$_3$ 400 MHz): δ 13.7 (C̲H$_3$(CH$_2$)$_2$C=C—C(=O)—O—), 20.9 (-Ph-OH—C̲H$_3$—C(CH$_3$)$_3$), 25.6 (-Ph-OH—CH$_3$—C̲(CH$_3$)$_3$), 28.6~28.6 (CH$_3$(CH$_2$)$_2$C=C—C(=O)—O—CH$_2$CH$_2$(C̲H$_2$)$_3$CH$_2$—S), 29.5 (-Ph-OH—CH$_3$—C(C̲H$_3$)$_3$), 34.2 (CH$_3$(CH$_2$)$_2$C=C—C(=O)—O—(CH$_2$)$_4$C̲H$_2$CH$_2$—S), 35.4 (CH$_3$(CH$_2$)$_2$C=C—C(=O)—O—(CH$_2$)$_5$C̲H$_2$—S), 64.1 (CH$_3$(CH$_2$)$_2$C=C—C(=O)—O—C̲H$_2$(CH$_2$)$_5$—S), 113.8, 117.6, 119.3, 128.7, 129.3 (C̲H$_{arom}$), 125.4, 141.2, 143.4 (C̲$_{arom}$), 128.3 (C$_{arom}$—C̲H$_3$), 137.8(C̲$_{arom}$—S), 139.1 (C̲$_{arom}$—C(CH$_3$)$_3$), 149.3 (C̲$_{arom}$—OH) 121.3 (CH$_3$(CH$_2$)$_2$=C̲—C(=O)—O—), 146.7 (CH$_3$(CH$_2$)$_2$C̲=C—C(=O)—O—), 166.8 (CH$_3$(CH$_2$)$_2$C=C—C̲(=O)—O—)

<Compound 9>

[Chemical Formula 23]

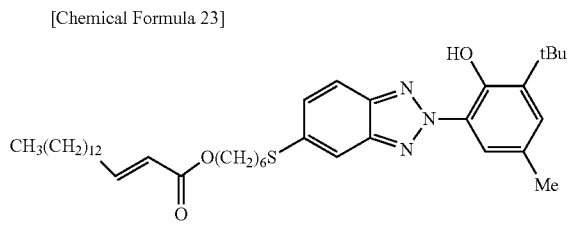

Intermediate 3 (0.27 g 0.66 mmol), 2-hexadecenoic acid (0.25 g 0.98 mmol), and p-toluenesulfonic acid (0.0125 g 0.0655 mmol) were heated and stirred in 15 mL of toluene for 18 hours at 80-90° C. After the reaction was completed, the reaction mixture was stirred for 1 hour with the addition of KYOWAAD® 500, filtered, and the filtrate was evaporated to obtain a crude product in a liquid state, followed by column purification thereof to obtain Compound 9 as a light yellow viscous liquid. Physical property values thereof are shown below:

FT-IR (KBr): 2925 cm$^{-1}$: O—H stretching vibration 1723 cm$^{-1}$: C=O stretching vibration 1464, 1391 cm$^{-1}$: triazole ring stretching vibration $^1$H-NMR (CDCl$_3$ 400 MHz): δ0.94(t, 3H, C H̲$_3$CH$_2$CH$_2$CH=CH—C(=O)—O—), 1.32-1.57(m, 35H, —O—CH$_2$CH$_2$C̲H$_2$C̲H$_2$CH$_2$CH$_2$—S—, CH$_3$(C H̲$_2$)$_{11}$CH$_2$CH=CH—C(=O)—O—, -Ph-OH—CH$_3$—C(C H̲$_3$)$_3$), 1.68 (quin, 2H, —O—CH$_2$C H̲$_2$CH$_2$CH$_2$CH$_2$—S—), 1.75 (quin, 2H, —O—CH$_2$CH$_2$CH$_2$CH$_2$C H̲$_2$—S—), 2.17(q, 2H, CH$_3$(CH$_2$)$_{11}$C̲H$_2$CH=CH—C(=O)—O—), 2.38 (s, 3H, -Ph-OH—CH̲$_3$—C(CH$_3$)$_3$), 3.04 (t, 2H, —O—CH$_2$CH$_2$CH$_2$CH$_2$CH$_2$C H̲$_2$—S—), 4.14 (t, 21, —O—C̲H$_2$CH$_2$CH$_2$CH$_2$CH$_2$CH$_2$—S—) 6.96 (d, 1H, CH$_3$(CH$_2$)$_{12}$CH=C H̲—C(=O)—O—), 7.53 (q, 1H, CH$_3$(CH$_2$)$_{12}$C H̲=CH—C(=O)—O—), 7.17 (s, 1H), 7.36 (d, 1H), 7.71 (s, 1H), 7.82 (d, 1H), 8.05 (s, 1H), (insg.5arom. C H̲), 11.60 (s, 1H, -Ph-OH̲—CH$_3$—C(CH$_3$)$_3$)

$^{13}$C-NMR (CDCl$_3$ 400 MHz): δ 14.0 (C̲H$_3$(CH$_2$)$_{12}$C=C—C(=O)—O—), 20.9 (-Ph-OH—C̲H$_3$—C(CH$_3$)$_3$), 23.0 (CH$_3$C̲H$_2$CH$_2$(CH$_2$)$_{10}$C=C—C(=O)—O—), 25.6(-Ph-OH—CH$_3$—C̲(CH$_3$), 28.0~30.4 (CH$_3$CH$_2$CH$_2$(C̲H$_2$)$_9$CH$_2$C=C—C(=O)—O—), 28.5~28.6 (CH$_3$(CH$_2$)$_{12}$C=C—C(=O)—O—CH$_2$CH$_2$(C̲H$_2$)$_3$CH$_2$—S), 29.5 (-Ph-OH—CH$_3$—C(C̲H$_3$)$_3$), 31.9 (CH$_3$CH$_2$C̲H$_2$(CH$_2$)$_{10}$C=C—C(=O)—O—), 32.2 (CH$_3$(CH$_2$)$_{11}$C̲H$_2$C=C—C(=O)—O—), 33.1 (CH$_3$(CH$_2$)$_{12}$C=C—C(=O)—O—(CH$_2$)$_4$C̲H$_2$CH$_2$—S), 35.4 (CH$_3$(CH$_2$)$_{12}$C=C—C(=O)—O—(CH$_2$)$_5$C̲H$_2$—S), 64.1 (CH$_3$(CH$_2$)$_{12}$C=C—C(=O)—O—C̲H$_2$(CH$_2$)$_5$—S), 113.8, 117.6, 119.3, 128.7, 129.3 (C̲H$_{arom}$), 125.4, 141.2, 143.4 (C̲$_{arom}$), 128.3 (C$_{arom}$—C̲H$_3$), 137.8(C̲$_{arom}$—S), 139.1 (C̲$_{arom}$—C(CH$_3$)$_3$), 149.7 (C̲$_{arom}$—OH) 121.1 (CH$_3$(CH$_2$)$_{12}$=C̲—C(=O)—O—), 146.7 (CH$_3$(CH$_2$)$_{12}$C̲=C—C(=O)—O—), 166.9 (CH$_3$(CH$_2$)$_{12}$C=C—C̲(=C—)—O—)

<Compound 13>

[Chemical Formula 24]

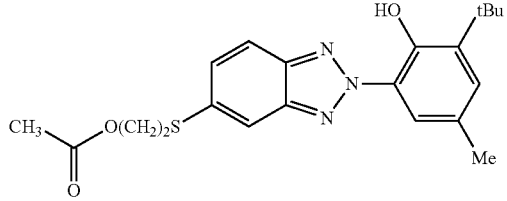

Intermediate 1 (0.40 g 1.21 mmol), acetyl chloride (0.18 g 0.18 mmol) and triethylamine (0.19 g 2.46 mmol) were stirred in 15 mL of methylene chloride for 18 hours at room temperature. After the reaction was completed, water and chloroform were added, and then acid treatment and water washing thereof were performed, and the organic layer was evaporated to obtain a crude product. The crude product thus obtained was subjected to column purification and recrystallization to obtain Compound 13 as alight yellow solid. Physical property values thereof are shown below:

FT-IR (KBr): 3011 cm$^{-1}$: O—H stretching vibration 1744 cm$^{-1}$: C=O stretching vibration 1448, 1361 cm$^{-1}$: triazole ring stretching vibration $^1$H-NMR (CDCl$_3$ 400 MHz): δ 1.49(s, 9H, -Ph-OH—CH$_3$—C(C H̲$_3$)$_3$), 2.05(s, 3H, C H̲$_3$—C=O—O—), 2.39 (s, 3H, -Ph-OH—C H̲$_3$—C(CH$_3$)$_3$), 3.28 (t, 2H, —C=O—O—CH$_2$C H̲$_2$—S), 4.33 (t, 2H, —C=O—O—C H̲$_2$CH$_2$—S) 7.13 (d, 2H), 7.74 (s, 1H), 7.83 (d, 1H), 7.87 (s, 1H), 8.06 (s, 1H), (insg.5arom. C H̲), 11.62 (s, 1H, -Ph-O H̲—CH$_3$—C(CH$_3$)$_3$)

$^{13}$C-NMR (CDCl$_3$ 400 MHz): δ 20.8 (-Ph-OH—C̲H$_3$—C(CH$_3$)$_3$), 20.9 (-Ph-OH—CH$_3$—C̲(CH$_3$)$_3$), 29.6 (-Ph-OH—CH$_3$—C(C̲H$_3$)$_3$), 32.2 (—C=O—O—CH$_2$C̲H$_2$—S), 35.4 (C̲H$_3$—C(=O)—O—), 62.5 (—C=O—O—C̲H$_2$CH$_2$—S)

115.8, 118.0, 119.4, 128.4, 135.8 (C̲H$_{arom}$), 125.4, 141.6, 143.3 (C̲$_{arom}$), 128.9 (C$_{arom}$—C̲H$_3$), 129.7 (C̲$_{arom}$—S), 139.2 (C̲$_{arom}$—C(CH$_3$)$_3$), 146.9(C$_{arom}$—OH), 170.7 (CH$_3$—C̲=O—O—)

<Compound 14>

[Chemical Formula 25]

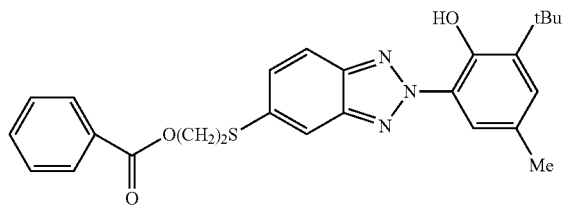

Intermediate 1 (2.00 g 5.59 mmol), benzoyl chloride (1.18 g 8.39 mmol) and triethylamine (0.89 g 11.19 mmol) were stirred in 30 mL of methylene chloride for 18 hours at room temperature. After the reaction was completed, water and chloroform were added, and acid treatment and water washing thereof were performed, and the organic layer was evaporated to obtain a crude product. The crude product thus obtained was subjected to column purification and recrystallized to obtain Compound 14 as a light yellow solid. Physical property values thereof are shown below:

FT-IR (KBr): 2963 cm$^{-1}$: O—H stretching vibration 1719 cm$^{-1}$: C=O stretching vibration 1449, 1357 cm$^{-1}$: triazole ring stretching vibration $^1$H-NMR (CDCl$_3$ 400 MHz): δ 1.50 (s, 9H, -Ph-OH—CH$_3$—C(CH$_3$)$_3$), 2.39 (s, 3H, -Ph-OH—CH$_3$—C(CH$_3$)$_3$), 3.41 (t, 2H, —C=O—O—CH$_2$CH$_2$—S), 4.59 (t, 2H, —C=O—O—CH$_2$CH$_2$—S) 7.19 (s, 1H), 7.38 (t, 2H), 7.45 (d, 1H), 7.50 (t, 1H), 7.81 (d, 1H), 7.91~7.96 (m, 3H), 8.05 (s, 1H), (insg.10arom. CH), 11.54 (s, 1H, -Ph-OH—CH$_3$—C(CH$_3$)$_3$)

$^{13}$C-NMR (CDCl$_3$ 400 MHz): δ 20.9 (-Ph-OH—CH$_3$—C(CH$_3$)$_3$), 29.6 (-Ph-OH—CH$_3$—C(CH$_3$)$_3$), 32.5 (—C=O—O—CH$_2$CH$_2$—S), 35.4 (-Ph-OH—CH$_3$—C(CH$_3$)$_3$), 63.4 (—C=O—O—CH$_2$CH$_2$—S) 116.3, 118.0, 119.4, 128.3, 128.9, 129.8, 133.1, 135.8 (CH$_{arom}$), 125.4, 141.6, 143.3 (C$_{arom}$), 128.3 (C$_{arom}$—CH$_3$), 129.7 (C$_{arom}$—S), 139.2 (C$_{arom}$—C(CH$_3$)$_3$), 146.8(C$_{arom}$—OH), 166.3 (Ph-C(=O)—O—)

<Compound 15>

[Chemical Formula 26]

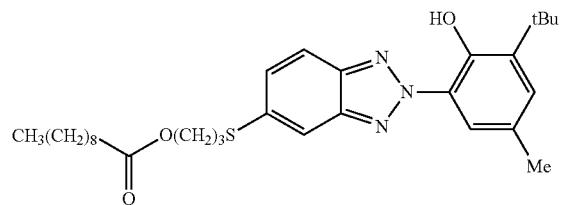

Intermediate 2 (0.50 g 1.35 mmol), decanoic acid (0.35 g 2.02 mmol) and p-toluenesulfonic acid (0.0256 g 0.14 mmol) were heated and stirred in 15 mL of toluene for 18 hours at 80-90° C. After the reaction was completed, the reaction mixture was stirred for 1 hour with the addition of KYOWAAD® 500, filtered, and the filtrate was evaporated to obtain a crude product. The crude product thus obtained was subjected to column purification to synthesize a light yellow solid Compound 15. Physical property values thereof are shown below:

FT-IR (KBr): 3339 cm$^{-1}$: O—H stretching vibration 1685 cm$^{-1}$: C=O stretching vibration 1470, 1359 cm$^{-1}$: triazole ring stretching vibration $^1$H-NMR (CDCl$_3$ 400 MHz): δ0.87 (t, 3H, CH$_3$(CH$_2$)$_6$—C=O—O—), 1.25 (m, 8H, CH$_3$(CH$_2$)$_4$CH$_2$CH$_2$—C=O—O—), 1.49 (s, 9H, -Ph-OH—CH$_3$—C(CH$_3$)$_3$), 1.63 (quin, 4H, CH$_3$(CH$_2$)$_{13}$CH$_2$CH$_2$CH$_2$—C=O—O—CH$_2$CH$_2$(CH$_2$)$_4$—S), 1.73 (quin, 2H, —C=O—O—CH$_2$CH$_2$CH$_2$—S), 2.06 (quin, 2H, CH$_3$(CH$_2$)$_4$CH$_2$CH$_2$—C=O—O—), 2.38 (s, 3H, -Ph-OH—CH$_3$—C(CH$_3$)$_3$), 3.11(t, 2H, —C=O—O—CH$_2$CH$_2$CH$_2$—S), 4.23 (t, 2H, —C=O—O—CH$_2$CH$_2$CH$_2$—S), 7.17 (s, 1H), 7.37 (s, 1H), 7.75 (d, 1H), 7.81 (d, 1H), 8.05 (s, 1H), (insg.5arom. CH), 11.58 (s, 1H, -Ph-OH—CH$_3$—C(CH$_3$)$_3$)

$^{13}$C-NMR (CDCl$_3$ 400 MHz): 14.1 (CH$_3$(CH$_2$)$_6$—C=O—O—), 20.9 (-Ph-OH—CH$_3$—C(CH$_3$)$_3$), 22.7 (CH$_3$CH$_2$(CH$_2$)$_5$—C=O—O—), 25.0 (-Ph-OH—CH$_3$—C(CH$_3$)$_3$), 28.1 (-Ph-OH—CH$_3$—C(CH$_3$)$_3$), 29.3~29.6 (CH$_3$CH$_2$(CH$_2$)$_3$CH$_2$CH$_2$—C=O—O—), 28.1 (-Ph-OH—CH$_3$—C(CH$_3$)$_3$), 30.0 (—C=O—O—CH$_2$CH$_2$CH$_2$—S), 31.9 (CH$_3$(CH$_2$)$_4$CH$_2$CH$_2$—C=O—O—), 34.3 (CH$_3$(CH$_2$)$_5$CH$_2$—C=O—O—), 35.4(—C=O—O—CH$_2$CH$_2$CH$_2$—S), 62.5 (—C=O—O—CH$_2$CH$_2$CH$_2$—S), 114.7, 117.8, 119.4, 128.3, 136.9 (CH$_{arom}$), 125.4, 141.4, 143.4 (C$_{arom}$), 128.8 (C$_{arom}$—CH$_3$), 129.5 (C$_{arom}$—S), 139.2 (C$_{arom}$—C(CH$_3$)$_3$), 146.7(C$_{arom}$—OH), 173.8 (CH$_3$(CH$_2$)$_{16}$—C=O—O—)

<Compound 16>

[Chemical Formula 27]

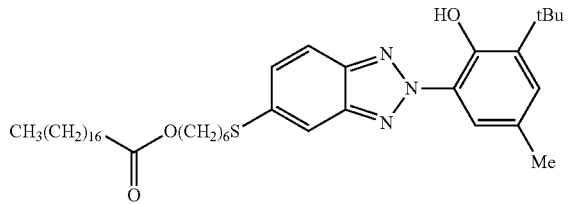

Intermediate 3(0.30 g 0.73 mmol), stearic acid (0.31 g 1.10 mmol) and p-toluenesulfonic acid (0.013 g 0.073 mmol) were heated and stirred in 5 mL of toluene for 18 hours at 80-90° C. After the reaction was completed, the reaction mixture was stirred for 1 hour with the addition of KYOWAAD® 500, filtered, and the filtrate was evaporated to obtain a crude product. The crude product thus obtained was recrystallized to synthesize a light yellow solid Compound 16. Physical property values thereof are shown below:

FT-IR (KBr): 2917 cm$^{-1}$: O—H stretching vibration 1733 cm$^{-1}$: C=O stretching vibration 1463, 1376 cm$^{-1}$: triazole ring stretching vibration $^1$H-NMR (CDCl$_3$ 400 MHz): δ0.89 (t, 3H, CH$_3$(CH$_2$)$_{16}$—C=O—O—), 1.27 (m, 28H, CH$_3$(CH$_2$)$_{13}$CH$_2$CH$_2$CH$_2$—C=O—O—(CH$_2$)$_2$CH$_2$CH$_2$(CH$_2$)$_2$—S), 1.41 (quin, 2H, CH$_3$(CH$_2$)$_{13}$CH$_2$CH$_2$CH$_2$—C=O—O—), 1.49 (m, 11H, —C=O—O—(CH$_2$)$_2$CH$_2$CH$_2$(CH$_2$)$_2$—S-Ph-OH—CH$_3$—C(CH$_3$)$_3$), 1.60 (quin, 4H, CH$_3$(CH$_2$)$_{13}$CH$_2$CH$_2$CH$_2$—C=O—O—CH$_2$CH$_2$(CH$_2$)$_4$—S), 1.73 (quin, 2H, —C=O—O—(CH$_2$)$_4$CH$_2$CH$_2$—S), 2.28 (t, 2H, CH$_3$(CH$_2$)$_{13}$CH$_2$CH$_2$CH$_2$—C=O—O—), 2.38 (s, 3H, -Ph-OH—CH$_3$—C(CH$_3$)$_3$), 3.03 (t, 2H, —C=O—O—(CH$_2$)$_5$CH$_2$—S), 4.01 (t, 2H, —C=O—O—CH$_2$(CH$_2$)$_5$—S), 7.16 (s, 2H), 7.35 (s, 1H), 7.70 (d, 1H), 7.1(d, 1H), 8.04 (s, 1H), 7.76 (d, 1H), 8.04 (s, 1H), (insg.9arom. CH), 11.60 (s, 1H, -Ph-OH—CH$_3$—C(CH$_3$)$_3$)

$^{13}$C-NMR (CDCl$_3$ 400 MHz): 14.5 (CH$_3$(CH$_2$)$_{16}$—C=O—O—), 20.9 (-Ph-OH—CH$_3$—C(CH$_3$)$_3$), 23.1(CH$_3$CH$_2$(CH$_2$)$_{15}$—C=O—O—), 25.1 (CH$_3$(CH$_2$)$_{13}$CH$_2$CH$_2$—C=O—O—), 25.8 (-Ph-OH—CH$_3$—C(CH$_3$)$_3$), 28.5~29.7 (CH$_3$ CH$_2$(CH$_2$)$_{13}$CH$_2$CH$_2$—C=O—O—CH$_2$CH$_2$(CH$_2$)$_3$CH$_2$—S), 29.7 (-Ph-OH—CH$_3$—C(CH$_3$)$_3$), 31.9 (—C=O—O—CH$_2$CH$_2$(CH$_2$)$_4$—S), 33.4 (CH$_3$(CH$_2$)$_{14}$CH$_2$CH$_2$—C=O—O—), 34.4 (CH$_3$(CH$_2$)$_{15}$CH$_2$—C=O—O—), 35.8 (—C=O—O—(CH$_2$)$_5$CH$_2$—S), 64.1 (—C=O—O—CH$_2$(CH$_2$)$_5$—S), 113.7, 117.6, 119.3, 128.3, 137.3(CH$_{arom}$), 125.4, 141.2, 143.4(C$_{arom}$), 128.7 (C$_{arom}$—CH$_3$), 129.3 (C$_{arom}$—S), 139.1(C$_{arom}$—C(CH$_3$)$_3$), 146.7(C$_{arom}$—OH), 174.0 (CH$_3$(CH$_2$)$_{16}$—C=O—O—)

<Compound 17>

[Chemical Formula 28]

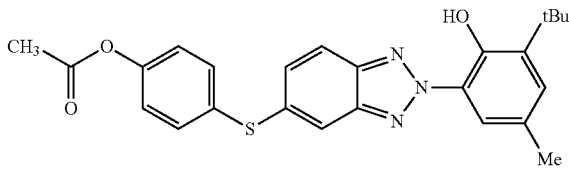

Intermediate 4(0.40 g 0.99 mmol), acetyl chloride (0.16 g 1.97 mmol) and triethylamine (0.17 g 2.18 mmol) were stirred in 30 mL of methylene chloride for 18 hours at room temperature. After the reaction was completed, water and chloroform were added, and then acid treatment and water washing thereof were performed, and the organic layer was evaporated to obtain a crude product. The crude product thus obtained was subjected to column purification and recrystallized to obtain Compound 17 as a light yellow solid. Physical property values thereof are shown below:

FT-IR (KBr): 2968 cm$^{-1}$: O—H stretching vibration 1762 cm$^{-1}$: C=O stretching vibration 1448, 1367 cm$^{-1}$: triazole ring stretching vibration $^1$H-NMR (CDCl$_3$ 400 MHz): δ 1.48 (s, 9H, -Ph-OH—CH$_3$—C(CH$_3$)$_3$), 2.32(s, 3H, CH$_3$—C=O—), 2.37 (s, 3H, -Ph-OH—CH$_3$—C(CH$_3$)$_3$), 7.12 (d, 2H), 7.17(s, 1), 7.35 (d, 1H), 7.48 (d, 2H), 7.70 (s, 1H), 7.82 (d, 1H), 8.04 (s, 1H), (insg.9arom. CH), 11.54 (s, 1H, -Ph-OH—CH$_3$—C(CH$_3$)$_3$)

$^{13}$C-NMR (CDCl$_3$ 400 MHz): δ 20.9 (-Ph-OH—CH$_3$—C(CH$_3$)$_3$), 21.1 (-Ph-OH—CH$_3$—C(CH$_3$)$_3$), 29.5 (-Ph-OH—CH$_3$—C(CH$_3$)$_3$), 35.4 (CH$_3$—C(=O)—O—), 116.9, 118.1, 119.4, 122.9, 128.9, 129.7, 133.9 (CH$_{arom}$), 125.4, 141.7, 143.2 (C$_{arom}$), 128.3 (C$_{arom}$—CH$_3$), 130.9 (C$_{arom}$—S), 137.1 (C$_{arom}$—S), 139.2 (C$_{arom}$—C(CH$_3$)$_3$), 146.7(C$_{arom}$—OH), 150.8(C$_{arom}$—O—), 169.1(CH$_3$—C(=O)—O—)

<Compound 18>

[Chemical Formula 29]

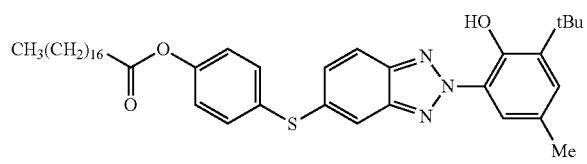

Intermediate 4(0.40 g 0.99 mmol), stearyl chloride (0.60 g 1.97 mmol) and triethylamine (0.17 g 2.18 mmol) were stirred in 30 mL of methylene chloride for 18 hours at room temperature. After the reaction was completed, water and chloroform were added, and then acid treatment and water washing thereof were performed, and the organic layer was evaporated to obtain a crude product. The crude product thus obtained was subjected to column purification and recrystallized to obtain Compound 18 as a light yellow solid. Physical property values thereof are shown below:

FT-IR (KBr): 2918 cm$^{-1}$: O—H stretching vibration 1756 cm$^{-1}$: C=O stretching vibration 1471, 1376 cm$^{-1}$: triazole ring stretching vibration $^1$H-NMR (CDCl$_3$ 400 MHz): δ0.88 (t, 3H, CH$_3$(CH$_2$)$_{16}$—C=O—O—), 1.25 (m, 26H, CH$_3$(CH$_2$)$_{13}$CH$_2$CH$_2$CH$_2$—C=O—O—), 1.41 (quin, 2H, CH$_3$(CH$_2$)$_{13}$CH$_2$CH$_2$CH$_2$—C=O—O—), 1.48 (m, 9H, -Ph-OH—CH$_3$—C(CH$_3$)$_3$), 1.78 (quin, 2H, CH$_3$(CH$_2$)$_{13}$CH$_2$CH$_2$—C=O—O—), 2.36 (s, 3H, -Ph-OH—CH$_3$—C(CH$_3$)$_3$), 2.56 (t, 2H, CH$_3$(CH$_2$)$_{13}$CH$_2$CH$_2$CH$_2$—C=O—O—), 7.11 (d, 2H), 7.13 (s, 1H), 7.34 (d, 1H), 7.48 (d, 2H), 7.68 (s, 1H), 7.80 (d, 1H), 8.03 (s, 1H), (insg.9arom. CH), 11.54 (s, 1, -Ph-OH—CH$_3$—C(CH$_3$)$_3$)

$^{13}$C-NMR (CDCl$_3$ 400 MHz): 14.1 (CH$_3$(CH$_2$)$_{16}$—C=O—O—), 20.9 (-Ph-OH—CH$_3$—C(CH$_3$)$_3$), 22.7 (CH$_3$CH$_2$(CH$_2$)$_{15}$—C=O—O—), 24.9(-Ph-OH—CH$_3$—C(CH$_3$)$_3$), 29.1~29.7 (CH$_3$(CH$_2$)$_{13}$CH$_2$(CH$_2$)$_2$—C=O—O—), 29.7 (-Ph-OH—CH$_3$—C(CH$_3$)$_3$), 31.9 (CH$_3$(CH$_2$)$_{13}$CH$_2$(CH$_2$)$_2$—C=O—O—), 34.4 (CH$_3$(CH$_2$)$_{14}$CH$_2$CH$_2$—C=O—O—), 35.4 (CH$_3$(CH$_2$)$_{15}$CH$_2$—C=O—O—), 116.7, 118.1, 119.4, 122.9, 128.9, 129.6, 134.0 (CH$_{arom}$), 125.4, 141.6, 143.2 (C$_{arom}$), 128.3 (C$_{arom}$—CH$_3$), 130.6 (C$_{arom}$—S), 137.3 (C$_{arom}$—S), 139.2 (C$_{arom}$—C(CH$_3$)$_3$), 146.8(C$_{arom}$—OH), 150.8(C$_{arom}$—O—), 172.0 (CH$_3$(CH$_2$)$_{16}$—C(=O)—O—)

<Compound 19>

[Chemical Formula 30]

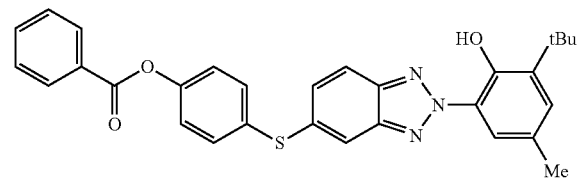 [SMILES: Cc1cc(-n2nc3ccc(Sc4ccc(OC(=O)c5ccccc5)cc4)cc3n2)c(O)c(C(C)(C)C)c1]

Intermediate 4 (0.40 g 0.99 mmol), benzoyl chloride (0.28 g 1.97 mmol) and triethylamine (0.17 g 2.18 mmol) were stirred in 30 mL of methylene chloride for 18 hours at room temperature. After the reaction was completed, water and chloroform were added, acid treatment water washing thereof were performed, and the organic layer was evaporated to obtain a crude product. The crude product thus obtained was subjected to column purification and recrystallized to obtain Compound 19 as a light yellow solid. Physical property values thereof are shown below:

FT-IR (KBr): 2962 cm$^{-1}$: O—H stretching vibration 1738 cm$^{-1}$: C=O stretching vibration 1487, 1355 cm$^{-1}$: triazole ring stretching vibration $^1$H-NMR (CDCl$_3$ 400 MHz): δ 1.49 (s, 9H, -Ph-OH—CH$_3$—C(CH$_3$)$_3$), 2.37 (s, 3, -Ph-OH—CH$_3$—C(CH$_3$)$_3$), 7.16 (s, 2H), 7.25 (d, 2H), 7.36 (d, 1H), 7.50~7.56 (m, 4H), 7.63 (t, 1H), 7.72 (s, 1H), 8.04 (s, 1H), 8.20 (d, 1H), (insg.14arom. CH), 11.56 (s, 1H, -Ph-OH—CH$_3$—C(CH$_3$)$_3$)

$^{13}$C-NMR (CDCl$_3$ 400 MHz): δ20.9 (-Ph-OH—CH$_3$—C(CH$_3$)$_3$), 29.5 (-Ph-OH—CH$_3$—C(CH$_3$)$_3$), 35.4 (-Ph-OH—CH$_3$—C(CH$_3$)$_3$), 116.9, 118.1, 119.4, 123.1, 128.7, 128.9, 129.7, 130.2, 133.8, 134.0 (CH$_{arom}$), 125.4, 141.7, 143.2 (C$_{arom}$), 128.3 (C$_{arom}$—CH$_3$), 129.3 (C$_{arom}$—C(=O)—O-Ph), 131.0 (C$_{arom}$—S), 137.1 (C$_{arom}$—S), 139.2 (C$_{arom}$—C(CH$_3$)$_3$), 146.8(C$_{arom}$—OH), 151.1(Ph-C(=O)—O—C$_{arom}$), 164.9 (Ph-C(=O)—O—)

<Compound 20>

[Chemical Formula 31]

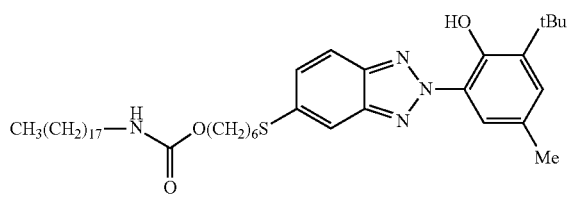

Intermediate 3 (5.00 g 12.10 mmol) and octadecyl isocyanate (4.69 g 12.71 mmol) were heated and stirred in 50 mL of chlorobenzene/O-dichlorobenzene (80/20) for 8 hours at 130° C. After the reaction was completed, MeOH was added and the precipitated crystals were filtered to obtain a yellow crude product. The crude product thus obtained was subjected to column purification and recrystallized to synthesize a light yellow solid Compound 20. Physical property values thereof are shown below:

FT-IR (KBr): FT-IR (KBr): 3065 cm$^{-1}$: O—H stretching vibration 1685 cm$^{-1}$: C=O stretching vibration 1470, 1359 cm$^{-1}$: triazole ring stretching vibration $^1$H-NMR (CDCl$_3$ 400 MHz): δ0.88 (t, 3H, CH$_3$(CH$_2$)$_{17}$—HNC(=O)—O—), 1.24 (m, 28H, CH$_3$(CH$_2$)$_{13}$CH$_2$CH$_2$CH$_2$—HNC(=O)—O—(CH$_2$)$_2$CH$_2$CH$_2$(CH$_2$)$_2$—S), 1.41~1.49 (m, 13H, CH$_3$(CH$_2$)$_{13}$CH$_2$CH$_2$CH$_2$—HNC(=O)—O—(CH$_2$)$_2$CH$_2$CH$_2$(CH$_2$)$_2$—S-Ph-OH—CH$_3$—C(CH$_3$)$_3$), 1.62 (m, 2H, —HNC(=O)—O—CH$_2$CH$_2$(CH$_2$)$_4$—S), 1.75(t, 2H, quin, 2H, —HNC(=O)—O—(CH$_2$)$_4$CH$_2$CH$_2$—S), 2.38(s, 3H, -Ph-OH—CH$_3$—C(CH$_3$)$_3$), 3.03 (m, 2H, —HNC(=O)—O—(CH$_2$)$_5$CH$_2$—S), 3.13 (m, 2H, CH$_3$(CH$_2$)$_{13}$CH$_2$CH$_2$CH$_2$—HNC(=O)—O—), 4.01(t, 2H, —HNC(=O)—O—CH$_2$(CH$_2$)$_5$—S), 4.61(m, 1H, —HNC(=O)—O—), 7.16 (s, 1H), 7.35 (d, 1H), 7.70 (s, 1H), 7.81 (d, 1H), 8.05 (s, 1H), (insg.5arom. CH), 11.60 (s, 1H, -Ph-OH—CH$_3$—C(CH$_3$)$_3$)

$^{13}$C-NMR (CDCl$_3$ 400 MHz): δ14.1 (CH$_3$(CH$_2$)$_{17}$—HNC(=O)—O—), 20.9 (-Ph-OH—CH$_3$—C(CH$_3$)$_3$), 22.7 (CH$_3$CH$_2$(CH$_2$)$_{16}$—HNC(=O)—O—), 25.5 (-Ph-OH—CH$_3$—C(CH$_3$)$_3$), 26.8 (CH$_3$(CH$_2$)$_{14}$CH$_2$CH$_2$CH$_2$—C=O—O—), 28.6~29.7 (CH$_3$CH$_2$(CH$_2$)$_{14}$CH$_2$CH$_2$—HNC(=O)—O—CH$_2$CH$_2$(CH$_2$)$_3$CH$_2$—S), 29.7(-Ph-OH—CH$_3$—C(CH$_3$)$_3$), 31.9 (—HNC(=O)—O—CH$_2$CH$_2$(CH$_2$)$_4$—S), 33.2 (CH$_3$(CH$_2$)$_{15}$CH$_2$CH$_2$—HNC(=O)—O—), 35.4 (—HNC(=O)—O—(CH$_2$)$_5$CH$_2$—S), 41.1 (CH$_3$(CH$_2$)$_{16}$CH$_2$—HNC(=O)—O—), 64.6 (—HNC(=O)—O—CH$_2$(CH$_2$)$_5$—S), 113.9, 117.6, 119.3, 128.3, 137.8 (CH$_{arom}$), 125.5, 141.3, 143.4 (C$_{arom}$), 128.7 (C$_{arom}$—CH$_3$), 129.4 (C$_{arom}$—S), 139.2 (C$_{arom}$—C(CH$_3$)$_3$), 146.7(C$_{arom}$—OH), 156.0 (—HNC(=O)—O—)

<Compound 21>

[Chemical Formula 32]

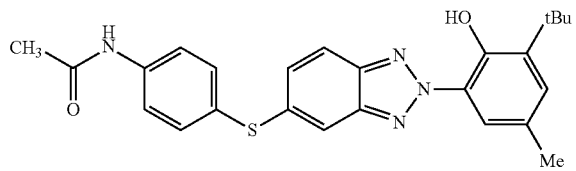

2-(2-hydroxy-3-tert-butyl-5-methylphenyl)-5-chlorobenzotriazole (3.15 g 9.97 mmol), 4-acetamidobenzenethiol (2.50 g 14.96 mmol), potassium carbonate (3.03 g, 21.94 mmol) and potassium iodide (0.12 g 0.7 mmol) were reacted in 30 g of DMF at 135° C. for 12 hours. After the reaction was completed, the pH was adjusted, and then filtering and washing with water were performed, followed by performing recrystallization thereof several times to obtain Compound 21 as a light yellow solid. Physical property values thereof are shown below:

FT-IR (Kr): FT-IR (KBr): 2963 cm$^{-1}$: O—H stretching vibration 1653 cm$^{-1}$: C=O stretching vibration 1445, 1396 cm$^{-1}$: triazole ring stretching vibration $^1$H-NMR (CDCl$_3$ 400 MHz): δ 1.48 (s, 9H, -Ph-OH—CH$_3$—C(CH$_3$)$_3$), 2.21 (s, 3H, CH$_3$—C=O—NH—), 2.37 (s, 3H, -Ph-OH—CH$_3$—C(CH$_3$)$_3$), 7.17(s, 1H), 7.31 (d, 1H), 7.48 (d, 2H), 7.56 (d, 3H), 7.79 (d, 1H), 8.02 (s, 1H), (insg.9arom. CH), 11.54 (s, 1H, -Ph-OH—CH$_3$—C(CH$_3$)$_3$)

$^{13}$C-NMR (CDCl$_3$ 400 MHz): δ 20.9 (-Ph-OH—CH$_3$—C(CH$_3$)$_3$), 24.7 (-Ph-OH—CH$_3$—C(CH$_3$)$_3$), 29.5 (-Ph-OH—CH$_3$—C(CH$_3$)$_3$), 35.4(CH$_3$—C(=O)—NH—), 115.6, 117.9, 119.3, 120.7, 127.9, 128.8, 134.5 (CH$_{arom}$), 125.4, 141.5, 143.2 (C$_{arom}$), 128.3 (C$_{arom}$—CH$_3$), 129.1 (C$_{arom}$—S), 138.4(C$_{arom}$—S), 138.2 (C$_{arom}$—NH), 139.2 (C$_{arom}$—C(CH$_3$)$_3$), 146.7(C$_{arom}$—OH), 168.3 (CH$_3$—C(=O)—NH—)

<Compound 22>

[Chemical Formula 33]

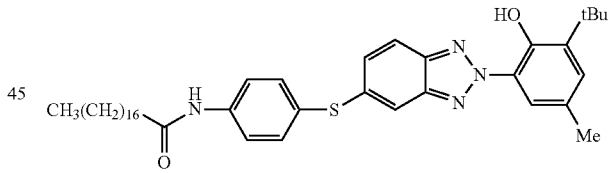

To stearic acid (0.70 g 2.47 mmol), 1-hydroxybenzotriazole monohydrate (0.41 g, 2.71 mmol) and N,N'-diisopropylcarbodiimide (0.35 g 2.76 mmol), 14 g of MEK was added, and the reaction was allowed to proceed for 1 hour at 65-75° C. under a nitrogen atmosphere, and then Intermediate 6 (1.00 g 2.47 mmol) was added and the reaction was allowed to proceed for 4 hours. After the reaction was completed, the reaction mixture was cooled to room temperature, and the precipitated crystals were filtered. The resulting filtrate was washed with MeOH and recrystallized to obtain Compound 22 as a light yellow solid. Physical property values thereof are shown below:

FT-IR (Kr): FT-IR (KBr): 2958 cm$^{-1}$: O—H stretching vibration 1655 cm$^{-1}$: C=O stretching vibration 1464, 1396 cm$^{-1}$: triazole ring stretching vibration $^1$H-NMR (CDCl$_3$ 400 MHz): δ 0.88 (t, 3H, CH$_3$(CH$_2$)$_{16}$—C(=O)NH—), 1.25 (m, 26H, CH$_3$(CH$_2$)$_{13}$CH$_2$CH$_2$—C(=O)NH—), 1.48 (s, 9H, -Ph-OH—

CH$_3$—C(CH$_3$)$_3$), 1.74 (quin, 2H, CH$_3$(CH$_2$)$_{13}$CH$_2$CH$_2$—C(=O)NH—), 2.37 (m, 5H, -Ph-OH—CH$_3$—C(CH$_3$)$_3$, CH$_3$(CH$_2$)$_{13}$CH$_2$CH$_2$—C(=O)NH—), 7.16 (m, 1H, CH$_3$(CH$_2$)$_{16}$—C(=O)NH—), 7.17 (s, 1H), 7.33 (d, 1H) 7.48 (d, 2H), 7.58 (m, 3H), 7.79 (d, 1H), 8.02 (s, 1), (insg.9arom. CH), 11.55 (s, 1H, -Ph-OH—CH$_3$—C(CH$_3$)$_3$)
$^{13}$C-NMR (CDCl$_3$ 400 MHz): δ14.1 (CH$_3$(CH$_2$)$_{16}$—C(=O)NH—), 20.9 (-Ph-OH—CH$_3$—C(CH$_3$)$_3$), 22.7 (CH$_3$CH$_2$(CH$_2$)$_{15}$—C(=O)NH—), 25.6 (-Ph-OH—CH$_3$—C(CH$_3$)$_3$), 29.3~29.7 (CH$_3$ CH$_2$ (CH$_2$)$_{12}$CH$_2$CH$_2$—C(=O)NH—), 29.7 (-Ph-OH—CH$_3$—C(CH$_3$)$_3$), 31.9 (CH$_3$(CH$_2$)$_{13}$CH$_2$CH$_2$—C(=O)NH—), 35.4 (CH$_3$(CH$_2$)$_{14}$CH$_2$CH$_2$—C(=O)NH—), 37.9 (CH$_3$(CH$_2$)$_{15}$CH$_2$—C(=O)NH—), 115.5, 117.9, 119.3, 120.7, 127.6, 128.8, 134.6 (CH$_{arom}$), 125.4, 141.5, 143.2(C$_{arom}$), 128.3 (C$_{arom}$—CH$_3$), 129.0 (C$_{arom}$—S), 138.6(C$_{arom}$—S), 139.1(C$_{arom}$—C(CH$_3$)$_3$), 138.1(C$_{arom}$—NH), 146.7 (C$_{arom}$—OH), 171.6 (CH$_3$(CH$_2$)$_{17}$—C(=O)NH—)

<Compound 23>

[Chemical Formula 34]

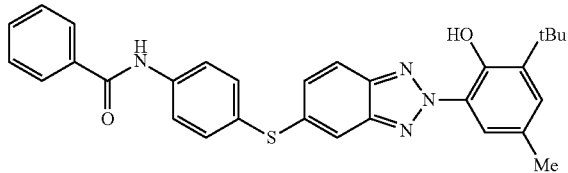 [SMILES: Cc1cc(-n2nc3ccc(Sc4ccc(OC(=O)c5ccccc5)cc4)cc3n2)c(O)c(C(C)(C)C)c1]

Intermediate 6 (0.50 g 1.24 mmol) and benzoyl chloride (0.26 g 1.86 mmol) were stirred in 10 mL of methylene chloride for 18 hours at room temperature. After the reaction was completed, methanol was added to the reaction solution, and the precipitate was filtered to obtain a yellow crude product. The crude product thus obtained was recrystallized to obtain Compound 23 as a light yellow solid. Physical property values thereof are shown below: FT-IR (KBr): FT-IR (KBr): 2955 m$^{-1}$:O—H stretching vibration 1654 cm$^{-1}$:C=O stretching vibration 1449, 1396 cm$^{-l}$: triazole ring stretching vibration $^1$H-NMR (CDCl$_3$400 MHz): δ1.48 (s, 9H, -Ph-OH—CH$_3$—C(CH$_3$)$_3$), 2.37 (s, 3H, -Ph-OH—CH$_3$—C(CH$_3$)$_3$), 7.90 (m, 1H, Ph-C(=O)NH—), 7.16 (s, 1H), 7.33 (d, 1H), 7.50-7.57 (m, 5H), 7.63 (s, 1H), 7.73 (d, 2H), 7.82 (d, 1H), 7.90 (m, 2H), 8.04 (s, 1H), (insg.14arom. CH), 11.55 (s, 1H, -Ph-OH—CH$_3$—C(CH$_3$)$_3$)

$^{13}$C-NMR (CDCl$_3$ 400 MHz): δ20.9 (-Ph-OH—CH$_3$—C(CH$_3$)$_3$), 29.5 (-Ph-OH—CH$_3$—C(CH$_3$)$_3$), 35.4 (-Ph-OH—CH$_3$—C(CH$_3$)$_3$), 115.8, 118.0, 119.3, 121.1, 127.0, 128.4, 128.9, 132.1, 134.5 (CH$_{arom}$), 125.4, 141.5, 143.2(C$_{arom}$), 128.3 (C$_{arom}$—CH$_3$), 128.8(C$_{arom}$—C(=O)NH—), 129.2(C$_{arom}$—S), 138.1(C$_{arom}$—S), 138.5(Ph-C(=O)NH—C$_{arom}$), 139.2(C$_{arom}$—C(CH$_3$)$_3$), 146.8(C$_{arom}$—OH), 165.7 (Ph-C(=O)NH—)

<Compound 24>

[Chemical Formula 35]

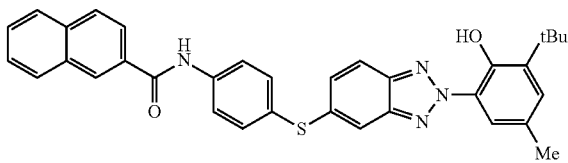 [SMILES: Cc1cc(-n2nc3ccc(Sc4ccc(NC(=O)c5ccc6ccccc6c5)cc4)cc3n2)c(O)c(C(C)(C)C)c1]

Intermediate 6 (1.00 g 2.47 mmol) and 2-naphthoyl chloride (0.71 g 3.71 mmol) were stirred in 2 mL of methylene chloride for 3 hours at room temperature. After the reaction was completed, the precipitate was filtered and the crude product was recrystallize to obtain Compound 24 as a light yellow solid. Physical property values thereof are shown below:

FT-IR (KBr): FT-IR (KBr): 2956 m$^{-1}$:O—H stretching vibration 1659 cm$^{-1}$:C=O stretching vibration 1445, 1397 cm$^{-1}$: triazole ring stretching vibration $^1$H-NMR (CDCl$_3$400 MHz): δ1.48 (s, 9H, -Ph-OH—CH$_3$—C(CH$_3$)$_3$), 2.37 (s, 3H, -Ph-OH—CH$_3$—C(CH$_3$)$_3$), 7.16 (s, 1H), 7.35 (d, 1H), 7.55-7.63 (m, 5H), 7.65 (s, 1H), 7.77 (d, 2H), 7.84 (d, 1H), 7.91-7.99 (m, 4H), 8.04 (m, 2H), (insg.14arom. CH), 8.41(s, 1, Np—C(=O)NH—), 11.55 (s, 1H, -Ph-OH—CH$_3$—C(CH$_3$)$_3$)

$^{13}$C-NMR (CDCl$_3$ 400 MHz): δ20.9 (-Ph-OH—CH$_3$—C(CH$_3$)$_3$), 29.5 (-Ph-OH—CH$_3$—C(CH$_3$)$_3$), 35.4 (-Ph-OH—CH$_3$—C(CH$_3$)$_3$), 115.8, 118.0, 119.3, 121.1, 127.1, 127.7, 127.9, 128.1, 128.9, 129.2, 132.1, 134.5 (CH$_{arom}$), 135.0, 131.9 (Np—C$_{arom}$), 123.4, 141.6, 143.2(C$_{arom}$), 128.3 (C$_{arom}$—CH$_3$) 12.8 (C$_{arom}$—C(=O)NH—), 129.2 (C$_{arom}$—S), 138.1 (C$_{arom}$—S), 138.6(Np—C(=O)NH—C$_{arom}$), 139.2 (C$_{arom}$—C(CH$_3$)$_3$), 146.7(C$_{arom}$—OH), 165.7(Np—C(=O)NH—)

<Compound 25>

[Chemical Formula 36]

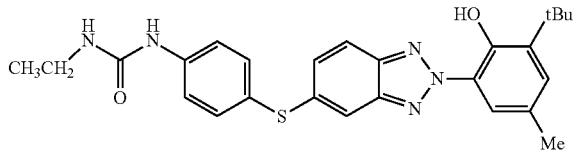

Intermediate 6(1.00 g 2.47 mmol) and ethylisocyanate (1.18 g 16.54 mmol) were heated and stirred in 20 mL of DMF for 16 hours at 100° C. After the reaction was completed, toluene and water were added, and subjected to washing with water, and the organic layer was distilled off under reduced pressure to obtain a yellow solid. The crude product thus obtained was subjected to column purification and recrystallized to synthesize alight yellow solid Compound 25. Physical property values thereof are shown below:

FT-IR (KBr): FT-IR (KBr): 2968 cm$^{-1}$: O—H stretching vibration 1639 cm$^{-1}$: C=O stretching vibration 1436, 1392 cm$^{-1}$: triazole ring stretching vibration $^1$H-NMR (CDCl$_3$ 400 MHz): δ1.13 (t, 3H, CH$_3$CH$_2$—NH—C(=O)NH—), 1.41 (s, 9H, -Ph-OH—CH$_3$—C(CH$_3$)$_3$), 2.30 (m, 3H, -Ph-OH—CH$_3$—C(CH$_3$)$_3$), 3.26(quin, 2H, CH$_3$CH$_2$—NH—C(=O)NH—), 4.63 (m, 1H, CH$_3$CH$_2$—NHC(=O)NH—), 6.31 (m, 1H, CH$_3$CH$_2$—NHC(=O)NH—)

7.08 (s, 1H), 7.23 (d, 1H), 7.30 (d, 2H), 7.38 (m, 2H), 7.49 (d, 1H), 7.71 (s, 1H), 7.95 (s, 1H), (insg.9arom. CH), 11.47 (s, 1H, -Ph-OH—CH$_3$—C(CH$_3$)$_3$)

$^{13}$C-NMR (CDCl$_3$ 400 MHz): δ14.1 (CH$_3$CH$_2$—HNC(=O)NH—), 20.9 (-Ph-OH—CH$_3$—C(CH$_3$)$_3$), 29.5 (-Ph-OH—CH$_3$—C(CH$_3$)$_3$), 35.4 (-Ph-OH—CH$_3$—C(CH$_3$)$_3$), 35.4 (CH$_3$ CH$_2$—HNC(=O)NH—), 115.3, 117.9, 119.3, 121.1, 126.2, 128.8, 134.9 (CH$_{arom}$), 125.3, 141.4, 143.2 (C$_{arom}$), 128.3 (C$_{arom}$—CH$_3$), 128.9 (C$_{arom}$—S), 138.7 (C$_{arom}$—S), 139.1

($\underline{C}_{arom}$—C(CH$_3$)), 139.1 ($\underline{C}_{arom}$—NH), 146.7($\underline{C}_{arom}$—OH), 154.8 (CH$_3$CH$_2$—HN$\underline{C}$(═O)NH—)

<Compound 26>

[Chemical Formula 37]

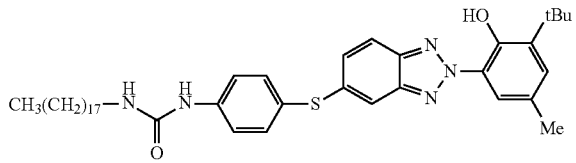

Intermediate 7 (1.00 g 2.38 mmol), 2-(2-hydroxy-3-tert-butyl-5-methylphenyl)-5-chlorobenzotriazole (0.60 g 1.90 mmol), potassium carbonate (0.58 g 4.18 mmol), and potassium iodide (0.002 g 0.11 mmol) were heated and stirred in 20 mL of DMF for 8 hours at 135-140° C. After the reaction was completed, the reaction solution was pH-adjusted, filtered, and washed with MeOH, and then subjected to column purification and recrystallized to obtain a yellow-solid Compound 26. Physical property values thereof are shown below:

FT-IR (KBr): FT-IR (KBr): 2916 cm$^{-1}$: O—H stretching vibration 1636 cm$^{-1}$: C═O stretching vibration 1465, 1396 cm$^{-1}$: triazole ring stretching vibration $^1$H-NMR (CDCl$_3$400 MHz): δ 0.88 (t, 3H, C$\underline{H}_3$(CH$_2$)$_{17}$—NHC(═O)NH—), 1.25 (m, 28H, CH$_3$(C$\underline{H}_2$)$_{14}$CH$_2$CH$_2$CH$_2$—NHC(═O)NH—), 1.48 (m, 11H, -Ph-OH—CH$_3$—C(C$\underline{H}_3$)$_3$, CH$_3$(CH$_2$)$_{14}$C$\underline{H}_2$CH$_2$CH$_2$—NHC(═O)NH—), 1.56 (m, 2H, CH$_3$(CH$_2$)$_{14}$CH$_2$C$\underline{H}_2$CH$_2$—NHC(═O)NH—), 2.37 (s, 3H, -Ph-OH—C$\underline{H}_3$—C(CH$_3$)$_3$), 3.27(quin, 2H, CH$_3$(CH$_2$)$_{14}$CH$_2$CH$_2$C$\underline{H}_2$—NHC(═O)NH—), 4.68 (m, 1H, CH$_3$(CH$_2$)$_{14}$CH$_2$CH$_2$CH$_2$—NHC(═O)N$\underline{H}$—), 6.35 (m, 1H, CH$_3$(CH$_2$)$_{14}$CH$_2$CH$_2$CH—N$\underline{H}$C(═O)NH—), 7.15 (s, 1H), 7.32 (d, 1H), 7.38 (d, 2H), 7.45 (d, 2H), 7.56 (s, 1H), 7.78 (d, 1H), 8.02 (s, 1H), (insg.9arom. C$\underline{H}$), 11.55 (s, 1, -Ph-O$\underline{H}$—CH$_3$—C(CH$_3$)$_3$) $^{13}$C-NMR (CDCl$_3$ 400 MHz): 14.1 ($\underline{C}$H$_3$(CH$_2$)$_{17}$—NHC(═O)NH—), 20.9 (-Ph-OH—$\underline{C}$H$_3$—C(CH$_3$)$_3$), 22.7 (CH$_3$$\underline{C}$H$_2$(CH$_2$)$_{16}$—NHC(═O)NH—), 26.9 (-Ph-OH—CH$_3$—$\underline{C}$(CH$_3$)$_3$), 29.4~29.7 (CH$_3$CH$_2$($\underline{C}$H$_2$)$_{13}$CH$_2$CH$_2$CH$_2$—NHC(═O)NH—), 29.7 (-Ph-OH—CH$_3$—C($\underline{C}$H$_3$)$_3$), 31.9 (CH$_3$(CH$_2$)$_{14}$$\underline{C}$H$_2$CH$_2$CH$_2$—NHC(═O)NH—), 35.4 (CH$_3$(CH$_2$)$_{15}$$\underline{C}$H$_2$CH$_2$—NHC(═O)NH—), 40.6 (CH$_3$(CH$_2$)$_{16}$$\underline{C}$H$_2$—NHC(═O)NH—), 115.1, 117.8, 119.3, 120.9, 126.2, 128.7, 134.9($\underline{C}$H$_{arom}$), 125.3, 141.4, 143.2 ($\underline{C}_{arom}$), 128.2 ($C_{arom}$—$\underline{C}$H$_3$), 128.9 ($\underline{C}_{arom}$—S), 138.7 ($\underline{C}_{arom}$—S), 139.1 ($\underline{C}_{arom}$—C(CH$_3$)$_3$), 139.7 ($\underline{C}_{arom}$, NH), 146.7($\underline{C}_{arom}$—OH), 155.4 (CH$_3$(CH$_2$)$_{17}$—NH$\underline{C}$(═O)NH—)

<Compound 27>

[Chemical Formula 38]

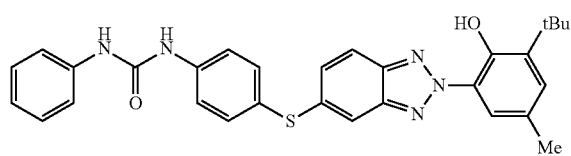 [SMILES: Cc1cc(-n2nc3ccc(Sc4ccc(NC(=O)Nc5ccccc5)cc4)cc3n2)c(O)c(C(C)(C)C)c1]

Intermediate 6 (1.00 g 2.47 mmol) and phenyl isocyanate (0.31 g 2.60 mmol) were heated and stirred in DMF20 mL for 8 hours at 100° C. After the reaction was completed, water was added and the precipitated crystals were filtered to obtain a yellow solid. The crude product thus obtained was subjected to column purification and recrystallized to synthesize a light yellow solid Compound 27. Physical property values thereof are shown below:

FT-IR (KBr): FT-IR (KBr): 2961 cm$^{-1}$: O—H stretching vibration 1659 cm$^{-1}$: C═O stretching vibration 1444, 1396 cm$^{-1}$: triazole ring stretching vibration $^1$H-NMR (CDCl$_3$400 MHz): δ1.48 (s, 9H, -Ph-OH—CH$_3$—C(C$\underline{H}_3$)$_3$), 2.36 (s, 3H, -Ph-OH—C$\underline{H}_3$—C(CH$_3$)$_3$), 6.60 (m, 1, -Ph-NHC(═O)N$\underline{H}$—), 6.73 (m, 1H, -Ph-N$\underline{H}$C(═O)NH—) 7.16 (m, 2H), 7.32 (d, 1), 7.38 (m, 4), 7.44 (m, 4H), 7.57 (s, 1), 7.80 (d, 1H), 8.02 (s, 1H), (insg.14arom. C$\underline{H}$), 11.55 (s, 1, -Ph-O$\underline{H}$—CH$_3$—C(CH$_3$)$_3$)

$^{13}$C-NMR (CDCl$_3$ 400 MHz): δ20.9 (-Ph-OH—$\underline{C}$H$_3$—C(CH$_3$)$_3$), 29.5 (-Ph-OH—CH$_3$—C($\underline{C}$H$_3$)$_3$), 35.4 (-Ph-OH—CH$_3$—$\underline{C}$(CH$_3$)$_3$), 115.5, 117.9, 119.3, 121.1, 121.9, 128.8, 129.0, 129.7, 129.6, 134.7($\underline{C}$H$_{arom}$), 125.0, 141.5, 143.2($\underline{C}_{arom}$), 128.3 ($C_{arom}$—$\underline{C}$H$_3$), 125.4(Ph-S—$\underline{C}_{arom}$), 127.2($\underline{C}_{arom}$—S-Ph), 139.1($\underline{C}_{arom}$—C(CH$_3$)$_3$), 137.5(Ph-HN—C(═O)—NH—$\underline{C}_{arom}$), 138.4($\underline{C}_{arom}$—HN—C(═O)—NH-Ph), 146.7($\underline{C}_{arom}$—OH), 152.7 (—HN—$\underline{C}$(═O)—NH—)

<Compound 28>

[Chemical Formula 39]

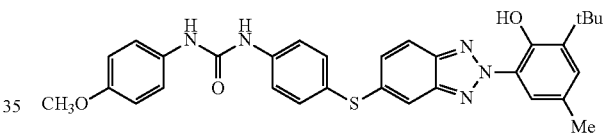

Intermediate 6 (0.10 g 0.25 mmol) and 4-methoxyphenyl isocyanate (0.0369 g 0.25 mmol) were heated and stirred in DMF5 mL for 18 hours at 100° C. After the reaction was completed, water was added and the precipitated crystals were filtered to obtain a yellow solid. The crude product thus obtained was subjected to column purification and recrystallized to synthesize a light yellow solid Compound 28. Physical property values thereof we shown below:

FT-IR (KBr): FT-IR (KBr): 2964 cm$^{-1}$: O—H stretching vibration 1673 cm$^{-1}$: C═O stretching vibration 1409, 1358 cm$^{-1}$: triazole ring stretching vibration $^1$H-NMR (CDCl$_3$400 MHz): 1.48 (s, 9H, -Ph-OH—C$\underline{H}_3$—C(CH$_3$)$_3$), 2.36 (m, 3, -Ph-OH—C$\underline{H}_3$—C(CH$_3$)$_3$), 3.80 (s, 3H, C$\underline{H}_3$O-Ph-), 6.55 (m, 1H, -Ph-NHC(═O)N$\underline{H}$—), 6.77 (m, 1H, -Ph-N$\underline{H}$C(═O)NH—), 6.89 (d, 2H), 7.15 (s, 1H), 7.28 (m, 3H), 7.39 (m, 4H), 7.76 (d, 1H), 8.01(s, 1H), (insg.13arom. C$\underline{H}$), 11.54 (s, 1H, -Ph-O$\underline{H}$—CH$_3$—C(CH$_3$)$_3$)

$^{13}$C-NMR (CDCl$_3$ 400 MHz): δ20.9 (-Ph-OH—$\underline{C}$H$_3$—C(CH$_3$)$_3$), 29.5 (-Ph-OH—CH$_3$—C($\underline{C}$H$_3$)$_3$), 35.4 (-Ph-OH—CH$_3$—$\underline{C}$(CH$_3$)$_3$), 55.6 ($\underline{C}$H$_3$—O-Ph-)

115.0, 117.9, 119.1, 120.8, 120.9, 128.8, 129.0, 129.5, 129.6, 134.8($\underline{C}$H$_{arom}$), 125.0, 141.5, 143.2($\underline{C}_{arom}$), 128.3 ($C_{arom}$—$\underline{C}$H$_3$), 125.4(Ph-S—$\underline{C}_{arom}$), 127.2($\underline{C}_{arom}$—S-Ph), 139.1($\underline{C}_{arom}$—C(CH$_3$)$_3$), 137.5(Ph-HN—C(═O)—NH—$\underline{C}_{arom}$), 13.4($\underline{C}_{arom}$—HN—C(═O)—NH-Ph), 146.7($\underline{C}_{arom}$—OH), 152.7 (—HN—$\underline{C}$(═O)—NH—)

Compound 10, Compound 29 and Compound 30 were synthesized as described in WO 2016/021664.

As for Compound 11 and Compound 12, reagents manufactured by Tokyo Chemical Industry Co., Ltd. were used.

2. Evaluation of UV Absorption Performance (1)

Compounds 1 to 12 were diluted with 100 µM of chloroform, placed in a 10-mm quartz cell, and the absorbance spectra were measured using an ultraviolet-visible spectrophotometer (V-550, manufactured by JASCO Corporation) (FIGS. 1 to 12).

As a result, it was shown that the Compounds 1 to 9 of the present invention have an absorption band in the wavelength region of ultraviolet rays and function as an ultraviolet absorber when added to a film or a resin.

It was confirmed that the benzotriazole-based Compounds 1 to 9 of the present invention in which a thioether group having a reactive functional group represented by the above formula (i-2) was introduced into a benzotriazole group had a peak top shifted to a long wavelength region compared with the conventional reactive ultraviolet absorber (Compound 11) and the long-wavelength-absorbing-type ultraviolet absorber (Compound 12), and were superior in ultraviolet absorption in the vicinity of 360 to 400 nm in the longer wavelength region. Compounds 5 and 6 in which an aromatic group was introduced into X of the formula (i-2) generally had a large absorption peak in a region of 250 to 320 nm (absorbance became large), enabling the absorbing of ultraviolet rays in a wide range of from a low wavelength to a long wavelength.

The absorption peak (maximum absorption wavelength: $\lambda_{max}$) and absorbance in the wavelength range of 350 to 390 nm were read from the absorption spectra of Compounds 1 to 12, and the molar extinction coefficient of the peak (maximum molar extinction coefficient: $\varepsilon_{max}$) was obtained by the following equation (able 1).

Molar extinction coefficient:$\varepsilon_{max}$(L/(mol·cm))=$A$: Absorbance/[$c$:Mol concentration(mol/L)×l:Cell optical length(cm)]   [Equation 1]

As a result, it was shown that Compounds 1 to 9 of the present invention having a thioether group and an acryloyloxy group introduced thereinto had a molar extinction coefficient as high as 21,000 or more that is higher than Compounds 10, 11, and 12, thus demonstrating efficient absorption of ultraviolet rays by addition of a small amount thereof.

In addition, from the absorption spectra of Compounds 1 to 12, assuming that an intersection of a long-wavelength side absorption spectrum in the absorption peak at 350 to 390 nm and a baseline (a line where the slope of the absorption spectrum at 380 to 500 nm is zero) is set as a peak end (for example: FIG. 1), the absolute value of the slope of the absorption peak on the long-wavelength side in the wavelength region at 350 to 390 nm was obtained by the following equation:

|Slope of absorption peak on long wavelength side in wavelength region of 350 to 390 nm|=|(Absorbance at peak end−Absorbance at absorption peak in wavelength region of 350 to 390 nm)/ (Absorption wavelength at peak end−Wave length at absorption peak in wavelength region of 350 to 390 nm)|   [Equation 2]

As a result, the absolute values of slopes of Compounds 1 to 9 were all 0.040 or more, which were larger than those of Compounds 10, 11, and 12 (absolute values of slopes: 0.022 to 0.038) so that the peaks were sharp, and that Compounds 1 to 9 of the present invention having the sulfur-containing group (thioether group) and the acryloyloxy group introduced therein had a reduced cut at 400 to 500 nm (visible range), and thus it was suggested that the yellow color suppressing effect on a film, a resin member, particularly a transparent resin member is excellent. In particular, Compounds 1 to 6 of 0.042 or more are excellent in such effects.

TABLE 1

| Compound No. | | Structural formula | Wave length at absorption peak in wavelength region of 350 to 390 nm (maximum absorption wavelength: $\lambda_{max}$) [nm] | Molar extinction coefficient at peak in the left column (maximum molar extinction coefficient: $\varepsilon_{max}$) [L/(mol · cm)] |
|---|---|---|---|---|
| Working example 1 | 1 | [structural formula] | 368 | 22600 |
| Working example 2 | 2 | [structural formula] | 365 | 21400 |

TABLE 1-continued

| Compound No. | | Structural formula | Wave length at absorption peak in wavelength region of 350 to 390 nm (maximum absorption wavelength: $\lambda_{max}$) [nm] | Molar extinction coefficient at peak in the left column (maximum molar extinction coefficient: $\varepsilon_{max}$) [L/(mol·cm)] |
|---|---|---|---|---|
| Working example 3 | 3 | (structure: methacrylate-O(CH$_2$)$_3$S-benzotriazole-phenol with tBu, HO, Me) | 367 | 21600 |
| Working example 4 | 4 | (structure: methacrylate-O(CH$_2$)$_6$S-benzotriazole-phenol with tBu, HO, Me) | 368 | 22400 |
| Working example 5 | 5 | (structure: methacrylate-O-phenyl-S-benzotriazole-phenol with tBu, HO, Me) | 367 | 21800 |
| Working example 6 | 6 | (structure: methacrylate-O-O(CH$_2$)$_6$S-O-phenyl-S-benzotriazole-phenol with tBu, HO, Me) | 369 | 21600 |
| Working example 7 | 7 | (structure: crotonate-O(CH$_2$)$_6$S-benzotriazole-phenol with tBu, HO, Me) | 368 | 21900 |
| Working example 8 | 8 | (structure: CH$_3$(CH$_2$)$_2$-CH=CH-C(O)-O(CH$_2$)$_6$S-benzotriazole-phenol with tBu, HO, Me) | 368 | 21400 |
| Working example 9 | 9 | (structure: CH$_3$(CH$_2$)$_{12}$-CH=CH-C(O)-O(CH$_2$)$_6$S-benzotriazole-phenol with tBu, HO, Me) | 368 | 21100 |

TABLE 1-continued

| Compound No. | Structural formula | Wave length at absorption peak in wavelength region of 350 to 390 nm (maximum absorption wavelength: $\lambda_{max}$) [nm] | Molar extinction coefficient at peak in the left column (maximum molar extinction coefficient: $\varepsilon_{max}$) [L/(mol · cm)] |
|---|---|---|---|
| Comparative example 1 | 10 | 375 | 17600 |
| Comparative example 2 | 11 | 341 | 18300 |
| Comparative example 3 | 12 | 353 | 15300 |

TABLE 2

| Compound No. | Structural formula | Absorbance at absorption peak in wavelength region of 350 to 390 nm | Absorbance at peak end | Absorption wavelength at peak end [nm] | Absolute value of slope of absorption peak on long wavelength side in wavelength region of 350 to 390 nm |
|---|---|---|---|---|---|
| Working example 10 | 1 | 2.26 | 0.00766 | 422 | 0.042 |
| Working example 11 | 2 | 2.25 | 0.00727 | 421 | 0.042 |

TABLE 2-continued

| Compound No. | Structural formula | Absorbance at absorption peak in wavelength region of 350 to 390 nm | Absorbance at peak end | Absorption wavelength at peak end [nm] | Absolute value of slope of absorption peak on long wavelength side in wavelength region of 350 to 390 nm |
|---|---|---|---|---|---|
| Working example 12 | 3 | 2.18 | 0.00692 | 419 | 0.042 |
| Working example 13 | 4 | 2.24 | 0.00762 | 420 | 0.043 |
| Working example 14 | 5 | 2.29 | 0.01022 | 422 | 0.042 |
| Working example 15 | 6 | 2.27 | 0.01184 | 424 | 0.042 |
| Working example 16 | 7 | 2.19 | 0.00728 | 422 | 0.041 |
| Working example 17 | 8 | 2.11 | 0.00700 | 421 | 0.040 |

TABLE 2-continued

| Compound No. | | Structural formula | Absorbance at absorption peak in wavelength region of 350 to 390 nm | Absorbance at peak end | Absorption wavelength at peak end [nm] | Absolute value of slope of absorption peak on long wavelength side in wavelength region of 350 to 390 nm |
|---|---|---|---|---|---|---|
| Working example 18 | 9 | (structure: CH₃(CH₂)₁₂—CH=CH—C(=O)—O(CH₂)₆S—benzotriazole—phenyl(HO, tBu, Me)) | 2.14 | 0.00702 | 422 | 0.040 |
| Comparative example 4 | 10 | (structure: allyl-S—benzotriazole—phenyl(HO, tBu, Me)) | 1.76 | 0.00722 | 430 | 0.032 |
| Comparative example 5 | 11 | (structure: benzotriazole—phenyl(HO)—CH₂CH₂—O—C(=O)—C(CH₃)=CH₂) | 1.83 | 0.00690 | 388 | 0.038 |
| Comparative example 6 | 12 | (structure: Cl-benzotriazole—phenyl(HO, tBu, Me)) | 1.53 | 0.00617 | 423 | 0.022 |

3. Evaluation of reactivity (1)

Methyl methacrylate (4.99 mmol), Compounds 1 to 6,10, 11 (0.15 mmol), toluene (0.5 g) and MEK (0.5 g) were added, and subjected to nitrogen substitution for 1 hour, and then, 1,1'-azobis (cyclohexane-1-carbonitrile) (0.15 mmol) was added, followed by heating and stirring the same at 90 to 96° C. for 10 hours to carry out copolymerization. At that time, the peaks of the hydrogen atoms bonded to the double bond were measured at predetermined time intervals (1, 5.10 hours) by NMR, and thus the reaction rate was calculated (Table 3).

As a result, it was confirmed that as compared with Compound 10 having no methacrylic or acrylic group as the reactive functional group, Compounds 1 to 6 and 11 having the methacrylic or acrylic group had a reaction rate of about 70% or more after 10 hours, and their reactivity was high. Among them, when compared with Compound 11 having no sulfur-containing group (thioether group), Compounds 1 to 6 having a sulfur-containing group (thioether group) had a reaction rate of about 99% or more after 10 hours, and high reactivity, suggesting that polymerization was possible with a higher molecular weight, and thus it was confirmed that the reactivity was improved by the introduction of the functional group of the acryloyloxy group (methacrylic, acrylic group) and the sulfur-containing group (thioether group).

Further, it was confirmed that the reaction rate of Compound 1 having an acrylic group was high after 5 or 10 hours, and among Compounds 2 to 4 having an alkylene group as X and a methacrylic group, Compounds 3 and 4 having 3 or more carbon atoms of alkylene groups from the methacrylic group to the sulfur-containing group (thioether group) had higher reaction rates after 1, 5, and 10 hours than Compound 2 having 2 carbon atoms of alkylene group, and the reactivity was good.

TABLE 3

| Compound No. | Structural formula | Reaction rate [%] 1 h | 5 h | 10 h |
|---|---|---|---|---|
| Working example 19 / 1 | (benzotriazole with acrylate-O(CH₂)₆S- linker, HO, tBu, Me substituents) | 20.0 | 100.0 | 100.0 |
| Working example 20 / 2 | (benzotriazole with methacrylate-O(CH₂)₂S- linker) | 50.6 | 97.7 | 99.1 |
| Working example 21 / 3 | (benzotriazole with methacrylate-O(CH₂)₃S- linker) | 60.5 | 98.6 | 99.5 |
| Working example 22 / 4 | (benzotriazole with methacrylate-O(CH₂)₆S- linker) | 61.0 | 98.6 | 99.4 |
| Working example 23 / 5 | (benzotriazole with methacrylate-O-phenyl-S- linker) | 22.0 | 98.0 | 99.3 |
| Working example 24 / 6 | (benzotriazole with methacrylate-O-(CH₂)₆-O-phenyl-S- linker) | 78.7 | 98.3 | 99.5 |
| Comparative example 7 / 10 | (benzotriazole with allyl-S- linker) | — | — | 5.0 |

TABLE 3-continued

| Compound No. | Structural formula | Reaction rate [%] 1 h | 5 h | 10 h |
|---|---|---|---|---|
| Comparative example 8 | 11 (benzotriazole-phenol with HO and methacrylate ester via ethylene linker) | 22.3 | 47.3 | 69.5 |

4. Evaluation of Copolymer Films 1 mL of chloroform was added to the reaction solution of Compounds 1 to 6 that were polymerized in above (1), 10 μL of which was then put by drops on a slide glass, and then the solvent was removed to prepare a film. The transparency was evaluated according to the following criteria (able 4).

Evaluation Criteria:
○:Clear with no white turbidity
Δ: Some white turbidity, but clear
x: Poor clarity due to white turbidity As a result, it was confirmed that polymers having good transparency were obtained in Compounds 1 to 6.

Figure 13:
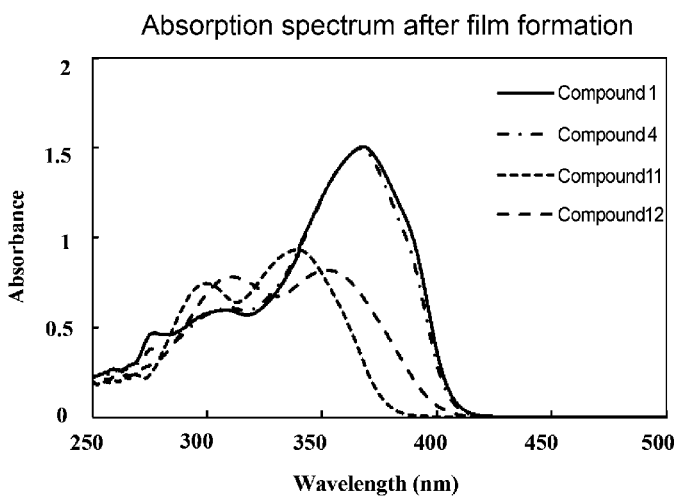
FIG. 13 shows ultraviolet-visible absorption spectra (UV charts) of copolymer films using Compound 1 and Compound 4 of the present invention, and Compound 11 and Compound 12 of the comparative examples.
Figure 14:
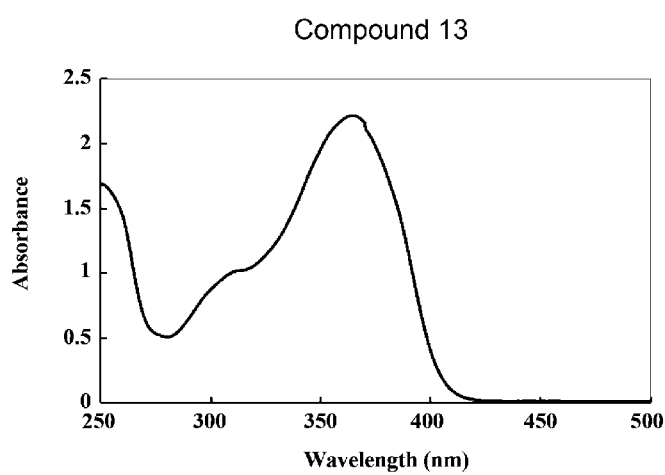
FIG. 14 is an ultraviolet-visible absorption spectrum (UV chart) of Compound 13 according to a working example of the present invention.
Figure 15:
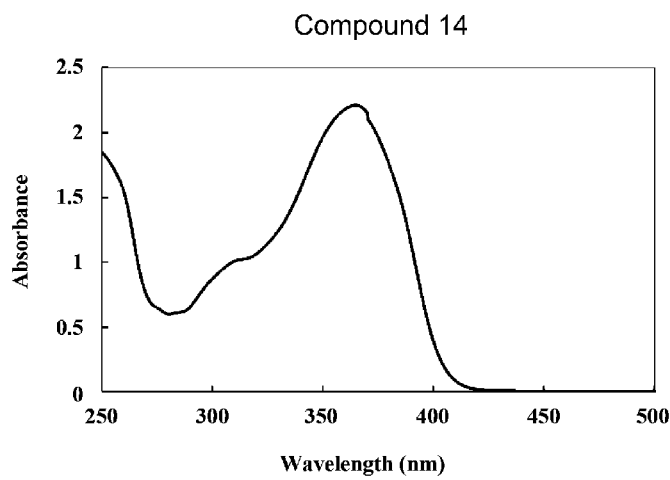
FIG. 15 is an ultraviolet-visible absorption spectrum (UV chart) of Compound 14 according to a working example of the present invention.
Figure 16:
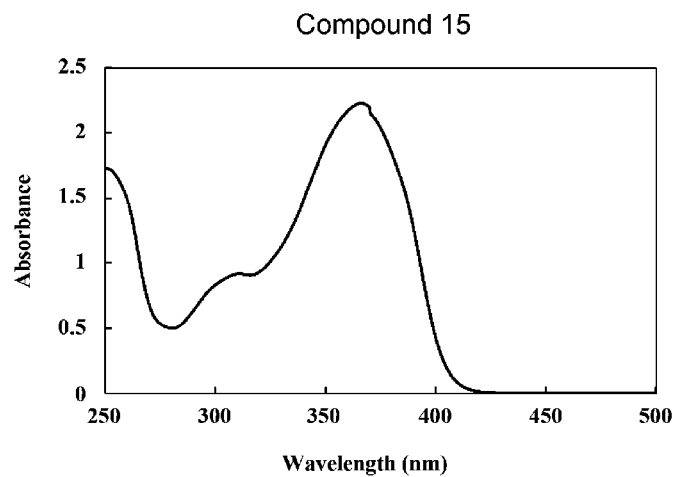
FIG. 16 is an ultraviolet-visible absorption spectrum (UV chart) of Compound 15 according to a working example of the present invention.
Figure 17:
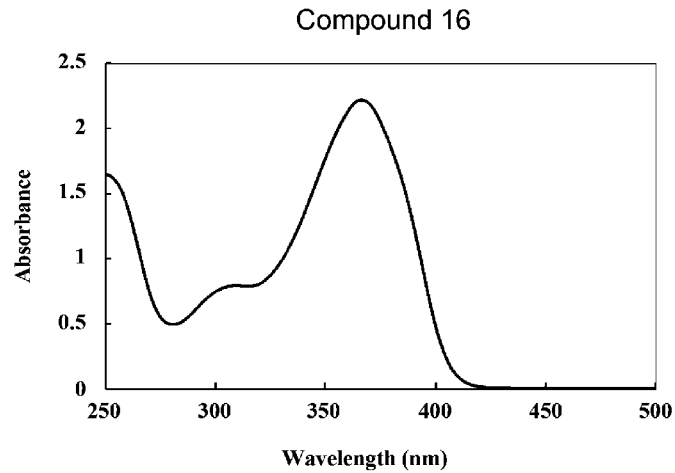
FIG. 17 is an ultraviolet-visible absorption spectrum (UV chart) of Compound 16 according to a working example of the present invention.
Figure 18:
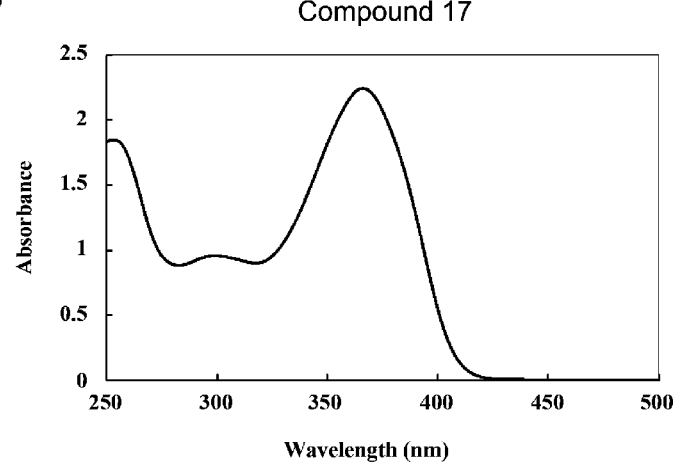
FIG. 18 is an ultraviolet-visible absorption spectrum (UV chart) of Compound 17 according to a working example of the present invention.
Figure 19:
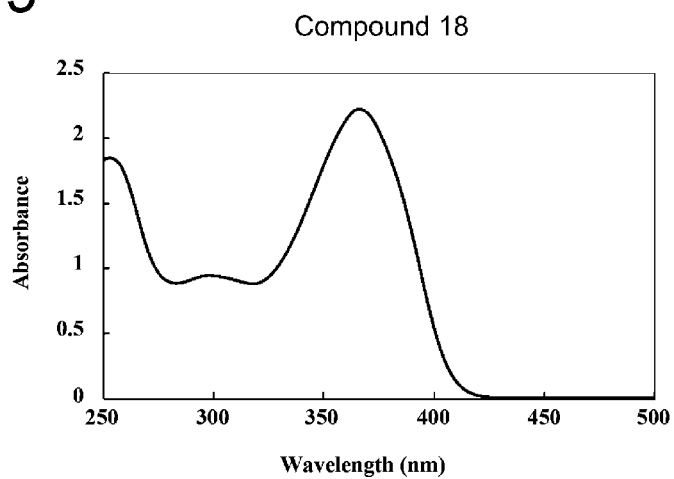
FIG. 19 is an ultraviolet-visible absorption spectrum (U chart) of Compound 18 according to a working example of the present invention.
Figure 20:
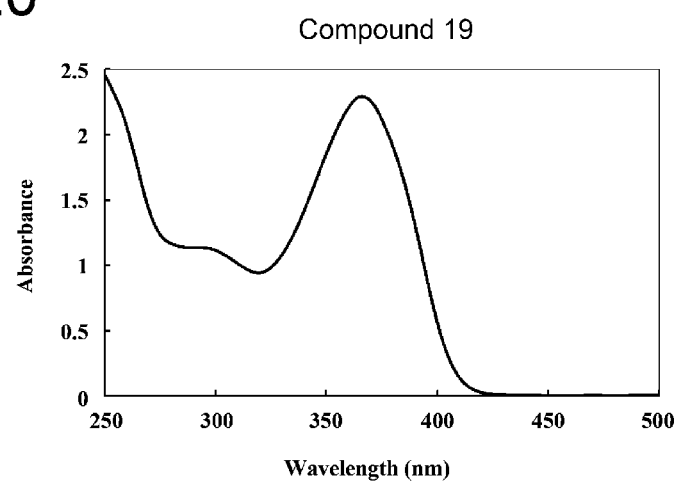
FIG. 20 is an ultraviolet-visible absorption spectrum (chart) of Compound 19 according to a working example of the present invention.
Figure 21:
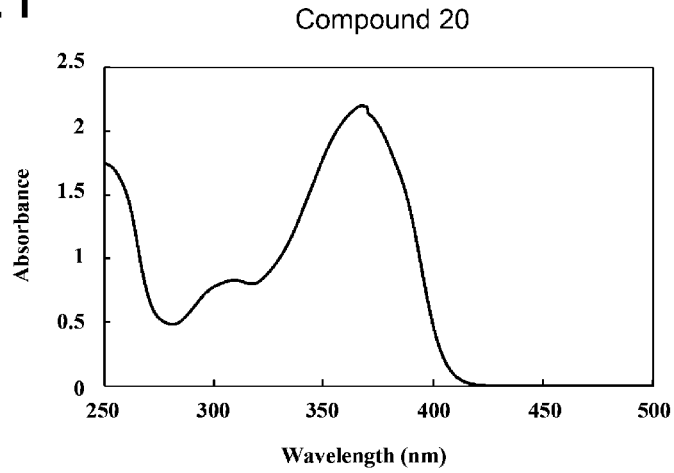
FIG. 21 is an ultraviolet-visible absorption spectrum (U chart) of Compound 20 according to a working example of the present invention.
Figure 22:
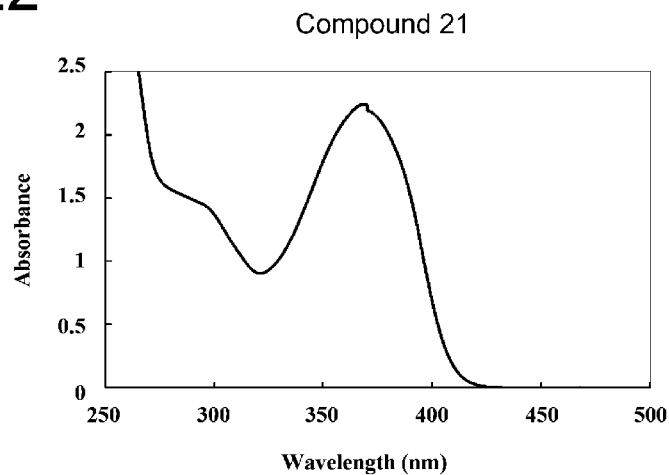
FIG. 22 is an ultraviolet-visible absorption spectrum (UV chart) of Compound 21 according to a working example of the present invention.
Figure 23:
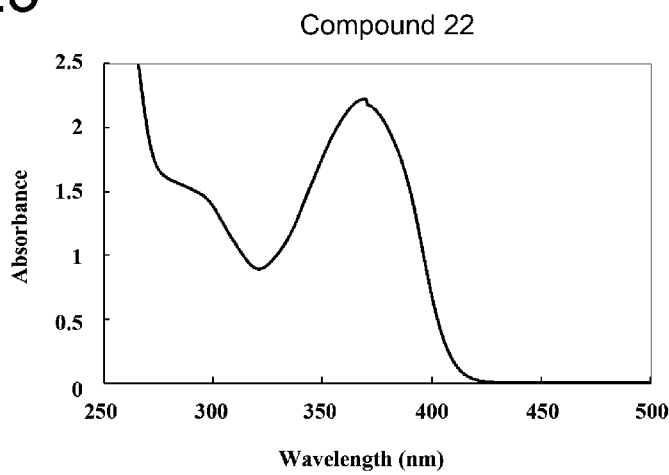
FIG. 23 is an ultraviolet-visible absorption spectrum (UV chart) of Compound 22 according to a working example of the present invention.
Figure 24:
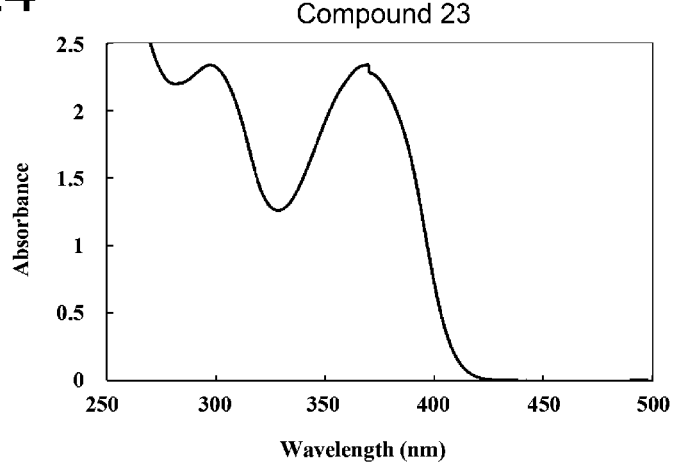
FIG. 24 is an ultraviolet-visible absorption spectrum (UV chart) of Compound 23 according to a working example of the present invention.
Figure 25:
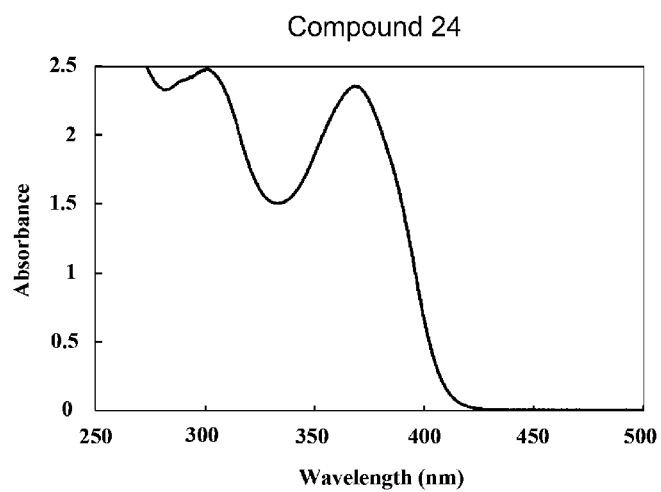
FIG. 25 is an ultraviolet-visible absorption spectrum (UV chart) of Compound 24 according to a working example of the present invention.
Figure 26:
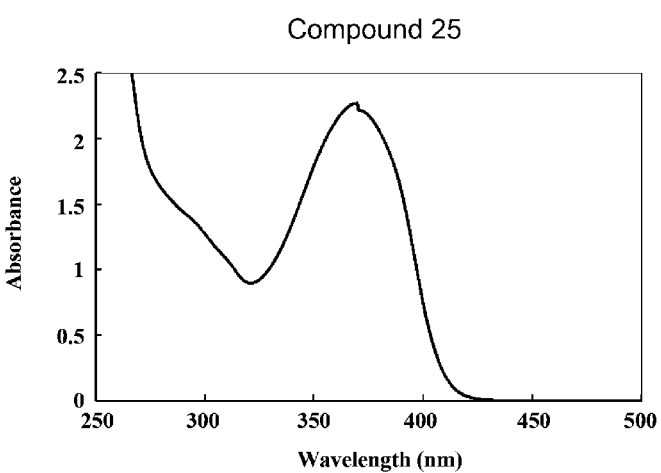
FIG. 26 is an ultraviolet-visible absorption spectrum (UV chart) of Compound 25 according to a working example of the present invention.
Figure 27:
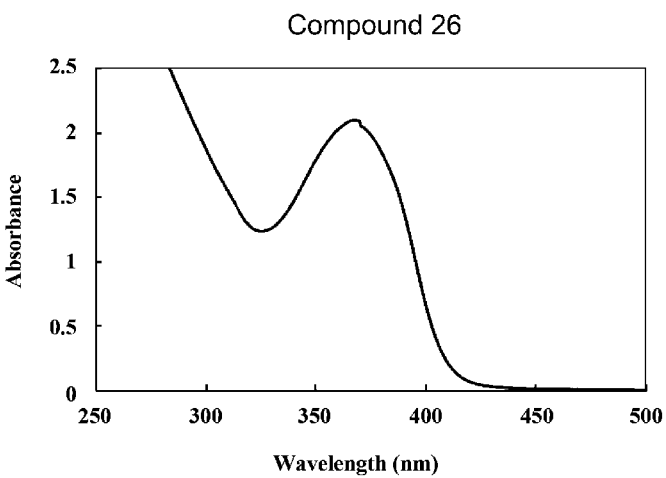
FIG. 27 is an ultraviolet-visible absorption spectrum (UV chart) of Compound 26 according to a working example of the present invention.
Figure 28:
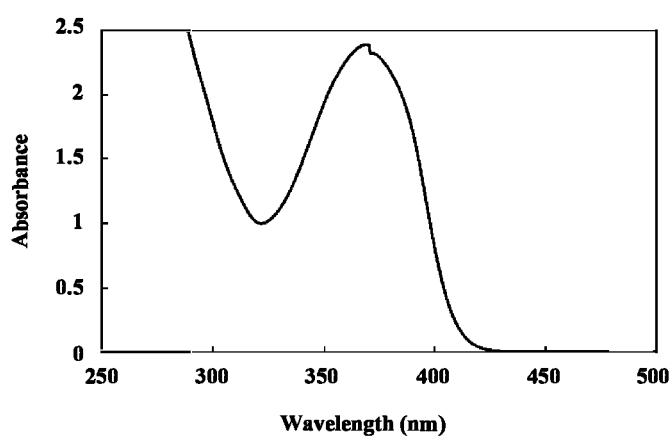
FIG. 28 is an ultraviolet-visible absorption spectrum (UV chart) of Compound 27 according to a working example of the present invention.
Figure 29:
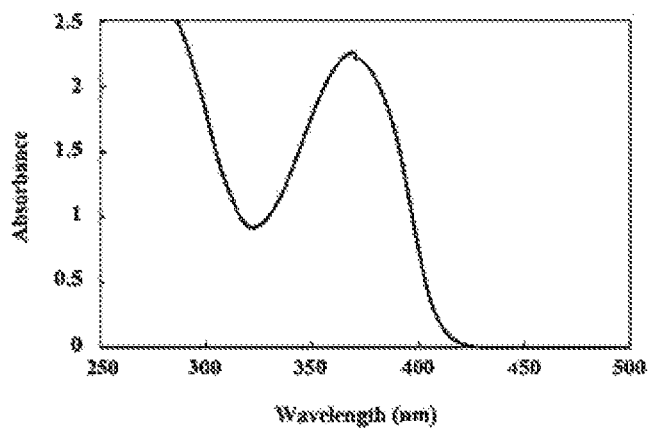
FIG. 29 is an ultraviolet-visible absorption spectrum (UV chart) of Compound 28 according to a working example of the present invention.

For Compounds 1, 4, 11, and 12, 50 μL of the solution obtained above was spin-coated on a slide glass, and the solvent was removed, whereby a film having a film thickness of 1 to 10 μm was produced. Further, the absorbance of the obtained film was measured by an ultraviolet-visible spectrophotometer (FIG. 13).

From ultraviolet-visible absorption spectrum measurement, it was confirmed that the polymers containing Compounds 1 and 4 of the present invention were superior to Compounds 11 and 12 in terms of yellowing inhibition and long wavelength absorption.

TABLE 4

| Compound No. | Structural formula | Transparency of polymer |
|---|---|---|
| Working example 25 | 1 — acrylate-O(CH₂)₆S-benzotriazole-phenol(HO, tBu, Me) | ○ |
| Working example 26 | 2 — methacrylate-O(CH₂)₂S-benzotriazole-phenol(HO, tBu, Me) | ○ |
| Working example 27 | 3 — methacrylate-O(CH₂)₃S-benzotriazole-phenol(HO, tBu, Me) | ○ |
| Working example 28 | 4 — methacrylate-O(CH₂)₆S-benzotriazole-phenol(HO, tBu, Me) | ○ |

TABLE 4-continued

| Compound No. | Structural formula | Transparency of polymer |
|---|---|---|
| Working example 29 | 5 | ○ |
| Working example 30 | 6 | ○ |

5. Evaluation of Elution (Bleeding-Out) from Film

In the above evaluation (1) of the reactivity, since the protons of the reactive groups disappeared almost entirely and the ultraviolet absorbers were immobilized in the resin, it is suggested that they can maintain the transparency and the ultraviolet absorption capability for along period of time without bleeding out. In order to actually confirm the elution and bleeding-out of the ultraviolet absorber taken into a film, films using Compounds 4 and 12 were prepared by the following procedures: as for Compound 4, 1 mL of a solution obtained by "3. Reactivity Evaluation (1)", and as for Compound 12.1 mL of a solution obtained by adding Compound 12 to a solution obtained by polymerizing only methyl methacrylate under the conditions of "3. Reactivity Evaluation (1)", were each applied to a slide glass, and then the solvent was removed to prepare a transparent film respectively. The obtained film/glass slides were immersed in 135 ml of heptane in a constant temperature bath at 60° C. for 2.5 hours, then the heptane was distilled off under reduced pressure, and the eluted material was dissolved in THF and confirmed by HPLC (High Performance Liquid Chromatography, Ultimete3000 made by Thermo Fisher Scientific K.K.).

As a result, the film using Compound 12 having no reactive functional group became cloudy, and the peak of Compound 12 was detected in the eluate, and thus elution was confirmed.

On the other hand, Compound 4 having a reactive functional group was transparent in the film after immersion, and the peak of Compound 4 was not detected in the eluate, and thus elution was not confirmed.

As a result of the above, it was suggested that the compounds of the present invention having a reactive functional group react with a monomer and is immobilized in a resin, do not bleed out or elute, maintain transparency, enabling an ultraviolet absorbing ability to be maintained for a long period of time.

6. Evaluation of Solubility and Reactivity in Various Monomers (2)

In the combinations shown in Table 5, methyl methacrylate of (meth)acrylate-based monomer, styrene of styrene-based monomer, vinyl acetate of vinyl-based monomer, dimethylacrylamide of acrylamide-based monomer, and hexadiene of olefin-based monomer were added to Compounds 1 to 6, 10, and 11 (0.1 g) so as to obtain predetermined concentrations, followed by irradiating them with ultrasonic waves for 5 minutes to confirm solubility, and then left at room temperature (20 to 30° C.) for 4 hours to confirm the presence or absence of precipitation, thereby determining the maximum solubilities.

Then, Compounds 1 to 6, 10, and 11 were added and dissolved at the maximum solubility concentrations with respect to the monomers of methyl methacrylate, styrene, and vinyl acetate; nitrogen substitution was performed thereto for 1 hour; then 0.03 mol % of 1,1'-azobis (cyclohexane-1-carbonitrile) was added with respect to the monomers; and the mixture was heated and stirred at 90 to 96° C. for 10 hours to perform copolymerization reaction, thus confirming the transparency of the polymer. The table shows the dissolvable maximum concentrations and the transparency of each polymer as evaluated by the following criteria (Table 5).

Evaluation Criteria
○: Clear with no cloudiness
Δ: Some cloudiness observed, but clear
x: Poor transparency due to cloudiness observed As a result, as compared with the reactive ultraviolet absorbers (Compounds 10 and 11) of the comparative examples, all of Compounds 1 to 6 of the present invention could be added to methyl methacrylate of the (meth)acrylate monomer and styrene of styrene-based monomer at high concentrations, and there could be obtained polymers having good transparency.

Also, similar solubility properties were exhibited for vinyl acetate as a vinyl-based monomer, dimethylacrylamide as an acrylamide-based monomer, and olefin-based hexadiene, so that Compounds 1 to 3, 5, and 6 allowed transparent polymers to be obtained in the vinyl acetate system.

With the same evaluation method, 2 wt % of Compound 1, 5 wt % of Compound 2, 5 wt % of Compound 3, and 1 wt % of Compound 4 were each soluble in acrylonitrile as a vinyl-based monomer as well.

TABLE 5

| Com-pound No. | Structural formula | (meth)acrylate-based Methyl (meth)acrylate | | Styrene-based Styrene | | Vinyl-based Vinyl acetate | | Acrylamide-based Dimethylacrylamide | | Olefin-based Hexadiene | |
|---|---|---|---|---|---|---|---|---|---|---|---|
| | | Maximum solubility [wt %] | Transparency of polymer | Maximum solubility [wt %] | Transparency of polymer | Maximum solubility [wt %] | Transparency of polymer | Maximum solubility [wt %] | Transparency of polymer | Maximum solubility [wt %] | Transparency of polymer |
| Working example 31 | 1 | 20 | ○ | 25 | ○ | 15 | △ | 20 | — | 10 | — |
| Working example 32 | 2 | 20 | ○ | 25 | ○ | 15 | △ | 15 | — | 3 | — |
| Working example 33 | 3 | 20 | ○ | 25 | ○ | 12 | △ | 11 | — | 5 | — |
| Working example 34 | 4 | 12 | ○ | 25 | ○ | — | | — | | — | — |

TABLE 5-continued

| Compound No. | Structural formula | (meth)acrylate-based Methyl (meth)acrylate | | Styrene-based Styrene | | Vinyl-based Vinyl acetate | | Acrylamide-based Dimethylacrylamide | | Olefin-based Hexadiene | |
|---|---|---|---|---|---|---|---|---|---|---|---|
| | | Maximum solubility [wt %] | Transparency of polymer | Maximum solubility [wt %] | Transparency of polymer | Maximum solubility [wt %] | Transparency of polymer | Maximum solubility [wt %] | Transparency of polymer | Maximum solubility [wt %] | Transparency of polymer |
| Working example 35 | 5 | 15 | ○ | 25 | ○ | 13 | △ | 15 | — | 5 | — |
| Working example 36 | 6 | 20 | ○ | 25 | ○ | 15 | △ | 15 | — | 10 | — |
| Comparative example 9 | 10 | ≤10 | — | ≤20 | — | ≤10 | — | ≤9 | — | 1 | — |
| Comparative example 10 | 11 | 11 | ○ | 21 | ○ | 11 | △ | 10 | — | 2 | — |

7. Evaluation of 5% Weight Reduction Temperature (1)

Compounds 1 to 8 and 10 to 12 were measured using a differential thermogravimetric simultaneous measurement device (TG/DTA6200, manufactured by SII Corporation) at a temperature increasing rate of 10° C./min and within a measurement range of 25° C. to 550° C., and the temperature at which 5 wt % reduction as the weight change (TG) took place was read (Table 6).

As a result, compared with Compounds 10 to 12 of the comparative examples, the 5% weight reduction decomposition temperatures of the compounds of the present invention were each 280° C. or higher, and among these, Compounds 1, 4 to 6, 8 were as high as 310° C. or higher, and thus the heat resistance was improved. In addition, the 5% weight reduction decomposition temperatures were in the relationship of those of Compounds 1 to 8>that of Compound 10>those of Compounds 11 and 12, and thus it was suggested that the heat resistance was improved by introducing a sulfur containing group (thioether group), introducing an acryloyloxy group, and particularly introducing an aromatic group in X (those of Compounds 5 and 6>that of Compound 4).

That is, 5% weight reduction decomposition temperatures of Compounds 1 to 8 are higher than the softening temperatures of most general resins of 100 to 250° C. ("Clearly-understandable plastics", supervised by the Japan Plastics Industry Federation, published by Japan Jitsugyo Publishing) and can be applied to thermoplastic resins requiring molding processing temperatures higher than 200 to 250° C.; can also react at high temperatures, and can impart ultraviolet absorption capability of resin members and suppress deterioration of transparency of transparent resin members.

TABLE 6

| | Compound No. | Structural formula | 5% weight reduction temperature [° C.] |
|---|---|---|---|
| Working example 37 | 1 | (structure with O(CH$_2$)$_6$S linker, benzotriazole, HO, tBu, Me) | 321 |
| Working example 38 | 2 | (structure with O(CH$_2$)$_2$S linker, benzotriazole, HO, tBu, Me) | 285 |
| Working example 39 | 3 | (structure with O(CH$_2$)$_3$S linker, benzotriazole, HO, tBu, Me) | 292 |
| Working example 40 | 4 | (structure with O(CH$_2$)$_6$S linker, methacrylate, benzotriazole, HO, tBu, Me) | 317 |
| Working example 41 | 5 | (methacrylate-phenyl-S-benzotriazole structure, HO, tBu, Me) | 323 |

TABLE 6-continued

| Compound No. | | Structural formula | 5% weight reduction temperature [° C.] |
|---|---|---|---|
| Working example 42 | 6 | 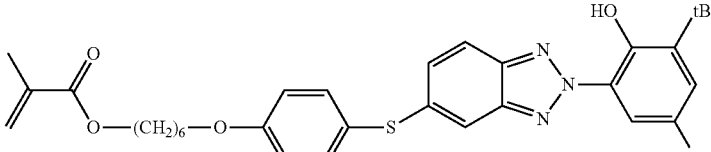 | 382 |
| Working example 43 | 7 | 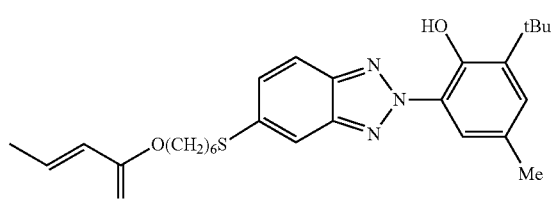 | 304 |
| Working example 44 | 8 | 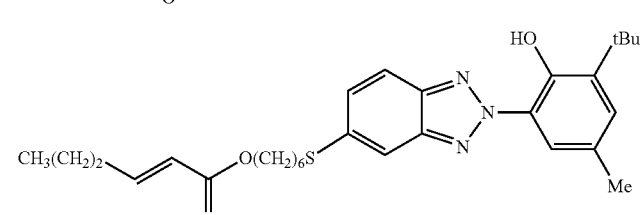 | 312 |
| Comparative example 11 | 10 | 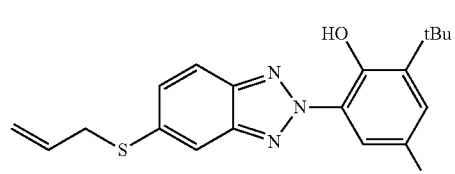 | 252 |
| Comparative example 12 | 11 | 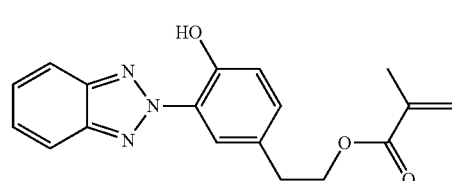 | 249 |
| Comparative example 13 | 12 | 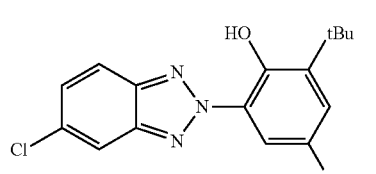 | 230 |

8. Evaluation of UV Absorption Performance (2)

Compounds 11 to 28 were diluted with 100 μM of chloroform and placed in a 10-mm quartz cell, and the absorbance spectra were measured using an ultraviolet-visible spectrophotometer (V-550, manufactured by JASCO Corporation)(FIGS. 11,12,14 to 29).

As a result, it was shown that Compounds 13 to 28 of the present invention have an absorption band in the wavelength region of ultraviolet rays and function as an ultraviolet absorber when added to a film or a resin.

It was confirmed that the benzotriazole-based compounds 13 to 28 of the present invention in which the group of the above formula (i-3) was introduced into the thioether group (formula (i-1)) had a peak top shifted into the long wavelength region compared with the conventional ultraviolet absorbers: (Compound 11) having an ester group and (Compound 12) of the long-wavelength absorption type, and were superior in ultraviolet absorption in the vicinity of 360 to 400 nm in the longer wavelength region. As for Compounds 17 to 19 and 21 to 28 having an aromatic group introduced into $X^a$ of formula (i-3) and comprising a π electron system with a benzotriazole group-sulfur atom-aromatic group ($X^a$), the $X^a$ has a larger absorption peak (greater absorbance) in the region of 250 to 320 nm than Compounds 14 and 16 of alkylene group, and among them, Compound 19 having an extended π electron system such that an aromatic group is introduced into $X^a$ and $X^b$ and an oxygen-containing group of an ester group is introduced into $A^2$; and Compounds 21 to 28 having an aromatic group introduced into X and a nitrogen-containing group such as an amide group or a urea group introduced into $A^2$, among which Compounds 25 to 28 of urea group have an absorption peak in a region of 250 to 320 nm that is even greater (absorbance becomes greater) and can absorb an ultraviolet in a wide range of from a lower wavelength to a longer wavelength.

The absorption peak (maximum absorption wavelength: max) and absorbance in the wavelength range of 350 to 390 nm were read from the absorption spectra of Compounds 11 to 28, and a molar extinction coefficient (maximum molar extinction coefficient: $\varepsilon_{max}$) of the peak was obtained by the following formula (Table 7):

Molar extinction coefficient:$\varepsilon_{max}$(L/(mol·cm))=$A$:
Absorbance/[$c$:Mol concentration(mol/L)×1:Cell optical length(cm)] [Equation 3]

As a result, it was shown that Compounds 13 to 28 of the present invention have a higher molar extinction coefficient of 21,000 or more than Compounds 11 and 12, and efficiently absorb ultraviolet rays with a small additive amount.

In addition, from the absorption spectra of Compounds 11 to 28, assuming that an intersection of a long-wavelength side absorption spectrum in the absorption peak at 350 to 390 nm and a baseline (a line where the slope of the absorption spectrum at 30 to 500 nm is zero) is set as a peak end (for example: FIG. 1), the absolute value of the slope of the absorption peak on the long-wavelength side in the wavelength region at 350 to 390 nm was obtained by the following equation (Table 8):

|Slope of absorption peak on long wavelength side in wavelength region of 350 to 390nm|=|(Absorbance at peak end−Absorbance at absorption peak in wavelength region of 350 to 390 nm)/(Absorption wavelength at peak end−Wave length at absorption peak in wavelength region of 350 to 390 nm)| [Equation 4]

As a result, the absolute values of slopes of Compounds 13 to 28 we all 0.040 or more, which were larger than those of Compounds 11 and 12 (absolute values of slopes: 0.032 to 0.038) so that the peaks were sharp, and Compounds 13 to 28 of the present invention had a reduced cut at 400 to 500 nm (visible region), and thus it was suggested that they are excellent in the yellow suppressing effect on a film, a resin member, and particularly, a transparent resin member.

TABLE 7

| | Compound No. | Structural formula | Wave length at absorption peak in wavelength region of 350 to 390 nm (maximum absorption wavelength: $\lambda_{max}$) [nm] | Molar extinction coefficient at peak in the left column (maximum molar extinction coefficient: $\varepsilon_{max}$) [L/(mol · cm)] |
|---|---|---|---|---|
| Working example 45 | 13 | | 365 | 22200 |
| Working example 46 | 14 | | 365 | 22100 |
| Working example 47 | 15 | | 367 | 22300 |
| Working example 48 | 16 | | 367 | 22200 |

TABLE 7-continued

| Compound No. | | Structural formula | Wave length at absorption peak in wavelength region of 350 to 390 nm (maximum absorption wavelength: $\lambda_{max}$) [nm] | Molar extinction coefficient at peak in the left column (maximum molar extinction coefficient: $\varepsilon_{max}$) [L/(mol · cm)] |
|---|---|---|---|---|
| Working example 49 | 17 | | 366 | 22400 |
| Working example 50 | 18 | | 366 | 22200 |
| Working example 51 | 19 | | 366 | 22900 |
| Working example 52 | 20 | | 368 | 22000 |
| Working example 53 | 21 | | 369 | 22400 |
| Working example 54 | 22 | | 369 | 22300 |
| Working example 55 | 23 | | 369 | 23400 |

TABLE 7-continued

| Compound No. | | Structural formula | Wave length at absorption peak in wavelength region of 350 to 390 nm (maximum absorption wavelength: $\lambda_{max}$) [nm] | Molar extinction coefficient at peak in the left column (maximum molar extinction coefficient: $\varepsilon_{max}$) [L/(mol · cm)] |
|---|---|---|---|---|
| Working example 56 | 24 | (naphthalene-C(O)NH-C6H4-S-benzotriazole-N-phenol(HO, tBu, Me)) | 368 | 23600 |
| Working example 57 | 25 | CH3CH2-NH-C(O)-NH-C6H4-S-benzotriazole-N-phenol(HO, tBu, Me) | 370 | 22700 |
| Working example 58 | 26 | CH3(CH2)17-NH-C(O)-NH-C6H4-S-benzotriazole-N-phenol(HO, tBu, Me) | 368 | 21700 |
| Working example 59 | 27 | Ph-NH-C(O)-NH-C6H4-S-benzotriazole-N-phenol(HO, tBu, Me) | 369 | 23900 |
| Working example 60 | 28 | CH3O-C6H4-NH-C(O)-NH-C6H4-S-benzotriazole-N-phenol(HO, tBu, Me) | 370 | 22600 |
| Comparative exam 14 | 11 | benzotriazole-phenol(HO)-CH2CH2-O-C(O)-C(CH3)=CH2 | 341 | 18300 |
| Comparative exam 15 | 12 | Cl-benzotriazole-N-phenol(HO, tBu, Me) | 353 | 16300 |

TABLE 8

| Compound No. | | Structural formula | Absorbance at absorption peak in wavelength region of 350 to 390 nm | Absorbance at peak end | Absorption wavelength at peak end [nm] | Absolute value of slope of absorption peak on long wavelength side in wavelength region of 350 to 390 nm |
|---|---|---|---|---|---|---|
| Working example 61 | 13 | | 2.22 | 0.03020 | 419 | 0.040 |
| Working example 62 | 14 | | 2.21 | 0.02594 | 419 | 0.040 |
| Working example 63 | 15 | | 2.23 | 0.00820 | 423 | 0.040 |
| Working example 64 | 16 | | 2.22 | 0.01846 | 420 | 0.041 |
| Working example 65 | 17 | | 2.24 | 0.01899 | 422 | 0.040 |
| Working example 66 | 18 | | 2.22 | 0.02575 | 420 | 0.041 |
| Working example 67 | 19 | | 2.29 | 0.02244 | 422 | 0.041 |

TABLE 8-continued

| Compound No. | Structural formula | Absorbance at absorption peak in wavelength region of 350 to 390 nm | Absorbance at peak end | Absorption wavelength at peak end [nm] | Absolute value of slope of absorption peak on long wavelength side in wavelength region of 350 to 390 nm |
|---|---|---|---|---|---|
| Working example 68 | 20 | 2.20 | 0.00489 | 423 | 0.040 |
| Working example 69 | 21 | 2.24 | 0.00955 | 424 | 0.041 |
| Working example 70 | 22 | 2.23 | 0.01382 | 424 | 0.041 |
| Working example 71 | 23 | 2.34 | 0.01418 | 424 | 0.043 |
| Working example 72 | 24 | 2.36 | 0.02000 | 424 | 0.042 |
| Working example 73 | 25 | 2.27 | 0.01740 | 424 | 0.042 |
| Working example 74 | 26 | 2.17 | 0.15007 | 419 | 0.040 |
| Working example 75 | 27 | 2.39 | 0.01868 | 425 | 0.042 |

TABLE 8-continued

| Compound No. | | Structural formula | Absorbance at absorption peak in wavelength region of 350 to 390 nm | Absorbance at peak end | Absorption wavelength at peak end [nm] | Absolute value of slope of absorption peak on long wavelength side in wavelength region of 350 to 390 nm |
|---|---|---|---|---|---|---|
| Working example 76 | 28 | (structure) | 2.26 | 0.01853 | 423 | 0.042 |
| Comparative example 16 | 11 | (structure) | 1.83 | 0.00690 | 388 | 0.038 |
| Comparative example 17 | 12 | (structure) | 1.76 | 0.00722 | 430 | 0.032 |

9. Evaluation of 5% Weight Reduction Temperature (2)

The compounds of the present invention were measured using a differential thermogravimetric simultaneous measurement device (TG/DTA6200, manufactured by SII Corporation) at a temperature increasing rate of 10° C./min and within a measurement range of 25° C. to 550° C., and the temperature at which 5 w % reduction as the weight change (TG) took place was read (Table 9).

After comparing the compounds 13, 15, 16 and 20 in which $X^a$ and $X^b$ in formula i-3 represent alkylene groups with the compound 29 (277° C.) of the comparative example 18 in which an alkylene group(s) are contained in the sulfur-containing group, it was confirmed that the compounds 13, 15, 16 and 20 of the present invention in which a nitrogen-containing group and/or oxygen-containing group (esters, urethanes) having double bonds have been introduced each exhibited high 5% weight reduction decomposition temperature of not lower than 280° C. Particularly, the compounds 15, 16 and 20 exhibited 5% weight reduction decomposition temperatures of not lower than 290° C., and the compounds 15 and 16 even exhibited 5% weight reduction decomposition temperatures of not lower than 310° C., which indicated that the heat resistance had improved. Moreover, these 5% weight reduction decomposition temperatures were found to be in a relationship of compounds 13, 15, 16 and 20>compound 29>compounds 11, 12; it was suggested that the heat resistance could be improved by introducing a sulfur-containing group (thioether group), and by farther introducing a nitrogen-containing group and/or oxygen-containing group having double bonds.

In addition, after comparing the compounds 14, 17, 18, 19, 21, 22, 23 and 24 in which at least one of $X^a$ and $X^b$ represents an aromatic group with the compound 30 (293° C.) of the comparative example 19 in which an aromatic group(s) are contained in the sulfur-containing group, it was confirmed that the compounds 14, 17, 18, 19, 21, 22, 23 and 24 of the invention in which a nitrogen-containing group and/or oxygen-containing group (esters, amides) having double bonds have been introduced each exhibited a high 5% weight reduction decomposition temperature of not lower than 310° C., which indicated that the heat resistance had improved.

In this way, it was suggested that in order to raise the 5% weight reduction decomposition temperature, it was essential to introduce a nitrogen-containing group and/or oxygen-containing group having double bonds, typical examples of which include esters, amides and urethanes.

Meanwhile, as for the working examples 77 to 88, the following tendencies were observed with regard to a correlation between X, $X^b$ and $A^2$ in the formula (i-3); and the heat resistance (5% weight reduction decomposition temperature).

As for the number of the carbon atom in the alkylene group of X, after comparing the 5% weight reduction decomposition temperatures of the compounds 13, 15 and 16 in which $X^a$ represents an alkylene group, $X^b$ represents an alkyl group, and $A^2$ represents an ester group, it was confirmed that the 5% weight reduction decomposition temperatures of the compound 13 (number of carbon atoms 2, 283° C.), compound 15 (number of carbon atoms 3, 327° C.) and compound 16 (number of carbon atoms 6, 357° C.) in which $X^a$ has not less than 2 carbo atoms were higher than that of the compound 29 (277° C.) of the comparative example. Particularly, the compounds 15 and 16 in which the number of the carbon atoms was not smaller than 3 exhibited a 5% weight reduction decomposition temperature higher than that of the compound 13, which suggested that these compounds were superior in heat resistance.

As for the number of the carbon atoms in the alkyl group of $X^b$, when $X^a$ represents an alkylene group, $X^b$ represents an alkyl group, and $A^2$ represents an ester group, after comparing the 5% weight reduction decomposition temperatures of the compounds 13, 15 and 16 in which $X^a$ represents an alkylene group, $X^b$ represents an alkyl group, and $A^2$ represents an ester group, it was confirmed that the 5% weight reduction decomposition temperatures of the compound 13 (number of carbon atoms 1, 283° C.), compound 15 (number of carbon atoms 9, 327° C.) and compound 16 (number of carbon atom 17, 357° C.) in which $X^b$ has not less than 1 carbo atom were higher than that of the compound 29 (277° C.) of the comparative example. Particularly, the compounds 15 and 16 in which the number of the carbon atoms was not smaller than 6 exhibited a 5% weight reduction decomposition temperature higher than that of the compound 13, and the compound 16 in which the number of the carbon atoms was not smaller than 14 exhibited a 5% weight reduction decomposition temperature higher than those of the compounds 13 and 15, which suggested that these compounds were superior in heat resistance.

As for $A^2$, ater comparing the 5% weight reduction decomposition temperatures of the compounds 16 and 20 in which $X^a$ represents an alkylene group, and $X^b$ represents an alkyl group, it was confirmed that the compound 16 (357° C.) containing an ester group exhibited a 5% weight reduction decomposition temperature higher than that of the compound 20 (299° C.) containing a urethane group; after comparing the 5% weight reduction decomposition temperatures of the compounds 18 and 22 in which $X^a$ represents an aromatic group, $X^b$ represents an alkyl group, it was confirmed that the compound 22 (371° C.) containing amide exhibited a 5% weight reduction decomposition temperature higher than that of the compound 18 (346'C) containing an ester group; and after comparing the 5% weight reduction decomposition temperatures of the compounds 17 and 21 in which $X^a$ represents an aromatic group and $X^b$ represents an alkyl group, and the compounds 19 and 23 in which $X^a$ represents an aromatic group and $X^b$ represents an aromatic group, it was confirmed that the compounds 21 (352° C.) and 23 (389° C.) containing amide exhibited 5% weight reduction decomposition temperatures higher than those of the compounds 17 (319° C.) and 19 (365° C.) containing ester groups. That is, even among the nitrogen-containing groups and/or oxygen-containing groups having double bonds, heat resistance was found to be superior in the order of urethane, ester and amide.

As for $A^2$, after comparing the 5% weight reduction decomposition temperatures of compounds in which $X^a$ and $X^b$ are identical to each other, and $A^2$ represents ester and amide, it was confirmed that in each of the pairs of the compounds 17 (319° C.) and 21 (352° C.), compounds 18 (346° C.) and 22 (371'C), and compounds 19 (365° C.) and 23 (389° C.), the 5% weight reduction decomposition temperature was higher when amide was employed than when ester was employed, which indicated that the heat resistance was superior in the case of amide.

When $X^a$ and $X^b$ represent aliphatic hydrocarbon groups (alkyl group, alkylene group) and aromatic groups, or when $X^a$ and $X^b$ represent aliphatic hydrocarbon groups (alkyl group, alkylene group), as for a total number of the carbon atoms in $X^a$ and $X^b$, after comparing the 5% weight reduction decomposition temperatures of the compounds 13 to 18 in which $A^2$ represents an ester group, it was confirmed that the compounds 17 (number of carbon atoms 7, 319° C.), 14 (number of carbon atoms 8, 319° C.), 15 (number of carbon atoms 12, 32° C.), 16 (number of carbon atoms 23, 357° C.) and 18 (number of carbon atoms 23, 346° C.) in which the total number of the carbon atoms was not smaller than 5 exhibited 5% weight reduction decomposition temperatures higher than that of the compound 13 (number of carbon atoms 3, 283° C.); that the compounds 15, 16 and 18 in which the number of the carbon atoms was not smaller than 10 exhibited 5% weight reduction decomposition temperatures higher than those of the compounds 13, 17 and 14; and that the compounds 16 and 18 in which the number of the carbon atoms was not smaller than 18 exhibited 5% weight reduction decomposition temperatures higher than those of the compounds 13, 17, 14 and 15, which indicated that these compounds were superior in heat resistance.

Further, as for a combination of $X^a$ and $X^b$, after likewise comparing the compounds 16, 18 and 19 in which the number of the carbon atoms of $X^a$ is 6, and $A^2$ represents an ester group, there was observed a tendency where the compound 19 (365° C.) composed of $X^a$: aromatic group and $X^b$: aromatic group had a 5% weight reduction decomposition temperature higher than those of the compound 18 (346° C.) composed of $X^b$: aliphatic hydrocarbon group (alkyl group, alkylene group) and $X^b$: aromatic group; and the compound 16(357° C.) composed of $X^a$ aliphatic hydrocarbon group (alkyl group, alkylene group) and $X^b$: aliphatic hydrocarbon group (alkyl group, alkylene group).

TABLE 9

| Compound No. | Structural formula | 5% weight reduction temperature [° C.] |
|---|---|---|
| Working example 77 | 13 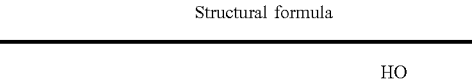 | 283 |

TABLE 9-continued

| | Compound No. | Structural formula | 5% weight reduction temperature [° C.] |
|---|---|---|---|
| Working example 78 | 14 | | 319 |
| Working example 79 | 15 | | 327 |
| Working example 80 | 16 | | 357 |
| Working example 81 | 17 | | 319 |
| Working example 82 | 18 | | 346 |
| Working example 83 | 19 | | 365 |
| Working example 84 | 20 | | 299 |

TABLE 9-continued
| | Compound No. | Structural formula | 5% weight reduction temperature [° C.] |
|---|---|---|---|
| Working example 85 | 21 | 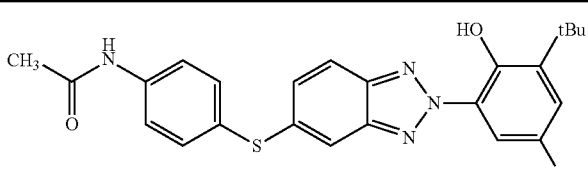 | 352 |
| Working example 86 | 22 | 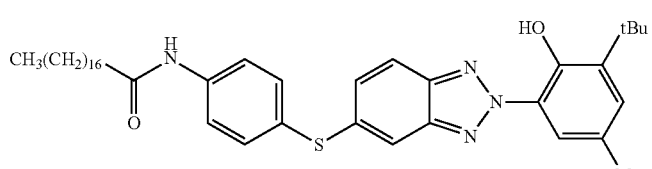 | 371 |
| Working example 87 | 23 | 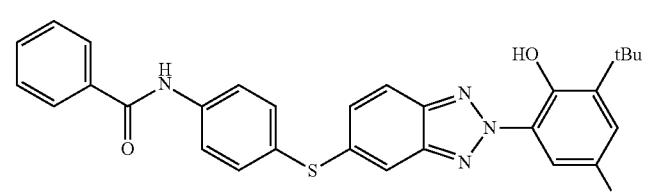 | 389 |
| Working example 88 | 24 | 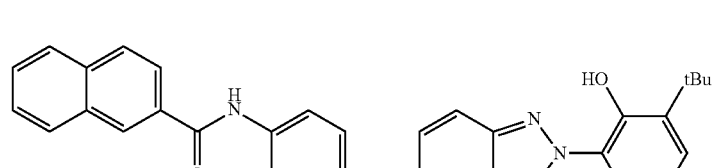 | 376 |
| Comparative exam 18 | 29 | 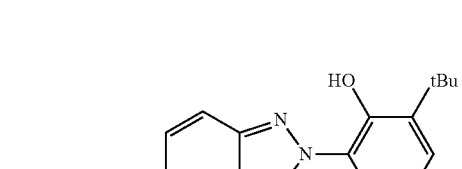 | 277 |
| Comparative exam 19 | 30 | 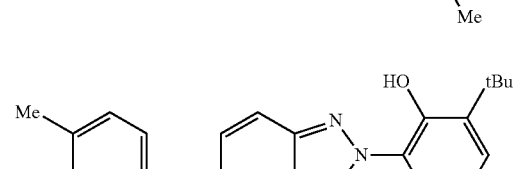 | 293 |
| Comparative exam 20 | 12 | 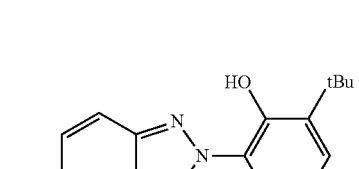 | 230 |

We claim:

1. A benzotriazole compound represented by the following formula (I):

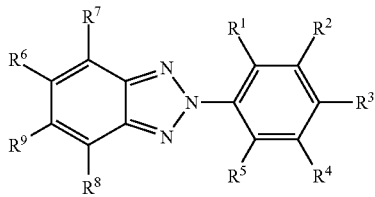

wherein each of $R^1$ to $R^9$ independently represents a monovalent group selected from a monovalent sulfur-containing group represented by the following formula (i-1), a hydrogen atom, a hydrocarbon group having 1 to 10 carbon atoms, an aromatic group, an unsaturated group, a nitrogen-containing group, a sulfur-containing group, an oxygen-containing group, a phosphorus-containing group, an alicyclic group and a halogen atom, provided that at least one of $R^1$ to $R^9$ is the monovalent sulfur-containing group represented by the following formula (i-1):

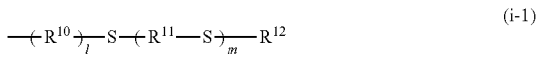

wherein l represents 0; m represents an integer of 0 to 3; $R^{10}$ represents a divalent hydrocarbon group having 1 to 20 carbon atoms in which hydrogen atoms may be substituted with, at least one of two ends may be interrupted by, or carbon-carbon bonds may be interrupted by a monovalent or divalent group selected from an aromatic group, an unsaturated group, a nitrogen-containing group, a sulfur-containing group, an oxygen-containing group, a phosphorus-containing group, an alicyclic group and a halogen atom; $R^{11}$ represents a divalent hydrocarbon group having 1 to 20 carbon atoms in which hydrogen atoms may be substituted with, at least one of two ends may be interrupted by, or carbon-carbon bonds may be interrupted by a monovalent or divalent group selected from an aromatic group, an unsaturated group, a nitrogen-containing group, a sulfur-containing group, an oxygen-containing group, a phosphorus-containing group, an alicyclic group and a halogen atom with the proviso that each of $R^{11}$ is independent when m is not smaller than 2; $R^{12}$ represents a monovalent group expressed by the following formula (i-2):

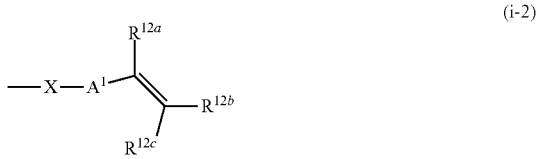

wherein each of $R^{12a}$, $R^{12b}$ and $R^{12c}$ independently represents a hydrogen atom or a monovalent hydrocarbon group having 1 to 18 carbon atoms; $A^1$ represents a divalent group selected from a nitrogen-containing group, an oxygen-containing group, a sulfur-containing group, a phosphorus-containing group and a phenylene group; X represents a divalent group selected from $-X^1-$, $-X^2-$, $-X^1-(Y)_p-X^2-$, $-X^2-(Y)_p-X^1-$ and $-X^2-(Y)_p-X^2-$, wherein $X^1$ represents a divalent hydrocarbon group having 1 to 20 carbon atoms in which hydrogen atoms may be substituted with, at least one of two ends may be interrupted by, or carbon-carbon bonds may be interrupted by a monovalent or divalent group selected from an aromatic group, an unsaturated group, a nitrogen-containing group, a sulfur-containing group, an oxygen-containing group, a phosphorus-containing group, an alicyclic group and a halogen atom; $X^2$ represents a divalent aromatic group; Y represents a hetero atom; and p represents an integer of 0 or 1.

2. The benzotriazole compound according to claim 1, wherein $A^1$ in formula (i-2) is a divalent group selected from a nitrogen-containing group, an oxygen-containing group, a sulfur-containing group, a phosphorus-containing group, each having a double bond, and a phenylene group.

3. The benzotriazole compound according to claim 1, wherein l and m in formula (i-1) are 0, and $R^{12c}$ in formula (i-2) is a hydrogen atom.

4. The benzotriazole compound according to claim 1, wherein $A^1$ in formula (i-2) is a divalent group selected from an ester group, a phenylene group, and an amide group.

5. The benzotriazole compound according to claim 1, wherein in X of formula (i-2), $X^1$ represents an unsubstituted and uninterrupted divalent hydrocarbon group having 1 to 20 carbon atoms, $X^2$ represents a divalent aromatic group, and Y represents an oxygen atom or a sulfur atom.

6. The benzotriazole compound according to claim 5, wherein X in formula (i-2) is an alkylene group $-(CH_2)_n-$, wherein n is an integer of 1 to 20.

7. The benzotriazole compound according to claim 6, wherein X in formula (i-2) is an alkylene group $-(CH_2)_n-$, and n is an integer of 2 to 10.

8. The benzotriazole compound according to claim 7, wherein X in formula (i-2) is an alkylene group $-(CH_2)_n-$, and n is an integer of 3 to 10.

9. The benzotriazole compound according to claim 5, wherein $X^2$ in formula (i-2) is a phenylene group.

10. The benzotriazole compound according to claim 5, wherein X in formula (i-2) is $-X^2-(Y)_p-X^1-$, $X^1$ is an alkylene group $-(CH_2)_n-$ wherein n represents an integer of 1 to 20, $X^2$ is a phenylene group, and Y is an oxygen atom.

11. The benzotriazole compound according to claim 1, wherein $A^1$ in formula (i-2) is an ester group.

12. The benzotriazole compound according to claim 1, wherein the monovalent sulfur-containing group represented by formula (i-1) is present in any one of $R^6$ to $R^9$ of formula (I).

13. A polymer containing, as a raw material monomer, the benzotriazole compound according to claim 1.

14. A benzotriazole compound represented by the following formula (I):

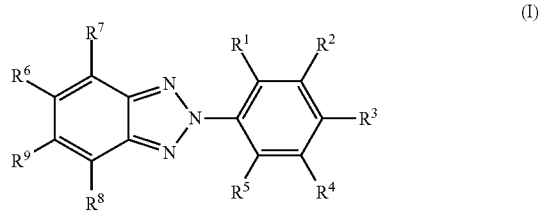

wherein each of $R^1$ to $R^9$ independently represents a monovalent group selected from a monovalent sulfur-containing group represented by the following formula (i-1), a hydrogen atom, a hydrocarbon group having 1 to 18 carbon atoms, an aromatic group, an unsaturated group, a nitrogen-containing group, a sulfur-containing group, an oxygen-containing group, a phosphorus-containing group, an alicyclic group, and a halogen atom, provided that at least one of $R^1$ to $R^9$ is the monovalent sulfur-containing group represented by the formula (i-1):

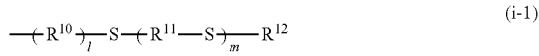

(i-1)

wherein l represents an integer of 0 or 1; m represents an integer of 0 to 3; $R^{10}$ represents a divalent hydrocarbon group having 1 to 20 carbon atoms in which hydrogen atoms may be substituted with, at least one of two ends may be interrupted by, or carbon-carbon bonds may be interrupted by a monovalent or divalent group selected from an aromatic group, an unsaturated group, a nitrogen-containing group, a sulfur-containing group, an oxygen-containing group, a phosphorus-containing group, an alicyclic group, and a halogen atom; $R^{11}$ represents a divalent hydrocarbon group having 1 to 20 carbon atoms in which hydrogen atoms may be substituted with, at least one of two ends may be interrupted by, or carbon-carbon bonds may be interrupted by a monovalent or divalent group selected from an aromatic group, an unsaturated group, a nitrogen-containing group, a sulfur-containing group, an oxygen-containing group, a phosphorus-containing group, an alicyclic group and a halogen atom with the proviso that each of $R^{11}$ is independent when m is not smaller than 2; $R^{12}$ represents a monovalent group represented by the following formula (i-3):

(i-3)

wherein, $A^2$ represents a divalent group selected from an ester group having the configuration —OC(=O), a urethane group, an amide group, and a urea group; $X^a$ represents a divalent group selected from —$X^{a1}$—, —$X^{a2}$—, —$X^{a1}$—$(Y^a)_q$—$X^{a2}$—, —$X^{a2}$—$(Y^a)_q$—$X^{a1}$— and —$X^{a2}$—$(Y^a)_q$—$X^{a2}$— wherein $X^{a1}$ represents a divalent hydrocarbon group having 1 to 20 carbon atoms in which hydrogen atoms may be substituted with, at least one of two ends may be interrupted by, or carbon-carbon bonds may be interrupted by a monovalent or divalent group selected from an aromatic group, an unsaturated group, a nitrogen-containing group, an oxygen-containing group, a phosphorus-containing group, an alicyclic group, and a halogen atom, wherein $X^{a2}$ represents a divalent aromatic group, $Y^a$ represents a heteroatom, and q represents an integer of 0 or 1; $X^b$ represents a monovalent group selected from —$X^{b1}$, —$X^{b2}$, —$X^{a1}$—$(Y^b)_r$—$X^{b2}$, —$X^{a2}$—$(Y^b)_r$—$X^{b1}$, and —$X^{a2}$—$(Y^b)_r$—$X^{b2}$ wherein $X^{b1}$ represents an alkyl group having 1 to 20 carbon atoms, wherein $X^{b2}$ represents a monovalent aromatic group, $Y^b$ represents a heteroatom, and r represents an integer of 0 or 1, provided that $X^{a1}$ and $X^{a2}$ are independently selected.

15. The benzotriazole compound according to claim 14, wherein $A^2$ in formula (i-3) is an ester group having the configuration —OC(=O)—.

16. The benzotriazole compound of claim 14, wherein l and m in formula (i-1) are 0.

17. The benzotriazole compound according to claim 14, wherein in $X^a$ of formula (i-3), $X^{a1}$ represents an unsubstituted and uninterrupted divalent hydrocarbon group of 1 to 20 carbon atoms, $X^{a2}$ represents a divalent aromatic group, $Y^a$ represents an oxygen atom or sulfur atom, wherein in $X^b$, $X^{b1}$ represents an alkyl group having 1 to 20 carbon atoms, $X^{b2}$ represents a monovalent aromatic group, and $Y^b$ represents an oxygen atom or a sulfur atom, wherein $X^{a1}$ and $X^{a2}$ are each independently selected.

18. The benzotriazole compound according to claim 17, wherein $X^a$ in formula (i-3) is an alkylene group —$(CH_2)_n$— wherein n represents an integer of 1 to 20 or a unsubstituted and uninterrupted divalent aromatic group.

19. The benzotriazole compound according to claim 17, wherein $X^a$ in formula (i-3) is a divalent aromatic group.

20. The benzotriazole compound according to claim 14, wherein, in $X^b$ of formula (i-3), $X^{b1}$ represents an alkyl group having 1 to 20 carbon atoms, $X^{b2}$ represents a monovalent aromatic group, $Y^b$ represents an oxygen atom or a sulfur atom, $X^{a1}$ represents an unsubstituted and uninterrupted divalent alkyl group having 1 to 20 carbon atoms, and $X^{a2}$ represents a divalent aromatic group.

21. The benzotriazole compound according to claim 14, wherein the monovalent sulfur-containing group represented by formula (i-1) is present in any one of $R^6$ to $R^9$ of formula (I).

22. A composition to which a benzotriazole compound according to claim 14 is added.

23. An ultraviolet absorber comprising the benzotriazole compound according to claim 1.

24. An ultraviolet absorber comprising the benzotriazole compound according to claim 14.

25. The benzotriazole compound according to claim 1, wherein in the formula (I), the monovalent sulfur-containing group represented by the formula (i-1) is contained in $R^9$ at the 5-position, and wherein $R^1$, $R^2$, $R^3$, $R^4$ and $R^5$ each independently represent hydrogen, hydroxy, or a substituent selected from a hydrocarbon group having 1 to 18 carbon atoms; an aromatic group having 6 to 18 carbon atoms; an ether group having 1 to 18 carbon atoms; an alkoxy group having 1 to 18 carbon atoms; an ester group having 1 to 18 carbon atoms; a (meth)acryloyloxy group or polyoxyethylene group having 1 to 20 carbon atoms; or a hydrocarbon group having 1 to 18 carbon atoms, in which hydrogen atoms may be substituted with the abovementioned substituent groups, a base end may be interrupted by the abovementioned substituent groups, or carbon-carbon bonds may be interrupted by the abovementioned substituent groups.

26. The benzotriazole compound according to claim 14, wherein $R^1$, $R^2$, $R^3$, $R^4$ and $R^5$ each independently represent hydrogen, hydroxy, or a substituent selected from a hydrocarbon group having 1 to 10 carbon atoms.

27. The benzotriazole compound according to claim 14, wherein in the formula (I), the monovalent sulfur-containing group represented by the formula (i-1) is contained in $R^9$ at the 5-position, and wherein $R^1$, $R^2$, $R^3$, $R^4$ and $R^5$ each independently represent hydrogen, hydroxy, or a substituent selected from a hydrocarbon group having 1 to 18 carbon atoms; an aromatic group having 6 to 18 carbon atoms; an ether group having 1 to 18 carbon atoms; an alkoxy group having 1 to 18 carbon atoms; an ester group having 1 to 18 carbon atoms; a (meth)acryloyloxy group or polyoxyethylene group having 1 to 20 carbon atoms; or a hydrocarbon group having 1 to 18 carbon atoms, in which hydrogen atoms may be substituted with the abovementioned substituent groups, a base end may be interrupted by the abovementioned substituent groups, or carbon-carbon bonds may be interrupted by the abovementioned substituent groups.

28. The benzotriazole compound according to claim 27, wherein $R^1$, $R^2$, $R^3$, $R^4$ and $R^5$ each independently represent hydrogen, hydroxy, or a substituent selected from a hydrocarbon group having 1 to 10 carbon atoms.

\* \* \* \* \*